United States Patent
Robinson et al.

(10) Patent No.: US 12,403,114 B2
(45) Date of Patent: Sep. 2, 2025

(54) CANNABINOID ACID ESTER COMPOSITIONS AND USES THEREOF

(71) Applicants: EPM (IP), INC., San Francisco, CA (US); YISSUM RESEARCH DEVELOPMENT COMPANY OF THE HEBREW UNIVERSITY OF JERUSALEM LTD, Jerusalem (IL)

(72) Inventors: Dror Robinson, San Francisco, CA (US); Dan Peer, San Francisco, CA (US); Joseph Tam, Jerusalem (IL); Raphael Mechoulam, Jerusalem (IL)

(73) Assignees: EPM (IP), INC.; YISSUM RESEARCH DEVELOPMENT COMPANY OF THE HEBREW UNIVERSITY OF JERUSALEM LTD, Jerusalem (IL)

( * ) Notice: Subject to any disclaimer, the term of this patent is extended or adjusted under 35 U.S.C. 154(b) by 1025 days.

(21) Appl. No.: 17/437,780

(22) PCT Filed: Mar. 12, 2020

(86) PCT No.: PCT/US2020/022298
§ 371 (c)(1),
(2) Date: Sep. 9, 2021

(87) PCT Pub. No.: WO2020/186010
PCT Pub. Date: Sep. 17, 2020

(65) Prior Publication Data
US 2022/0151972 A1  May 19, 2022

Related U.S. Application Data

(60) Provisional application No. 62/903,848, filed on Sep. 22, 2019, provisional application No. 62/903,849, filed on Sep. 22, 2019, provisional application No. 62/903,852, filed on Sep. 22, 2019, provisional application No. 62/869,568, filed on Jul. 2, 2019, provisional application No. 62/856,160, filed on Jun. 3, 2019, provisional application No. 62/827,873, filed on Apr. 2, 2019, provisional application No.
(Continued)

(51) Int. Cl.
| | |
|---|---|
| A61K 31/216 | (2006.01) |
| A61K 31/352 | (2006.01) |
| A61K 36/185 | (2006.01) |
| A61K 45/06 | (2006.01) |
| A61K 47/10 | (2017.01) |
| A61K 47/24 | (2006.01) |
| A61K 47/40 | (2006.01) |
| A61P 1/00 | (2006.01) |
| A61P 1/16 | (2006.01) |
| A61P 3/00 | (2006.01) |
| A61P 3/04 | (2006.01) |
| A61P 3/06 | (2006.01) |
| A61P 3/10 | (2006.01) |
| A61P 13/12 | (2006.01) |
| A61P 15/00 | (2006.01) |
| A61P 17/00 | (2006.01) |
| A61P 19/02 | (2006.01) |

(52) U.S. Cl.
CPC .......... *A61K 31/216* (2013.01); *A61K 31/352* (2013.01); *A61K 36/185* (2013.01); *A61K 45/06* (2013.01); *A61K 47/10* (2013.01); *A61K 47/24* (2013.01); *A61K 47/40* (2013.01); *A61P 1/00* (2018.01); *A61P 1/16* (2018.01); *A61P 3/00* (2018.01); *A61P 3/04* (2018.01); *A61P 3/06* (2018.01); *A61P 3/10* (2018.01); *A61P 13/12* (2018.01); *A61P 15/00* (2018.01); *A61P 17/00* (2018.01); *A61P 19/02* (2018.01)

(58) Field of Classification Search
None
See application file for complete search history.

(56) References Cited

U.S. PATENT DOCUMENTS

| | | | |
|---|---|---|---|
| 5,342,971 | A | 8/1994 | Herlt et al. |
| 6,166,066 | A | 12/2000 | Makriyannis et al. |
| 6,403,126 | B1 | 6/2002 | Webster et al. |

(Continued)

FOREIGN PATENT DOCUMENTS

| | | |
|---|---|---|
| CN | 106810426 A | 6/2017 |
| CN | 108366962 A | 8/2018 |

(Continued)

OTHER PUBLICATIONS

Cardillo et.al. ((1972), Alkylation of Resorcinols with Monoterpenoid allylic alcohols in aqueous acid: synthesis of new cannabinoid derivatives, Tetrahedron Letters, 10, 945-948 (Year: 1972).*

(Continued)

*Primary Examiner* — Juliet C Switzer
*Assistant Examiner* — Dawanna Shar-Day White
(74) *Attorney, Agent, or Firm* — Dorsey & Whitney LLP

(57) ABSTRACT

The present disclosure provides pharmaceutical compositions including a cannabinoid acid ester compound alone or in combination with one or more additional cannabinoid compounds. In some embodiments, the cannabinoid acid ester compound is a cannabidiolic acid ester. A variety of therapeutic applications in which the cannabinoid acid ester compounds and pharmaceutical compositions find use are also provided, including combination therapies using cannabinoid acid ester compounds and one or more additional therapeutic agents.

20 Claims, 38 Drawing Sheets

Related U.S. Application Data

62/820,302, filed on Mar. 19, 2019, provisional application No. 62/816,935, filed on Mar. 12, 2019.

(56) References Cited

U.S. PATENT DOCUMENTS

| | | |
|---|---|---|
| 7,759,526 B2 | 7/2010 | Mechoulam et al. |
| 9,480,716 B2 | 11/2016 | Lacza et al. |
| 9,517,202 B2 | 12/2016 | Chen et al. |
| 9,670,133 B2 | 6/2017 | Koch et al. |
| 9,701,618 B2 | 7/2017 | Appendino et al. |
| 9,962,341 B2 | 5/2018 | Stott et al. |
| 2009/0247619 A1 | 10/2009 | Stinchcomb et al. |
| 2010/0298579 A1 | 11/2010 | Steup et al. |
| 2012/0237610 A1 | 9/2012 | Thorel et al. |
| 2013/0158126 A1 | 6/2013 | Munoz Blanco |
| 2013/0209483 A1 | 8/2013 | Mcallister |
| 2013/0224151 A1 | 8/2013 | Pearson et al. |
| 2015/0336874 A1 | 11/2015 | Koch et al. |
| 2016/0184258 A1 | 6/2016 | Murty et al. |
| 2016/0376211 A1 | 12/2016 | Mcallister et al. |
| 2018/0170846 A1 | 6/2018 | Mcallister et al. |
| 2018/0244642 A1 | 8/2018 | Koch et al. |
| 2020/0093785 A1* | 3/2020 | Stauff ............... A61K 45/06 |

FOREIGN PATENT DOCUMENTS

| | | | |
|---|---|---|---|
| EP | 2842933 B1 | 7/2015 | |
| EP | 2314580 B1 | 9/2015 | |
| EP | 3041815 B1 | 4/2019 | |
| GB | 1517590 A | 7/1978 | |
| JP | 2009510078 A | 3/2009 | |
| WO | 9953917 A1 | 10/1999 | |
| WO | 2006002050 A1 | 1/2006 | |
| WO | 2011110866 A1 | 9/2011 | |
| WO | 2013038157 A1 | 3/2013 | |
| WO | 2013062495 A2 | 5/2013 | |
| WO | 2013133647 A1 | 9/2013 | |
| WO | 2014182655 A1 | 11/2014 | |
| WO | 2014202990 A1 | 12/2014 | |
| WO | 2015158381 A1 | 10/2015 | |
| WO | 2015198071 A1 | 12/2015 | |
| WO | 2016059411 A1 | 4/2016 | |
| WO | 2016103254 A1 | 6/2016 | |
| WO | 2017055846 A1 | 4/2017 | |
| WO | 2017100063 A2 | 6/2017 | |
| WO | 2017137992 A1 | 8/2017 | |
| WO | 2017147691 A1 | 9/2017 | |
| WO | 2017178937 A1 | 10/2017 | |
| WO | 2017203529 A1 | 11/2017 | |
| WO | 2018002637 A1 | 1/2018 | |
| WO | 2018148787 A1 | 8/2018 | |
| WO | WO-2018235079 A1 * | 12/2018 | ............... A61P 1/08 |
| WO | 2019063122 A1 | 4/2019 | |
| WO | 2019234728 A1 | 12/2019 | |
| WO | 2020186010 A1 | 9/2020 | |

OTHER PUBLICATIONS

International Search Report and Written Opinion from International Application No. PCT/US2020/022298 mailed Jul. 24, 2020.
U.S. Appl. No. 62/816,935, filed Mar. 12, 2019.
U.S. Appl. No. 62/820,302, filed Mar. 19, 2019.
U.S. Appl. No. 62/827,873, filed Apr. 2, 2019.
U.S. Appl. No. 62/856,160, filed Jun. 3, 2019.
U.S. Appl. No. 62/869,568, filed Jul. 2, 2019.
U.S. Appl. No. 62/903,848, filed Sep. 22, 2019.
U.S. Appl. No. 62/903,849, filed Sep. 22, 2019.
U.S. Appl. No. 62/903,852, filed Sep. 22, 2019.
"Sodium Hyaluronate: Dosing, Indications, Interactions, Adverse Effects", Medscape, 2 pages, downloaded Feb. 11, 2020, retrieved from https://reference.medscape.com/drug/amvisc-hyalgan-sodium-hyaluronate-343375.

Ahmed, et al., "Cannabinoid Ester Constituents from High-Potency *Cannabis sativa*", Journal of Natural Products, vol. 71, No. 4, pp. 536-542, Apr. 2008.
Alexander, et al., "G Protein-Coupled Receptors", The Concise Guide to Pharmacology, vol. 174, pp. S17-S129, 2017, British Journal of Pharmacology.
Bendele, "Animal models of osteoarthritis", J Musculoskel Neuron Interact, 1, 2001, pp. 363-376.
Bluett, et al., "Central Anandamide Deficiency Predicts Stress-Induced Anxiety: Behavioral Reversal Through Endocannabinoid Augmentation", Transl Psychiatry, vol. 4, 5 pages, 2014, MacMillan Publishers Limited.
Bolognini, et al., "Cannabidiolic Acid Prevents Vomiting in Suncus Murinus and Nausea-Induced Behaviour in Rats by Enhancing 5-HT Receptor Activation", British Journal of Pharmacology, vol. 168, pp. 1456-1470, 2013.
Bosman, et al., "A Quantitative Method for Measuring Antipsoriatic Activity of Drugs by the Mouse Tail Test", Skin Pharmacol, 5, 1992, pp. 41-48.
Campos, et al., "Involvement of 5HT1A Receptors in the Anxiolytic-Like Effects of Cannabidiol Injected into the Dorsolateral Periaqueductal Gray of Rats", Psychopharmacology, vol. 199, pp. 223-230, 2008, May 1, 2008, Springer-Verlag.
Cascio, et al., "Evidence that the Plant Cannabinoid Cannabigerol is a Highly Potent α2-adrenoceptor Agonist and Moderately Potent 5HT Receptor Antagonist", British Journal of Pharmacology, vol. 159, pp. 129-141, 2010.
Christopoulos, et al., "International Union of Basic and Clinical Pharmacology. XC. Multisite Pharmacology: Recommendations for the Nomenclature of Receptor Allosterism and Allosteric Ligands", Pharmacological Reviews, vol. 66, pp. 918-947, Oct. 2014, U.S. Government Work.
Citti, et al., "Analysis of Cannabinoids in Commerical Hemp Seed Oil and Decarboxylation Kinetics Studies of Cannabidiolic Acid", Journal of Pharmaceutical and Biomedical Analysis, vol. 149, pp. 532-540, 2018, Elsevier.
Crombie, et al., "Cannabinoid Acits and Esters: Miniaturized Synthesis and Chromatographic Study", Phyiochemistry, vol. 16, pp. 1413-1420, 1977, Pergamon Press, England.
Curtis, et al., "Experimental Design and Analysis and Their Reporting: New Guidance for Publication in BJP", British Journal of Pharmacology, vol. 175, pp. 3461-3471, 2015.
El-Alfy, et al., "Antidepressant-like effect of Δ9-tetrahydrocannabinol and Other Cannabinoids Isolated from *Cannabis sativa* L", Pharmacol Biochen Behav. vol. 95, No. 4, pp. 434-442, Jun. 2010.
Fujimoto, et al., "Effects of Cannabinoids Given Orally and Reduced Appetite on the Male Rat Reproductive System", Pharmacology, 24, 1982, pp. 303-313.
Greenberg, et al., "Effects of Marihuana Use on Body Weight and Caloric Intake in Humans", Psychopharmacology, 49, 1976, pp. 79-84.
Grill, et al., "Chronic Decerebrate Rats Demonstrate Stiation But Not Bait-Shy-Ness", Science, vol. 201, No. 4352, Jul. 21, 1978, pp. 267-269, STOR.
Grlic, "A Comparative Study on Some Chemical and Biological Characteristics of Various Samples of Cannabis Resin", Issue 3, pp. 37-46, Jan. 1, 1962, United Nations Office on Drugs and Crime: Bulletin on Narcotics.
Hen-Shoval, et al., "Acute Oral Cannabidiolic Acid Methyl Ester Reduces Depression-Like Behavior in Two Genetic Animal Models of Depression", Behavioural Brain Research, vol. 351, 3 pages, 2018, Elsevier.
Izzo, et al., "Non-Psychotropic Plant Cannabinoids: New Therapeutic Opportunities from an Ancient Herb", Trends in Pharmacological Sciences, vol. 30, No. 10, pp. Sep. 2, 2019, pp. 515-527.
Jamontt, et al., "The Effects of Δ9-tetrahydrocannabinol and Cannabidiol Alone and in Combination on Damage, Inflammation and in vitro Motility Disturbances in Rat Colitis", British Journal of Pharmacology, vol. 160, pp. 712-723, 2010.
Jasirwan, et al., "The Role of Gut Microbiota in Non-Alcoholic Fatty Liver Disease: Pathways of Mechanisms", Bioscience of Microbiota, Food and Health, vol. 38, No. 3, pp. 81-88, 2019.

(56) References Cited

OTHER PUBLICATIONS

Kabelik, "Hemp as a Medicament: Summary of the Study", Issue 3-002, 1960, UNODC—Bulletin on Narcotics.
Kilkenny, et al., "Animal Research: Reporting in vivo Experiments: The ARRIVE Guidelines", British Pharmacological Society, vol. 160, pp. 1577-1579, 2010.
Kogan, et al., "Cannabidiol, a Major Non-Psychotropic Cannabis Constituent Enhances Fracture Healing and Stimulates Lysyl Hydroxylase Activity in Osteoblasts", Journal of bone and Mineral Research, vol. 30, No. 10, pp. 1905-1913, Oct. 2015.
Laprairie, et al., "Cannabidiol is a Negative Allosteric Modulator of the Cannabinoid CB1 Receptor", British Journal of Pharmacology, vol. 172, pp. 4790-4805, 2015.
Lee, et al., "Cannabidiol Regulation of Emotion and Emotional Memory Processing: Relevance for Treating Anxiety-Related and Substance Abuse Disorders", British Journal of Pharmacology, vol. 174, pp. 3242-3256, 2017.
Ligresti, et al., "Antitumor Activity of Plant Cannabinoids with Emphasis on the Effect of Cannabidiol on Human Breast Carcinoma", The Journal of Pharmacology and Experimental Therapeutics, vol. 318, No. 3, pp. 1375-1387, 2006.
Limebeer, et al., "Inverse Agonism of Cannabinoid CB1 Receptors Potentiates LiCl-Induced Nausea in the Conditioned Gaping Model in Rats", British Journal of Pharmacology, vol. 161, pp. 336-349, 2010.
Massi, et al., "Antitumor Effects of Cannabidiol, A Nonpsychoactive Cannabinoid, on Human Glioma Cell Lines", The Journal of Pharmacology and Experimental Therapeutics, vol. 308, No. 3, pp. 838-845, 2004.
Masuki, et al., "Growth Factor and Pro-Inflammatory Cytokine Contents in Platelet-Rich Plasma (PRP), Plasma Rich in Growth Factors (PRGF), Advanced Platelet-Rich Fibrin (A-PRF), and Concentrated Growth Factors (CGF)", International Journal of Implant Dentistry, vol. 2, No. 19, 6 pages, 2016, Springer.
McGrath, et al., "Implementing Guidelines on Reporting Research Using Animals (ARRIVE etc.): New Requirements for Publication in BJP" British Journal of Pharmacology, vol. 172, pp. 3189-3193, 2015.
Mechoulam, et al., "Cannabidiol—Recent Advances", Chemistry & Biodiversity, vol. 4, 2007, pp. 1678-1692.
Mechoulam, et al., "Cannabidiol: An Overview of Some Pharmacological Aspects", The Journal of Clinical Pharmacology, vol. 42, No. 11, pp. 11S-19S, 2002, SAGE.
Mechoulam, et al., "Carboxylation of Resorcinols with Methylmagnesium Carbonate. Synthesis of Cannabinoid Acids", Journal of the Chemical Society D: Chemical Communications, Issue 7, pp. 343-344, 1969.
Mechoulam, et al., "The Isolation and Structure of Cannabinolic Cannabidiolic and Cannabigerolic Acids", Tetrahedron, vol. 21, pp. 1223-1229, 1965, Pergamon Press Ltd., Northern Ireland.
Owens, et al., "Biomarkers and the Role of Mast Cells as Facilitators of Inflammation and Fibrosis in Chronic Kidney Disease", Translational Andrology and Urology, vol. 8, Suppl. 2, pp. S175-S183, 2019.
Patel, et al., "The Endocannabinoid System as a Target for Novel Anxiolytic Drugs", Neuroscience and Biobehavioral Review, vol. 76, pp. 56-66, 2017, Elsevier.
Pertwee, et al., "Cannabidiolic Acid Methyl Ester, A Stable Synthetic Analogue of Cannabidiolic Acid, Can Produce 5-HT1A Receptor-Mediated Suppression of Nausea and Anxiety in Rats", British Journal of Pharmacology, vol. 174, pp. 100-112, 2018.
Petrzilka, et al., "Synthese von Haschisch-Inhaltsstoffen", Helvetica Chimica ACTA, vol. 52 No. 4, pp. 1102-1133, 1969.
Philpott, et al., "Attenuation of early phase inflammation by cannabidiol prevents pain and nerve damage in rat osteoarthritis", Pain, 158, 2017, pp. 2442-2451.
Potter, et al., "Potency of Δ9-THC and Other Cannabinoids in Cannabis in England in 2005: Implications for Psychoactivity and Pharmacology", Journal of Forensic Science, vol. 53, No. 1, 7 pages, Jan. 2008, American Academy of Forensic Sciences.
Rock, et al., "A Comparison of Cannabidiolic Acid With Other Treatments for Anticipatory Nausea Using a Rat Model of Contextually Elicited Conditioned Gaping", Psychopharmacology, vol. 231, pp. 3207-3215, 2014.
Rock, et al., "Cannabidiol, A Non-Psychotropic Component of Cannabis, Attenuates Vomiting and Nausea-Like Behaviour via Indirect Agonism of 5-HT1A Somato-Dendritic Autoreceptors in the Dorsal Raphe Nucleus", British Journal of Pharmacology, vol. 165, pp. 2620-2634, 2012.
Rock, et al., "Effect of Combined doses of Δ9-Tetrahydrocannabinol (THC) and Cannabidiolic Acid (CBDA) on Acute and Anticipatory Nausea Using Rat (Sprague-Dawley) Models of Conditioned Gaping", Psychopharmacology, vol. 232, pp. 4445-4454, 2015, Springer.
Rock, et al., "Effect of Combined Oral Doses of Δ9- Tetrahydrocannabinol (THC) and Cannabidiolic Acid (CBDA) on Acute and Anticipatory Nausea Using Rat Models", Psychopharmacology, vol. 233, pp. 3353-3360, 2016, Springer.
Rock, et al., "Effect of Low Doses of Cannabidiolic Acid and Ondansetron on LiCl-Induced Conditioned Gaping (a model of nausea-induced behaviour) in Rats", British Journal of Pharmacology, vol. 169, pp. 685-692, 2013.
Rock, et al., "Effect of Prior Foot Shock Stress and Δ9-Tetrahydrocannabinol, Cannabidiolic Acid, and Cannabidiol on Anxiety-Like Responding in the Light-Dark Emergence Test in Rats", Psychopharmacology, vol. 234, pp. 2207-2217, 20017, Springer.
Rock, et al., "Interaction Between Non-Psychotropic Cannabinoids in Marihuana: Effect of Cannabigerol (CBG) on the Anti-Nausea or Anti-Emetic Effects of Cannabidiol (CBD) in Rats and Shrews", Psychopharmacology, vol. 215, pp. 505-512, 2011.
Rock, et al., "Synergy Between Cannabidiol, Cannabidiolic Acid, and Δ9-Tetrahydrocannabinol in the Regulation of Emesis in the Suncus Murinus", Behavioral Neuroscience, vol. 129, No. 3, pp. 368-370, 2015.
Rock, et al., "The Effect of Cannabidiol and URB597 on Conditioned Gaping (a model of nausea) Elicited by a Lithium-Paired Context in the Rat", Psychopharmacology, vol. 196, pp. 389-395, 2008, Springer-Verlag.
Scheinin, et al., "Validation of the interleukin-10 knockout mouse model of colitis: antitumour necrosis factor-antibodies suppress the progression of colitis", Clin Exp Immunol, 133, 2003, pp. 34-43.
Shoyama, et al., "The Isolation and Structures of Four New Propyl Cannabinoid Acids, Tetrahydrocannabivarinic Acid, Cannabidivarinic Acid, Cannabichromevarinic Acid and Cannabigerovarinic Acid, from Thai Cannabis, Meao Variant", Chem. Pharm. Bull, vol. 25, No. 9, pp. 2306-2311, 1977.
Southan, et al., "The IUPHAR/BPS Guide to Pharmacology in 2016: Towards Curated Quantitative Interactions Between 1300 Protein Targets and 6000 Ligands", Nucleic Acids Research, vol. 44, database issue, Oct. 12, 2015.
Storr, et al., "Cannabis Use Provides Symptom Relief in Patients with Inflammatory Bowel Disease but Is Associated with Worse Disease Prognosis in Patients with Crohn's Disease", Inflamm. Bowel Dis., vol. 20, No. 3, pp. 472-480, Mar. 2014, Crohn's & Colitis Foundation of America, Inc.
Takeda, et al., "Cannabidiolic Acid-Mediated Selective Down-Regulation of c-fos in Highly Aggressive Breast Cancer MDA-MB-231 Cells: Possible Involvement of its Down-Regulation in the Abrogation of Agressiveness", J. Nat. Med., vol. 71, pp. 286-291, 2017, Springer.
Takeda, et al., "Down-Regulation of Cyclooxygenase-2 (COX-2) by Cannabidiolic Acid in Human Breast Cancer Cells", The Journal of Toxicological Sciences, vol. 39, No. 5, pp. 711-716, 2014.
Tam, et al., "Peripheral Cannabinoid-1 Receptor Inverse Agonism Reduces Obesity by Reversing Leptin Resistance", Cell Metabolism, 16, Aug. 8, 2012, pp. 167-179.
Yanagisawa, et al., "Weekly injections of Hylan G-F 20 delay cartilage degeneration in partial meniscectomized rat knees", BMC Musculoskeletal Disorders, 17:188, DOI 10.1186/s12891-016-1051-6, 2016, pp. 1-10.
Zanelati, et al., "Antidepressant-Like Effects of Cannabidiol in Mice: Possible Involvement of 5-HT1A Receptors", British Journal of Pharmacology, vol. 159, pp. 122-128, 2010.

(56) References Cited

OTHER PUBLICATIONS

Zhornitsky, et al., "Cannabidiol in Humans—The Quest for Therapeutic Targets", Pharmaceuticals, vol. 5, pp. 529-552, 2012, www.mdpi.com/journal/pharmaceuticals.

Zuardi, et al., "Effects of Ipsapirone and Cannabidiol on Human Experimental Anxiety", Journal of Psychopharmacology, vol. 7, No. 1, pp. 82-88, 1993, British Association for Psychopharmacology.

* cited by examiner

*P<0.05 vs. STD-Veh; #P<0.05 vs. HFD-Veh

Teklad Custom Research Diet Data Sheet

TD.95217  Adjusted Fat Diet

| Formula | g/Kg |
|---|---|
| Casein | 227.7 |
| DL-Methionine | 3.3 |
| Sucrose | 150.0 |
| Corn Starch | 205.24 |
| Maltodextrin | 100.0 |
| Vegetable Shortening, hydrogenated (Primex) | 106.3 |
| Anhydrous Milkfat | 40.0 |
| Soybean Oil | 40.0 |
| Cellulose | 72.5 |
| Mineral Mix, AIN-93G-MX (94046) | 38.5 |
| Calcium Phosphate, dibasic | 2.42 |
| Vitamin Mix, Teklad (40060) | 11.0 |
| Choline Bitartrate | 3.0 |
| Ethoxyquin, antioxidant | 0.04 |

*Key Features*
- Purified Diet
- Diet Induced Obesity
- Trans Fatty Acids

*Key Planning Information*
- *Products are made fresh to order*
- Store products at 4°C or lower
- Used within 6 months (applicable to most diets)
- Box labeled with product name, manufacturing date, and lot number
- Replace diet at minimum once per week
  *More frequent replacement may be advised*
- Box labeled with product name
  - 2 weeks non-irradiated
  - 4 weeks irradiated

*Key Features*
- 1/2" Pellet or Powder (crumbly)
- Minimum order 3 Kg
- Irradiation available upon request

FIG. 32

CANNABINOID ACID ESTER COMPOSITIONS AND USES THEREOF

CROSS-REFERENCE TO RELATED APPLICATIONS

This application is a National Stage of PCT/US2020/022298 filed Mar. 12, 2020, which claims the benefit of U.S. Application No. 62/816,935, filed Mar. 12, 2019, U.S. Application No. 62/820,302, filed Mar. 19, 2019, U.S. Application No. 62/827,873, filed Apr. 2, 2019, U.S. Application No. 62/856,160, filed Jun. 3, 2019, U.S. Application No. 62/869,568, filed Jul. 2, 2019, U.S. Application No. 62/903,848, filed Sep. 22, 2019, U.S. Application No. 62/903,849, filed Sep. 22, 2019, and U.S. Application No. 62/903,852, filed Sep. 22, 2019, which applications are hereby incorporated by reference in their entirety.

INTRODUCTION

Cannabidiol (CBD) is the major non-psychotropic phytocannabinoid compound present in the plant *Cannabis sativa*, making up to 40% of the cannabinoids in *Cannabis* extracts. Cannabidiolic acid (CBDA) is another major constituent of *Cannabis sativa* plant. The cannabinoid acids such as CBDA are precursors of the natural cannabinoids. CBD can be produced by decarboxylation of CBDA. Due to CBDA's relative instability to decarboxylation, its chemical structure was first elucidated by analysis of an ester derivative, namely cannabidiolic acid methyl ester (CBDA-Me).

The cannabinoid based compounds may have a variety of biological activities and effects. Elucidation of desirable non-traditional biological activities of cannabinoid acid compounds, and the demonstration of useful therapeutic applications for such compounds is of interest.

SUMMARY

The present disclosure provides pharmaceutical compositions including a cannabinoid acid ester compound alone or in combination with one or more additional cannabinoid compounds. In some embodiments, the cannabinoid acid ester compound is cannabidiolic acid ester. A variety of therapeutic applications in which the cannabinoid acid ester compounds and pharmaceutical compositions find use are also provided, including combination therapies using cannabinoid acid ester compounds and one or more additional therapeutic agents.

Accordingly, in a first aspect, the present disclosure provides a pharmaceutical composition comprising:

a cannabidiolic acid ester compound of formula (I),

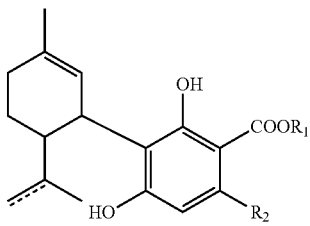

(I)

wherein $R_1$ and $R_2$ are independently selected from $C_1$-$C_{10}$ alkyl, substituted $C_1$-$C_{10}$ alkyl, $C_2$-$C_{10}$ alkenyl, substituted $C_2$-$C_{10}$ alkenyl, $C_2$-$C_{10}$ alkynyl, and substituted $C_2$-$C_{10}$ alkynyl, or a pharmaceutically acceptable salt thereof; and a pharmaceutically acceptable excipient; for use in:
(i) treating a joint disease or dysfunction;
(ii) treating a skin disease or disorder;
(iii) treating a gastrointestinal disease or disorder;
(iv) attenuating, alleviating, or treating a uterine-related disorder;
(v) reducing or maintaining cholesterol levels or lowering LDL/HDL ratio; or
(vi) treating Non-Alcoholic Fatty Liver Disease (NAFLD), chronic kidney disease (CDK), diabetes dyslipidemia, metabolic syndrome, hyperglycemia, or obesity.

In a second aspect, the present disclosure provides a pharmaceutical composition, comprising: a cannabidiolic acid ester compound of formula (I):

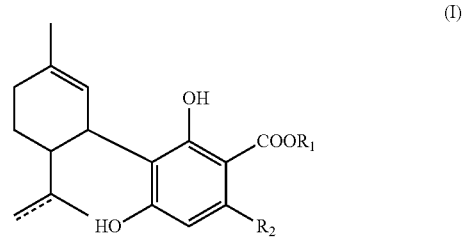

(I)

wherein $R_1$ and $R_2$ are independently selected from $C_1$-$C_{10}$ alkyl, substituted $C_1$-$C_{10}$ alkyl, $C_2$-$C_{10}$ alkenyl, substituted $C_2$-$C_{10}$ alkenyl, $C_2$-$C_{10}$ alkynyl, and substituted $C_2$-$C_{10}$ alkynyl, or a pharmaceutically acceptable salt thereof; and a pharmaceutically acceptable excipient.

In some embodiments of the pharmaceutical composition, $R_1$ is $C_1$-$C_6$ alkyl or substituted $C_1$-$C_6$ alkyl. In some embodiments of the pharmaceutical composition, wherein $R_1$ is selected from methyl, ethyl, propyl, butyl, and pentyl. In some embodiments of the pharmaceutical composition, $R_1$ is methyl. In some embodiments of the pharmaceutical composition, $R_2$ is $C_1$-$C_{10}$ alkyl, or substituted $C_1$-$C_{10}$ alkyl. In some embodiments of the pharmaceutical composition, $R_2$ is $C_{2-6}$ alkyl. In some embodiments of the pharmaceutical composition, $R_2$ is pentyl.

In some embodiments of the pharmaceutical composition, the compound of formula (I) is cannabidiolic acid methyl ester (CBDA-Me) of formula (II):

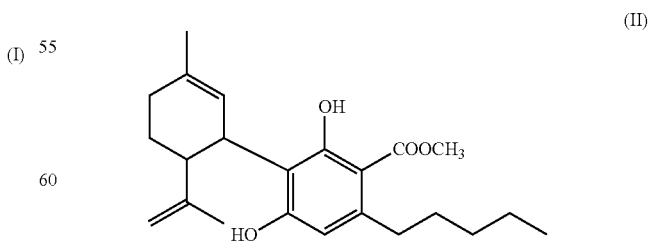

(II)

or a pharmaceutically acceptable salt thereof.

In some embodiments of the pharmaceutical composition, the CBDA-Me is of formula (IIa):

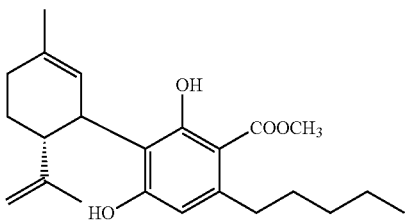

(IIa)

or a pharmaceutically acceptable salt thereof.

In some embodiments of the pharmaceutical composition, the CBDA-Me is of formula (IIb):

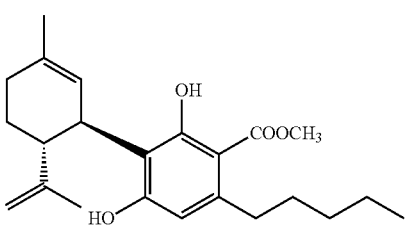

(IIb)

or a pharmaceutically acceptable salt thereof.

In some embodiments of the pharmaceutical composition, the composition further comprises one or more additional cannabinoid compounds.

In a third aspect, the present disclosure provides for a method of treating a joint disease or dysfunction, comprising administering a therapeutically effective amount of a pharmaceutical composition as described herein to a subject having a joint disease or dysfunction.

In some embodiments of the method, the joint disease or dysfunction is joint inflammation or joint degeneration. In some embodiments of the method, the joint disease or dysfunction is osteoarthritis.

In a fourth aspect, the present disclosure provides for a method of at least ameliorating a skin disease or disorder comprising administering a therapeutically effective amount of a pharmaceutical composition as described herein to a subject having a skin disease or disorder.

In some embodiments of the method, the skin disease or disorder is an inflammatory skin disease or disorder. In another embodiment, the inflammatory skin disease or disorder is selected from psoriasis, atopic dermatitis, eczema, actinic keratosis, ichthyosis, Bowen's disease, keratoacanthoma, lichen sclerosus, hidradenitis suppurativa, scborrheic keratosis, rosacea, pityriasis lichenoid, acne, and seborrhea.

In some embodiments of the method, the inflammatory skin disease or disorder is psoriasis. In some embodiments of the method, the inflammatory skin disease or disorder is diabetic skin disorder. In some embodiments of the method, the inflammatory skin disease or disorder is epidermal hyperproliferation or dermal inflammation.

In a fifth aspect, the present disclosure provides for a method of treating a gastrointestinal disease or disorder, comprising administering a therapeutically effective amount of the pharmaceutical composition as described herein to a subject having a gastrointestinal disease or disorder.

In some embodiments of the method, the gastrointestinal disease or disorder is selected from irritable bowel syndrome (IBS), inflammatory bowel disease (IBD), gastrointestinal motility disorders, constipation, functional gastrointestinal disorder, gastroesophageal reflux disease (GERD), duodenogastric influx, functional heartburn, dyspepsia, visceral pain, gastroparesis, and chronic intestinal pseudo-obstruction. In some embodiments of the method, the gastrointestinal disease or disorder is IBS. In some embodiments of the method, the gastrointestinal disease or disorder is IBD.

In a sixth aspect, the present disclosure provides for a method of treating a uterine-related disease, comprising administering a therapeutically effective amount of a pharmaceutical composition as described herein to a subject having a uterine-related disease.

In some embodiments of the method, the uterine-related disease is selected from endometriosis, dysmenorrhea, irregular menstrual bleeding, and dyspareunia.

In some embodiments of the method of treating a uterine-related disease, the pharmaceutical composition is administered orally. In some embodiments of the method of treating a uterine-related disease, the pharmaceutical composition is administered vaginally using an applicator suitable for vaginal administration.

In some embodiments of the method of treating a uterine-related disease, the method further comprises co-administering one or more additional active pharmaceutical ingredients (API). In some embodiments of the method of treating a uterine-related disease, the one or more additional API is non-steroidal anti-inflammatory drug (NSAID). In another embodiment of the method, the NSAID is selected from acetyl salicylic acid, indometacin, sulindac, phenylbutazone, diclofenac, fentiazac, ketorolac, piroxicam, tenoxicam, mecoxicam, meloxicam, cinnoxicam, ibufenac, ibuprofen, naproxen, ketoprofen, nabumetone, niflumic acid, nimesulide, and pharmaceutically acceptable salts thereof.

In some embodiments of the method of treating a uterine-related disease, the NSAID is a Cox-2 inhibitor. In another embodiment, the Cox-2 inhibitor is selected from celecoxib, rofecoxib, parecoxib, and valdecoxib.

In some embodiments of the method of treating a uterine-related disease, the one or more additional API is a hormonal agent. In another embodiment, the hormonal agent comprises danazol, an oral contraceptive, GnRH agonist and antagonist, progestin, antiprogestins, medroxyprogesterone acetate, and aromatase inhibitor.

In another aspect, the present disclosure provides a method of treating a heart disease or a heart-related condition, comprising administering a therapeutically effective amount of the pharmaceutical composition as described herein to a subject in need thereof.

In some embodiments, the method reduces or maintains cholesterol levels, lowers LDL/HDL ratio, treats a high-cholesterol related disease or disorder, or treats a cardiovascular disease. In some embodiments, the method treats or prevents atherosclerosis or hypercholesterolemia.

In some embodiments of the method of treating a heart disease or a heart-related condition, the administration of the pharmaceutical composition results in reduction of at least one lipid parameter in the subject. In some embodiments of the method, the subject has an LDL-C level greater than or equal to 70 mg/dL.

In some embodiments of the method of treating a heart disease or a heart-related condition, the pharmaceutical composition is administered in combination with one or more additional therapeutic agents for reducing cholesterol. In another embodiment, the one or more additional therapeutic agents is a statin.

In yet another aspect, the present disclosure provides a method of treating Non-Alcoholic Fatty Liver Disease (NAFLD), chronic kidney disease (CKD), diabetes, dyslipidemia, metabolic syndrome, hyperglycemia or obesity, the method comprising administering a therapeutically effective amount of the pharmaceutical composition as described herein to a subject in need thereof. In some embodiment, the pharmaceutical composition is co-administered in combination with one or more additional therapeutic agents.

BRIEF DESCRIPTION OF THE DRAWINGS

These and other features, aspects, and advantages of the present invention will become better understood with regard to the following description, and accompanying drawings, where:

FIG. 32 shows the data sheet of Teklad TD95217 adipogenic diet.

DETAILED DESCRIPTION

Cannabinoid Acid Ester Compounds

Figure 1:
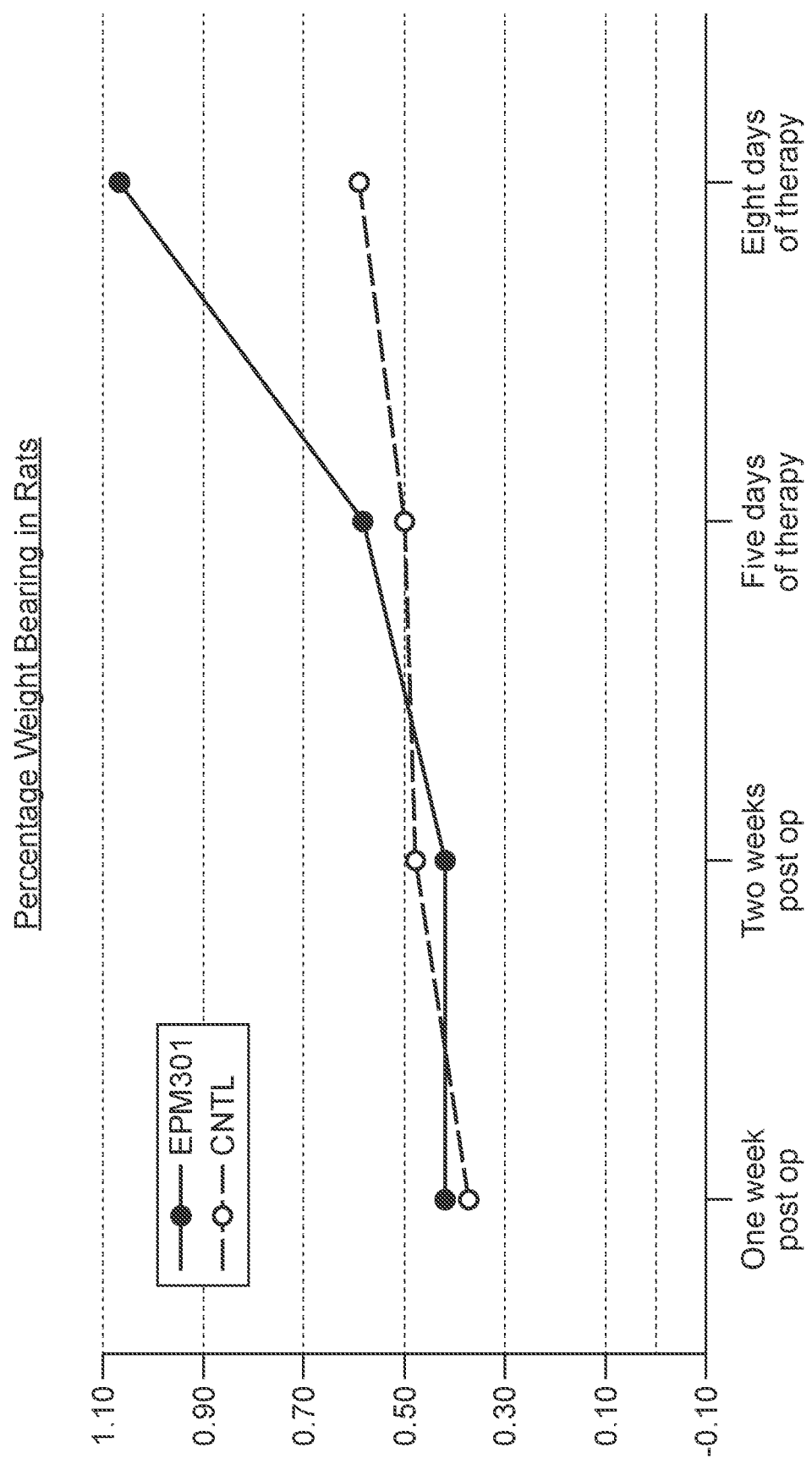
FIG. 1 shows the effect of CBDA-Me (EPM-301) on percent weight bearing in a rat partial meniscectomy\ACL transection model of surgical induced osteoarthritis and pain induced incapacitance.

The term "cannabinoid" refers to a compound that interacts with and binds to a cannabinoid receptor compound. Binding compounds (i.e., ligands) for cannabinoid receptors include, but are not limited to, endocannabinoids (produced naturally in the body by human and animals), phytocannabinoids (found in cannabis and some other plants), and synthetic cannabinoids (manufactured artificially). The term "cannabinoid acid" refers to a carboxylic acid-substituted form or derivative of a cannabinoid compound. The term "cannabinoid acid ester" refers to an ester form of a cannabinoid acid compound, where the carboxylic acid substituent of the parent cannabinoid acid is in an ester form.

The term "cannabidiol" refers to the phytocannabinoid cannabidiol (CBD). CBDA can be referred to as 2-[3-methyl-6-(1-methylethenyl)-2-cyclohexen-1-yl]-5-pentyl-1,3-benzenediol, and has the following structure:

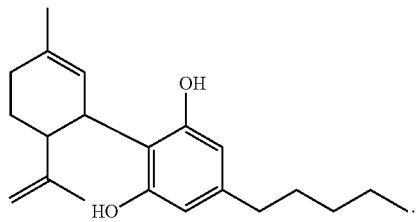 [SMILES: C=C(C)C1CCC(C)=CC1c1c(O)cc(CCCCC)cc1O]

CBD can be obtained from industrial hemp extract (with, in some cases, a trace amount of THC) or from cannabis extract using high CBD cannabis cultivars. Cannabidiol may be obtained from plant extract, or may be prepared synthetically (manufactured artificially).

Cannabidiolic acid (CBDA) is an acid form of CBD. CBDA can be referred to a 2,4-dihydroxy-3-[3-methyl-6-prop-1-en-2-ylcyclohex-2-en-1-yl]-6-pentylbenzoic acid and has the following structure:

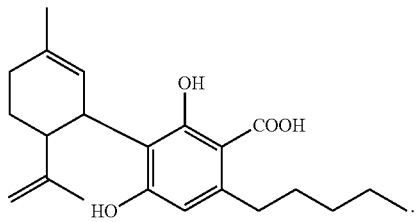 [SMILES: C=C(C)C1CCC(C)=CC1c1c(O)cc(CCCCC)c(C(=O)O)c1O]

The terms "cannabidiolic acid ester" and "cannabidiolic ester" are used interchangeably and refer to esters of CBDA. The term "CBDA-Me" refers to cannabidiolic acid methyl ester, the methyl ester form of CBDA.

CBDA activates the serotonin 5-HT1A Receptor with a significantly greater affinity for the 5-HT1A receptor than CBD. 5-HT1A Receptor-mediated signaling cascades can have physiologically important effects on the regulation of a variety of biological functions and activities.

The present disclosure provides compositions including cannabinoid acid ester compounds that find use in a variety of therapeutic applications, e.g., as described herein. The inventors have discovered and elucidated a variety of desirable biological activities and new therapeutic applications of cannabinoid acid ester compounds, e.g., as described herein. The ester form of a cannabinoid acid compound can be a desirable and useful form of a bioactive compound suitable for administration to a subject in a therapeutic application (e.g., as described herein). In some cases, the ester form is generally more stable, e.g., in vivo, than the parent cannabinoid acid compound. In some embodiments, the cannabinoid acid ester compound is a cannabidiolic acid ester (CBDA ester).

A variety of cannabinoid acid compounds can be adapted for use in the therapeutic methods described herein in an ester form. Any convenient ester forms of cannabinoid acid compounds can be utilized. The particular ester form of the cannabinoid acid compound can be selected to provide for a desired stability profile and half-lives in vivo of the administered drug and any active metabolites thereof.

Cannabinoid acid compounds of interest include cannabidiolic acid and analogs of CBDA that have the same core structure but which include different substituents, e.g., as a replacement for the pentyl group of CBDA. In some embodiments, the cannabinoid acid ester compound is a CBDA ester or analog thereof of formula (I):

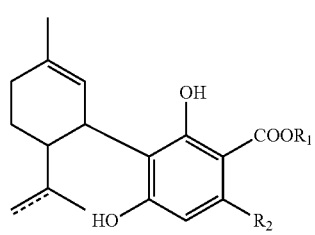

(I)

where $R_1$ and $R_2$ are independently selected from $C_1$-$C_{10}$ alkyl, substituted $C_1$-$C_{10}$ alkyl, $C_2$-$C_{10}$ alkenyl, substituted $C_2$-$C_{10}$ alkenyl, $C_2$-$C_{10}$ alkynyl, and substituted $C_2$-$C_{10}$ alkynyl, or a pharmaceutically acceptable salt thereof.

In some embodiments of formula (I), the compound is of formula (Ia):

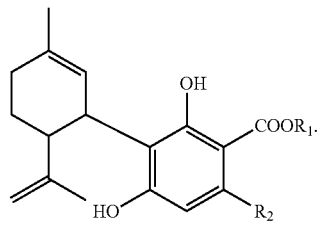

(Ia)

In some embodiments of formula (I), the compound is of formula (Ib):

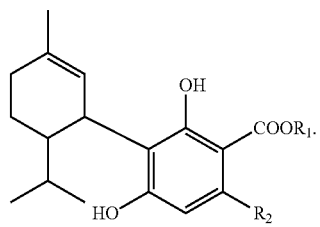

(Ib)

In some embodiments of formula (I)-(Ib), $R_1$ is $C_1$-$C_{10}$ alkyl or substituted $C_1$-$C_{10}$ alkyl. In some embodiments of the compound of formula (I)-(Ib), $R_1$ is $C_1$-$C_6$ alkyl or substituted $C_1$-$C_6$ alkyl. In another embodiment, $R_1$ is selected from methyl, ethyl, propyl, butyl, and pentyl. In another embodiment, $R_1$ is methyl. In some embodiments of formula (I)-(Ib), $R_1$ is ethyl. In some embodiments of formula (I)-(Ib), $R_1$ is isopropyl. In some embodiments of formula (I)-(Ib), $R_1$ is propyl. In some embodiments of formula (I)-(Ib), $R_1$ is isobutyl. In some embodiments of formula (I), $R_1$ is butyl. In some embodiments of formula (I)-(Ib), $R_1$ is pentyl.

In some embodiments of formula (I)-(Ib), $R_1$ is $C_2$-$C_{10}$ alkenyl, or substituted $C_2$-$C_{10}$ alkenyl. In some embodiments of formula (I)-(Ib), $R_1$ is $C_2$-$C_{10}$ alkynyl, or substituted $C_2$-$C_{10}$ alkynyl.

In some embodiments of the compound of formula (I)-(Ib), $R_2$ is $C_1$-$C_{10}$ alkyl, or substituted $C_1$-$C_{10}$ alkyl. In another embodiment, $R_2$ is $C_{2-6}$ alkyl. In another embodiment, $R_2$ is pentyl. In some embodiments of formula (I)-(Ib), $R_2$ is ethyl. In some embodiments of formula (I)-(Ib), $R_2$ is propyl. In some embodiments of formula (I), $R_2$ is butyl. In some embodiments of formula (I)-(Ib), $R_2$ is pentyl. In some embodiments of formula (I)-(Ib), $R_2$ is hexyl.

In some embodiments of formula (I)-(Ib), $R_1$ and $R_2$ are independently $C_1$-$C_{10}$ alkyl or substituted $C_1$-$C_{10}$ alkyl. In some embodiments of formula (I)-(Ib), $R_1$ and $R_2$ are independently $C_1$-$C_{10}$ alkyl. In some embodiments of formula (I)-(Ib), $R_1$ is $C_1$-$C_6$ alkyl, and $R_2$ is $C_{2-6}$ alkyl.

In some embodiments of formula (I), the compound is cannabidiolic acid methyl ester (CBDA-Me) of formula (II):

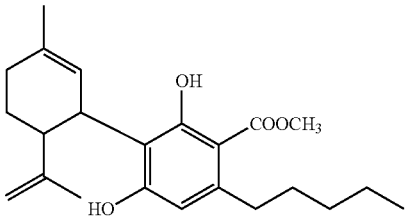

(II)

or a pharmaceutically acceptable salt thereof.

It is understood that unless the specific stereochemistry of the compounds described herein (e.g., compounds of formulae (I)-(Va)) is expressly indicated, all chiral, stereoisomeric diastereomeric, and racemic forms of the compounds are meant to be included in the present disclosure. The compound can be enantiomerically pure, a stereoisomeric mixture, or a diastereomeric mixture. In some embodiments, the CBDA-Me compound or a salt thereof is a enantiomerically pure CBDA-Me, a stereoisomeric mixture of CBDA-Me, and/or a diastereomeric mixture of CBDA-Me.

In some embodiments of formula (II), the CBDA-Me is of formula (IIa):

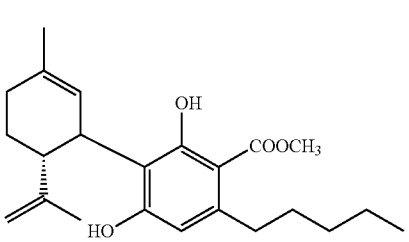

(IIa)

or a pharmaceutically acceptable salt thereof. In another embodiment, the compound of formula (IIa) is EPM-301.

In some embodiments of formula (II), the CBDA-Me is of formula (IIb):

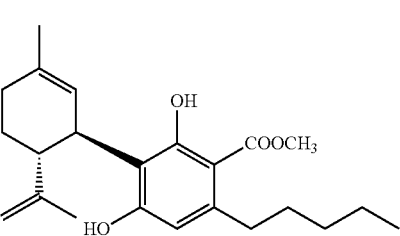

(IIb)

or a pharmaceutically acceptable salt thereof. In another embodiment, the compound of formula (IIb) is HU-580.

Also provided are deuterated analogs of cannabinoid acid ester compounds. In some cases, the compounds are deuterated analogs of CBDA ester compounds. A deuterated analog of a compound of formulae (I)-(IIb) is a compound where one or more hydrogen atoms are substituted with a deuterium. In some embodiments, the deuterated analog is a compound of formula (I) that includes a deuterated $R_1$ group. In some embodiments of a deuterated analog of formula (I), $R_1$ is a $C_1$-$C_{10}$ alkyl or substituted $C_1$-$C_{10}$ alkyl including at least one deuterium atom. In some embodiments of a deuterated analog of formula (I), $R_1$ is a $C_1$-$C_6$ alkyl or substituted $C_1$-$C_6$ alkyl including at least one deuterium atom. In some embodiments of a deuterated analog of formula (I), $R_1$ is —$CD_3$. In some embodiments of a deuterated analog of formula (I), $R_1$ is —$CD_2$-$CD_3$. In some embodiments of a deuterated analog of formula (I), the deuterated analog of the cannabinoid acid ester compound includes an $R_2$ group that is deuterated. In some embodiments of a deuterated analog of formula (I), $R_2$ is a $C_1$-$C_{10}$ alkyl or substituted $C_1$-$C_{10}$ alkyl including at least one deuterium atom. In some embodiments of a deuterated analog of formula (I), $R_2$ is a $C_2$-$C_6$ alkyl or substituted $C_2$-$C_6$ alkyl including at least one deuterium atom.

In some embodiments, the compound is a deuterated analog of CBDA-Me ester of formula (III):

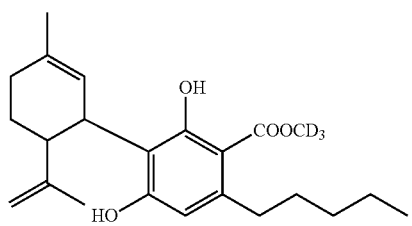

(III)

or a pharmaceutically acceptable salt thereof.

In some embodiments of formula (III), the deuterated analog of CBDA-Me ester is the compound of formula (IIIa):

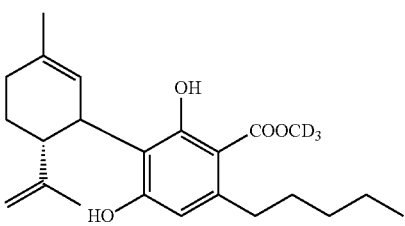

(IIIa)

or a pharmaceutically acceptable salt thereof.

In some embodiments of the compound of formula (III), the deuterated analog of CBDA-Me ester is the compound of formula (IIIb):

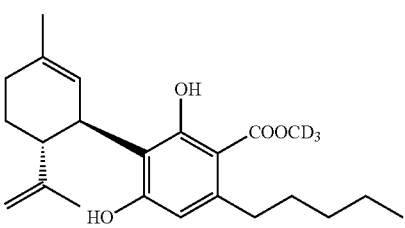

(IIIb)

or a pharmaceutically acceptable salt thereof.

Also provided are fluorinated analogs of cannabinoid acid ester compounds. In some cases, the compounds are fluorinated analogs of CBDA ester compounds. A fluorinated analog of a compound of formulae (I)-(Va) is a compound where one or more hydrogen atoms are substituted with a fluorine. In some embodiments of the compound of formula (I), the fluorinated analog includes an $R_1$ group that is fluorinated. In some embodiments of formula (I), $R_1$ is a substituted $C_1$-$C_{10}$ alkyl including at least one fluoro substituent. In some embodiments of formula (I), $R_1$ is a substituted $C_1$-$C_6$ alkyl including at least one fluoro substituent. In some embodiments of formula (I), $R_1$ is —$CF_3$. In some embodiments of formula (I), $R_1$ is —$CF_2$—$CF_3$. In some embodiments of the compound of formula (I), the fluorinated analog of the cannabinoid acid ester compound includes an $R_2$ group that is fluorinated. In some embodiments of formula (I), $R_2$ is a substituted $C_1$-$C_{10}$ alkyl including at least one fluoro substituent. In some embodiments of formula (I), $R_2$ is a substituted $C_2$-$C_6$ alkyl including at least one fluoro substituent.

In some embodiments of the compound of formula I, the compound is a fluorinated analog of CBDA ester. In another embodiment, the fluorinated analog of CBDA ester is a compound of formula (IV):

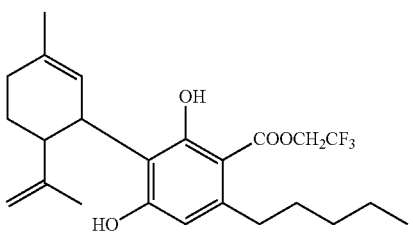

(IV)

or a pharmaceutically acceptable salt thereof.

In some embodiments of the compound of formula (III), the fluorinated analog of CBDA ester is the compound of formula (IVa):

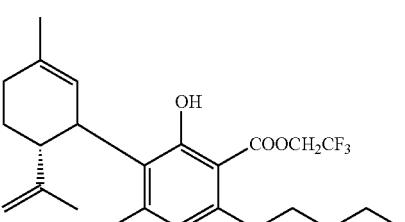

(IVa)

or a pharmaceutically acceptable salt thereof.

In some embodiments of the compound of formula (III), the fluorinated analog of CBDA ester is the compound of formula (IVb):

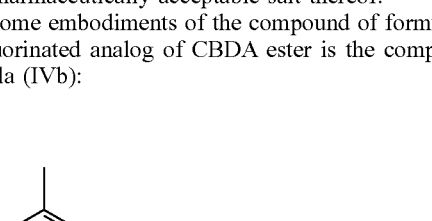

(IVb)

or a pharmaceutically acceptable salt thereof.

In some embodiments of formula (I), the compound is of formula (V):

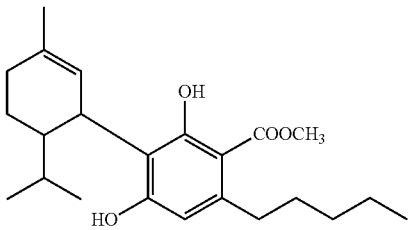

(V)

or a pharmaceutically acceptable salt thereof.

In some embodiments of formula (V), the compound is of formula (Va):

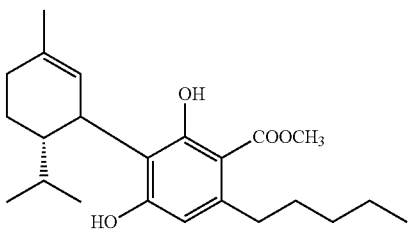

(Va)

or a pharmaceutically acceptable salt thereof. In another embodiment, the compound of formula (V) is EPM-302.

Aspects of the present disclosure include compounds (e.g., as described herein), salts thereof (e.g., pharmaceutically acceptable salts), and/or solvate or hydrate forms thereof. It will be appreciated that all permutations of salts, solvates and hydrates are meant to be encompassed by the present disclosure. In some embodiments, the subject compounds are provided in the form of pharmaceutically acceptable salts.

Pharmaceutical Compositions

The present disclosure provides pharmaceutical compositions including a cannabinoid acid ester compound (e.g., as described herein, such as a compound of any one of formulae (I)-(Va)), and a pharmaceutically acceptable excipient. The subject pharmaceutical compositions find use in a variety of therapeutic indications and other uses (e.g., as described herein). In some embodiments, the pharmaceutical composition includes a cannabinoid acid ester compound of formula (I):

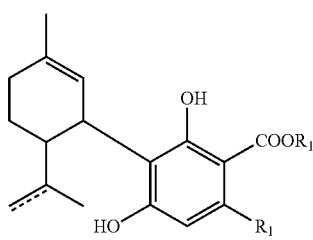

(I)

wherein $R_1$ and $R_2$ are independently selected from $C_1$-$C_{10}$ alkyl, substituted $C_1$-$C_{10}$ alkyl, $C_2$-$C_{10}$ alkenyl, substituted $C_2$-$C_{10}$ alkenyl, $C_2$-$C_{10}$ alkynyl, and substituted $C_2$-$C_{10}$ alkynyl, or a pharmaceutically acceptable salt thereof.

In some embodiments of the composition, $R_1$ is $C_1$-$C_6$ alkyl or substituted $C_1$-$C_6$ alkyl. In some embodiments of the composition, $R_1$ is selected from methyl, ethyl, propyl, butyl, and pentyl. In some embodiments of the composition, $R_1$ is methyl.

In some embodiments of the composition, $R_2$ is $C_1$-$C_{10}$ alkyl, or substituted $C_1$-$C_{10}$ alkyl. In some embodiments of the composition, $R_2$ is $C_{2-6}$ alkyl. In some embodiments of the composition, $R_2$ is pentyl.

In some embodiments of the composition, the compound of formula (I) is CBDA-Me of formula (II):

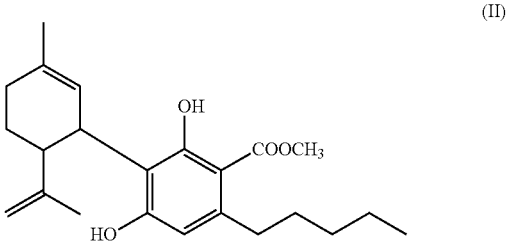 [SMILES: C=C(C)C1CCC(C)=CC1c1c(O)cc(CCCCC)c(C(=O)OC)c1O]

(II)

or a pharmaceutical salt thereof.

In some embodiments of the composition, the CBDA-Me is of formula (IIa):

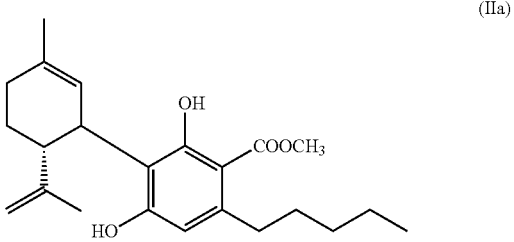 [SMILES: C=C(C)[C@@H]1CCC(C)=CC1c1c(O)cc(CCCCC)c(C(=O)OC)c1O]

(IIa)

or a pharmaceutically acceptable salt thereof.

In some embodiments of the composition, the CBDA-Me is of formula (IIa):

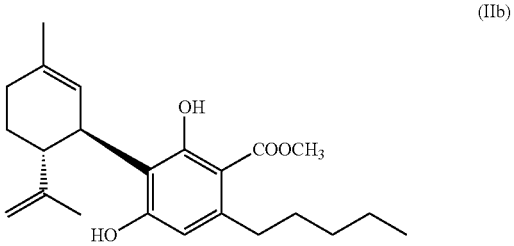 [SMILES: C=C(C)[C@@H]1CCC(C)=C[C@H]1c1c(O)cc(CCCCC)c(C(=O)OC)c1O]

(IIb)

or a pharmaceutically acceptable salt thereof.

In some embodiments of the pharmaceutical composition, the CBDA-Me compound is selected from an enantiomerically pure CBDA-Me, a stereoisomeric mixture of CBDA-Me, a diastereomeric mixture of CBDA-Me, a salt thereof, a deuterated analog thereof, a fluorinated analog thereof, and a combination thereof.

In some embodiments of the composition, the compound of formula (I) is the compound of formula (V):

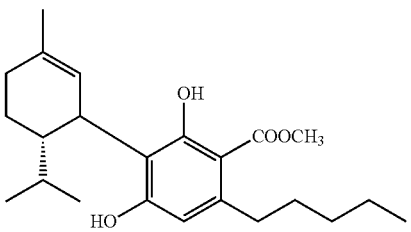

(V)

or a pharmaceutically acceptable salt thereof. In another embodiment, the compound of formula (V) is EPM-302.

According to some embodiments, the pharmaceutically acceptable excipient is an aqueous solution or carrier. In some embodiments the aqueous solution is a buffer having physiological or near-physiological pH, such as phosphate buffered saline (PBS). In some embodiments, the pharmaceutically acceptable excipient is selected from emulsifiers, buffering agents, pH adjusting agents, tonicity modifiers, preservatives, antioxidants, stabilizers, and a combination thereof. Exemplary excipients, additives and additional components of the subject pharmaceutical compositions are described in further detail below.

The subject pharmaceutical composition can further include one or more additional cannabinoid compounds. The additional cannabinoid compound can be an isolated compound, or part of a complex mixture. The additional cannabinoid compound can be part of a crude component or composition ingredient, or a purified sample.

In some embodiments, the one or more additional cannabinoid compounds that are included into a pharmaceutical composition are independently comprised in one or more cannabis plant extracts. The cannabis plant extracts can be obtained from any convenient source. In some embodiments, the cannabis plant extracts are produced from a plant strain selected from Cannabis sativa, Cannabis indica, Cannabis ruderalis, a hybrid strain, a strain with a high concentration of cannabidiol (CBD), a strain with a high concentration of tetrahydrocannabinol (THC), and a combination thereof.

In some embodiments, the one or more cannabis plant extracts comprise a cannabinoid compound selected from cannabidiol (CBD), tetrahydrocannabinol (THC), cannabinol (CBN), cannabigerol (CBG), cannabichromene (CBC), acids thereof, esters of the acids thereof, and combinations thereof.

In some embodiments, the one or more additional cannabinoid compounds are independently selected from cannabidiol (CBD), cannbigerol (CBG), Δ8-tetrahydrocannabinol (Δ8-THC), Δ9-tetrahydrocannabinol (Δ9-THC), cannabinol (CBN), Δ9(11)-tetrahydrocannabinol (exo-THC), cannabichromene (CBC), tetrahydrocannabinol-C3 (THC-C3), tetrahydrocannabinol-C4 (THC-C4), tetrahydrocannabinol-C7 (THC-C7), and esters thereof, stereoisomers thereof, deuterated analogs thereof, fluorinated analogs thereof, and combinations thereof.

In some embodiments, the one or more cannabis plant extracts that are incorporated into a pharmaceutical composition include about 1% (w/w) or more of CBD, such as about 2% (w/w) or more, about 3% (w/w) or more, about 4% (w/w) or more, about 5% (w/w) or more, about 6% (w/w) or more, about 7% (w/w) or more, about 8% (w/w) or more, about 9% (w/w) or more, about 10% (w/w), about 15% (w/w), about 20% (w/w) or more, or about 25% (w/w) or more CBD. In certain embodiments, the one or more cannabis plant extracts comprise about 30% (w/w) or less of CBD.

In some embodiments, the one or more cannabis plant extracts comprise about 1% (w/w) or more of THC, such as about 2% (w/w) or more, about 3% (w/w) or more, about 4% (w/w) or more, about 5% (w/w) or more, about 6% (w/w) or more, about 7% (w/w) or more, about 8% (w/w) or more, about 9% (w/w) or more, about 10% (w/w), about 15% (w/w), about 20% (w/w) or more, or about 25% (w/w) or more THC. In certain embodiments, the one or more cannabis plant extracts comprise about 30% (w/w) or less of THC.

In some embodiments, the one or more cannabis plant extracts comprising the one or more additional cannabinoid compounds are produced by extraction from a cannabis plant with a suitable solvent, or a combination of solvents. In some embodiments, the solvent is a pharmaceutically acceptable solvent, for example but not limited to, a non-toxic solvent that is suitable for administration to a mammal with no unacceptable adverse effects. The solvent may be an aqueous or non-aqueous solvent.

In some embodiments, the solvent for extraction is a polar solvent, a hydrocarbon solvent, an alcohol solvent, carbon dioxide, an oil, or a combination thereof.

In some embodiments, the solvent for extraction is a polar solvent.

In some embodiments, the solvent for extraction is polyethylene glycol or propylene glycol.

In some embodiments, the polar solvent for extraction comprises tetrahydrofuran (THF), dichloromethane (DCM), ethyl acetate (EtOAc), methanol, ethanol, propanol, isopropanol, butanol, tert-butanol, or dimethyl sulfoxide (DMSO).

In some embodiments, the solvent is an alcohol solvent. In some embodiments, the alcohol solvent is ethanol.

In some embodiments, the solvent for extraction is a hydrocarbon solvent comprising pentane, hexane, n-hexane, xylene, toluene, or benzene.

In some embodiments, the solvent for extraction is an oil comprising copaiba oil, vegetable oil, olive oil, sesame oil, coconut oil, avocado oil, peanut oil, canola oil, cottonseed oil, soybean oil, safflower oil, sunflower oil, castor oil, corn oil, palm oil, poppy seed oil, or walnut oil. In another embodiment, the pharmaceutical composition comprises copaiba oil.

In some embodiments, the pharmaceutical composition comprises 1% to 20% (w/w) a cannabidiolic acid ester compound and 50% to 90% vegetable oil.

In some embodiments, the pharmaceutical composition comprises 1% to 10% (w/w) of the cannabidiolic acid ester compound of formula (I).

In some embodiments, the pharmaceutical composition comprises:
1% to 10% CBDA-Me;
20% to 60% alcohol; and
0% to 35% propylene glycol.

In some embodiments, the pharmaceutical composition further comprises 5% to 20% polyethylene glycol.

In some embodiments, the pharmaceutical composition comprises:
2% to 10% CBDA-Me;
30% to 60% alcohol; and
a combination of propylene glycol and polyethylene glycol.

In some embodiments, the pharmaceutical composition comprises a combination of cannabinoids, a pharmaceutical carrier, a co-solvent, a penetration enhancer, and an emulsifier. In another embodiment, the pharmaceutical composition comprises about 5% to 80% of the pharmaceutical carrier, about 50% of the co-solvent, about 1% to 5% of the penetration enhancer, about 0.1% to 20% of the emulsifier, and about 0.001% to 10% of the combination of cannabinoids.

In some embodiments, the pharmaceutical composition comprises about 5% to 60% of anhydrous lanolin, about 5% to 80% of olive oil, about 0.2% to 20% polysorbate, about 0.001% to 10% of the combination of cannabinoids, and jojoba oil.

In some embodiments, the pharmaceutical composition comprises about 5% to 60% of anhydrous lanolin, about 5% to 80% of white petrolatum, about 5% to 80% of white olive oil, about 0.2% to 20% polysorbate 80, and about 0.001% to 10% of the combination of cannabinoids.

In some embodiments, the pharmaceutical composition comprises about 0% to 50% of ethanol, about 5% to 30% of glycerol, about 10% to 90% of propylene glycol, and about 0.2% to 25% of cyclosporine A powder.

In some embodiments, the ratio of the cannabinoid acid ester compound of formula (I) to additional cannabinoid compounds in the pharmaceutical composition is from 1.05:1 to 1,000:1. In another embodiment, the ratio of the cannabinoid acid ester compound of formula (I) to additional cannabinoid compounds in the pharmaceutical composition is from 1.05:1 to 5:1. In another embodiment, the ratio of the cannabinoid acid ester compound of formula (I) to additional cannabinoid compounds in the pharmaceutical composition is from 5:1 to 50:1. In another embodiment, the ratio of the cannabinoid acid ester compound of formula (I) to additional cannabinoid compounds in the pharmaceutical composition is from 50:1 to 500:1. In another embodiment, the ratio of the cannabinoid acid ester compound of formula (I) to additional cannabinoid compounds in the pharmaceutical composition is from 500:1 to 1,000:1.

In some embodiments, the pharmaceutical composition further comprises a lipid. The lipid can be triglyceride, fat, oil, fatty acid, or a mixture thereof.

In another embodiment, the lipid is a phospholipid, preferably a naturally occurring phospholipid or a synthetic phospholipid. In another embodiment, the lipid is a naturally occurring phospholipid selected from soy lecithin, egg lecithin, hydrogenated soy lecithin, hydrogenated egg lecithin, and combinations thereof. In another embodiment, the lipid is a synthetic phospholipid selected from phosphocholines, phosphoethanolamines, phosphatidic acids, phosphoglycerols, phosphoserines, mixed chain phospholipids, lysophospholipids, pegylated phospholipids, and combinations thereof.

In some embodiments, the phospholipid may form micelles, emulsions, or liposomes. In some embodiments, the cannabidiolic acid ester compounds as described herein are provided in microencapsulation particles. Encapsulation may result in cannabinoids and other materials present in cannabinoid materials in liposomal capsule particles or other type of particles.

In some embodiments, microencapsulation or nanoencapsulation may increase cannabinoid bioavailability, thereby increasing cannabinoid efficacy after absorption through mucosal membrane. Microencapsulation or nanoencapsulation may result in particles of 20-40 nm in size. Microencapsulation or nanoencapsulation promotes dissolution of cannabinoid particles in an aqueous environment.

In some embodiments, the pharmaceutical composition comprises at least one micelle-forming compound selected from a polyoxyethylene ether, ester, or alcohol; an alkali metal alkyl sulfate, a bile acid, lecithin, hyaluronic acid, pharmaceutically acceptable salts of hyaluronic acid, octylphenoxypolyethoxyethanol, glycolic acid, lactic acid, chamomile extract, cucumber extract, oleic acid, linolenic acid, borage oil, evening of primrose oil, trihydroxy oxocholanylglycine, glycerin, poly glycerin, lysine, polylysine, triolein, salts thereof, and mixtures thereof. According to certain embodiments, the bile acids or bile acid salts are selected from the group consisting of chenodesoxycholic acid (CDCA), desoxycholic acid (DCA), lithocholic acid (LCA), taurodesoxycholic acid (TDCA), hyodeoxycholic acid (HDCA), taurocholic acid (TCA), glycocholic acid (GCA), and combinations thereof.

In some embodiments, the pharmaceutical composition further comprises triglyceride, fat, oil, fatty acid, or a mixture thereof. In some embodiments of the pharmaceutical composition, the composition further comprises cyclodextrin, electrolyte, vitamin, mineral, flavoring agent, or a combination thereof.

In some embodiments, the pharmaceutical composition further comprises cyclodextrin. In another embodiment, the cyclodextrin is selected from hydroxypropyl β-cyclodextrin, sulfobutylether β-cyclodextrin, and methyl β-cyclodextrin (MPCD).

In some embodiments, the pharmaceutically acceptable excipient is aqueous. In another embodiment, the pharmaceutical acceptable excipient is selected from a emulsifier, a buffering agent, a pH adjusting agent, a preservative, an antioxidant, a stabilizer, an electrolyte, a vitamin, a mineral, a flavoring agent, a solubilizing agent, a tonicity enhancing agent, a colorant, and a combination thereof.

In some embodiments, the antioxidant is glycine, α-tocopherol or ascorbate, butylated hydroxyanisole (BHA), butylated hydroxytoluene (BHT), or a mixture thereof.

In some embodiments, the vitamin is selected from is vitamin A, vitamin C, vitamin D (e.g. vitamin D1, D2, D3, D4, and/or D5), vitamin E, vitamin B1 (thiamine), vitamin B2 (e.g. riboflavin), vitamin B3 (e.g. niacin or niacinamide), vitamin B5 (pantothenic acid), vitamin D6 (pyridoxine), vitamin D7 (biotin), vitamin B9 (e.g. folate or folic acid), vitamin B12 (cobalamin), vitamin K (e.g. K1, K2, K3, K4, and K5), and choline.

In some embodiments, the emulsifier is selected from polyvinyl alcohol (PVA), polysorbate, polyethylene glycols, polyoxyethylene-polyoxypropylene block copolymers, polyglycerin fatty acid esters, sorbitan fatty acid ester, polyoxyethylen sorbitan fatty acid ester, polyethylene glycol fatty acid ester, polyoxyethylene alkyl ether, polyoxyethylene castor oil, hardened castor oil, hydrogenated castor oil, sodium gluconate, acrylates, $C_{10-30}$ alkyl acrylate crosspolymer, sodium carboxymethyl betaglucan, polyglyceryl-3 methylglucose distearate, cetearyl alcohol, cetyl alcohol, stearic acid, behenyl alcohol, butylene glycol, propylene glycol, xanthan gum, potassium cetyl phosphate, polyglyceryl-6 distearate jojoba esters, polyglyceryl-3-beeswax, PEG-800, laureth-7, $C_{13-14}$ isoparafin, polyisobutene, PEG-200 hydrogenated glyceryl palmate, cellulose gum, PEG-7 glyceryl cocoate, aluminum starch octenylsuccinate, and a combination thereof.

Solubilizing agent and emulsifiers can be used to improve the bioavailability of cannabidiolic acid ester compounds as described herein. Bioavailability refers to the extent and rate at which the active moiety (drug or metabolite) enters systemic circulation, thereby accessing the site of action. Bioavailability for a given formulation provides an estimate of the relative fraction of the orally administered dose that is absorbed into the systemic circulation. Low bioavailability is most common with oral dosage forms of poorly water-soluble, slowly absorbed drugs. Insufficient time for absorption in the gastrointestinal tract is a common cause of low bioavailability. If the drug does not dissolve readily or cannot penetrate the epithelial membrane (e.g., if it is highly ionized and polar), time at the absorption site may be insufficient. Orally administered drugs must pass through the intestinal wall and then the portal circulation to the liver, both of which are common sites of first-pass metabolism (metabolism that occurs before a drug reaches systemic circulation).

In some embodiments, the bioavailability enhancing agent is an edible oil or fat, a protective colloid, or both a protective colloid and an edible oil or fat. In another embodiment, the bioavailability enhancing agent is also a lipophilic active agent taste masking agent. In another embodiment, the bioavailability of the lipophilic active agent in a subject is at last about 2 times, 5 times, or 10 times greater than the bioavailability of the lipophilic active agent in the subject in the absence of the bioavailability enhancing agent.

In some embodiments, the tonicity enhancing agent comprises ionic and non-ionic agents, such as alkali metal or alkaline earth metal halides, urea, glycerol, sorbitol, mannitol, propylene glycol, and dextrose.

In some embodiments, the preservative is comprises chloride, benzoxonium chloride, thiomersal, phenylmercuric nitrate, phenylmercuric acetate, phenylmercuric borate, methylparaben, propylparaben, chlorobutanol, benzyl alcohol, phenyl alcohol, chlorohexidine, or polyhexamethylene biguanide.

In some embodiments, the flavoring agent comprises sweeteners such as sucralose and synthetic flavor oils and flavoring aromatics, natural oils, extracts from plants, leaves, flowers, and fruits, and combinations thereof. Exemplary flavoring agents include cinnamon oils, oil of wintergreen, peppermint oils, clover oil, hay oil, anise oil, eucalyptus, vanilla, citrus oil such as lemon oil, orange oil, grape and grapefruit oil, and fruit essences including apple, peach, pear, strawberry, raspberry, cherry, plum, pineapple, and apricot.

In some embodiments, the colorant comprises alumina (dried aluminum hydroxide), annatto extract, calcium carbonate, canthaxanthin, caramel, $\beta$-carotene, cochineal extract, carmine, potassium sodium copper chlorophyllin (chlorophyllin copper complex), dihydroxyacetone, bismuth oxychloride, synthetic iron oxide, ferric ammonium ferrocyanide, ferric ferrocyanide, chromium hydroxide green, chromium oxide greens, guanine, mica-based pearlescent pigments, pyrophyllite, mica, dentifrices, talc, titanium dioxide, aluminum powder, bronze powder, copper powder, and zinc oxide.

In some embodiments, the pH-adjusting agent is an organic or mineral acid.

In some embodiment of the pharmaceutical composition, the composition is formulated for administration orally, topically, systemically, intravenously, subcutaneously, nasally, rectally, intramuscularly, intraperitoneally, transdermally, intra-arterially, intranasally, vaginally, by vaporization, or by inhalation.

In some embodiment, the pharmaceutical composition is in a form selected from liquid, gel, cream, ointment, lotion, paste, tablet, pill, capsule, pellets, granules, powder, a wafer, coated or uncoated beads, lozenge, sachet, cachet, elixir, an osmotic pump, a depot system, an iontophoretic system, a patch, suspension, dispersion, emulsion, solution, syrup, aerosol, oil, and suppository.

In some embodiment, the pharmaceutical composition is formulated for oral administration. In some embodiments, the composition is formulated as a tablet or capsule. In some embodiments, the orally administered formulation is optionally coated or scored and may be formulated so as to provide sustained, delayed, or controlled release of the active ingredient therein.

In some embodiments, the formulation suitable for oral administration comprises a mixture of sodium carboxymethylcellulose and hydroxypropyl-cellulose or methyl cellulose as the film-forming agents. The ratio of sodium carboxymethylcellulose to hydroxypropyl cellulose (or methylcellulose) used to make the formulation is chosen to yield the desired dissolution time and mouth-feel for the film and to further impart acceptable product handling characteristics. The formulation may include from about 5 wt % to 75 wt %, particularly from about 15 to 50 wt %, based on the weight of the formulation of sodium carboxymethylcellulose and hydroxypropyl-cellulose (or methylcellulose). Pectin may also be combined with carboxymethylcellulose and hydroxypropyl-cellulose or methyl cellulose in an amount ranging from about 4 to 25 wt %.

In some embodiment, the pharmaceutical composition is formulated in the form of a liquid at a temperature in the range of 4° C. to 37° C.

In some embodiments, the pharmaceutical composition is formulated in the form of a gel at physiological temperature. In another embodiment, the pharmaceutical composition is a gel, wherein the cannabinoid component or salt thereof is entrapped in a gel matrix. In another embodiment, the gel compositions may comprise an oi-in water (o/w) emulsion.

In some embodiments, the pharmaceutical composition is formulated for slow release of cannabinoid acid ester. In another embodiment, the pharmaceutical composition further comprises a release retarding agent or a mixture of release retarding agents. In another embodiment, the pharmaceutical composition is at least partly coated by an enteric-coating agent.

In some embodiments of the pharmaceutical composition, the composition further comprises emollient-based cream, keratolytic agent, coal tar ointment, steroid, vitamin D analog, anthralin, retinoid tazarotene, or a combination thereof.

In another embodiment, the keratolytic agent is formulated with urea or salicylic acid.

In some embodiment of the pharmaceutical composition, the composition further comprises anti-histamine, anesthesia agent, terpene, or a combination thereof.

In some embodiments, the pharmaceutical composition further a viscosity agent.

In some embodiments, the viscosity agent is a polysaccharide, a polysaccharide salt, or a combination thereof. In another embodiment, the polysaccharide is selected from hyaluronic acid (HA), chitosan, cellulose derivative, chondroitin sulfate, keratan, heparin, xanthans, galactomann, alginates, and a combination thereof.

In some embodiments, the viscosity agent is present in the composition at a concentration in the range of 1 mg/ml to 100 mg/ml. In another embodiment, the viscosity agent is present in the composition at a concentration in the range of 10 mg/ml to 25 mg/ml.

In some embodiments, the viscosity of the pharmaceutical composition is up to 2,000 centipoises at 20° C. In another embodiment, the viscosity of the pharmaceutical composition is up to 2,000 centipoises at 20° C. In another embodiment, the viscosity of the pharmaceutical composition is up to 1,800 centipoises at 20° C. In another embodiment, the viscosity of the pharmaceutical composition is up to 1,600 centipoises at 20° C. In another embodiment, the viscosity of the pharmaceutical composition is up to 1,500 centipoises at 20° C. In another embodiment, the viscosity of the pharmaceutical composition is up to 2,000 centipoises at 20° C. In another embodiment, the viscosity of the pharmaceutical composition is up to 2,000 centipoises at 20° C.

In some embodiments, the viscosity of the pharmaceutical composition is less than 5,000 centipoises between 4° C. and 12° C. In another embodiment, the viscosity of the pharmaceutical composition is less than 500 centipoises between 4° C. and 12° C.

In some embodiments, the viscosity of the pharmaceutical composition is more than 500,000 centipoises at 37° C. In another embodiment, the viscosity of the pharmaceutical composition is more than $1 \times 10^3$ centipoises at 37° C. In another embodiment, the viscosity of the pharmaceutical composition is more than $3.5 \times 10^3$ at 37° C.

In some embodiments, the pharmaceutical composition comprises at least one physiologically acceptable film forming agent. In some embodiments, the physiologically acceptable film forming agent is selected from pullulan, methyl cellulose, ethyl cellulose, sodium carboxymethyl cellulose, hydroxypropylmethyl cellulose, hydroxyethyl cellulose, hydroxypropyl cellulose, carboxymethyl cellulose, polyvinyl pyrrolidone, methacrylic acid polymers, methacrylic acid copolymers, acrylic acid polymers, acrylic acid copolymers, polyacrylamides, polyalkylene oxides, carrageenan, polyvinyl alcohol, sodium alginate, polyethylene glycol, polyacrylic acid, glycolide, polylactide, methylmethacrylate copolymer, carboxyvinyl polymer, amylose, high amylose starch, hydroxypropylated high amylose starch, alginic acid, pea starch, dextrin, pectin, chitin, chitosan, levan, elsinan and mixtures thereof. Secondary film forming agents may be added to the formulation to optimize wafer characteristics such as tensile strength, stability, flexibility and brittleness including agents such xanthan gum, tragacanth gum, guar gum, locust bean gum, acacia gum, arabic gum, collagen, gelatin, zein, gluten, soy protein isolate, whey protein isolate, casein and a mixture thereof.

In some embodiments, the composition further comprises platelet-rich plasma (PRP) or platelet-rich fibrin (PRF).

In some embodiments, the PRP is selected from leukocyte-rich PRP (L-PRP), leukocyte reduced PRP and a combination thereof.

In some embodiments, the PRF is selected from leukocyte platelet-rich fibrin, pure platelet-rich fibrin, and a combination thereof.

In some embodiments, the pharmaceutical composition comprises 10% (w/w) or less of the cannabidiolic acid ester compound of formula (I). In another embodiment, the pharmaceutical composition comprises 7% (w/w) or less of the cannabidiolic acid ester compound of formula (I). In another embodiment, the pharmaceutical composition comprises 5% (w/w) or less of the cannabidiolic acid ester compound of formula (I). In another embodiment, the pharmaceutical composition comprises 1% (w/w) or less of the cannabidiolic acid ester compound of formula (I). In another embodiment, the pharmaceutical composition comprises 0.5% (w/w/) or less of the cannabidiolic acid ester compound of formula (I). In another embodiment, the pharmaceutical composition comprises 0.1% (w/w) or less of cannabidiolic acid ester compound of formula (I). In another embodiment, the pharmaceutical composition comprises 0.01% (w/w) or less of cannabidiolic acid ester compound of formula (I). In another embodiment, the pharmaceutical composition comprises 0.001% (w/w) or less of cannabidiolic acid ester compound of formula (I).

Methods of Treatment

Aspects of the present disclosure include methods of treating a target disease or disorder (e.g., as described herein) that include administration of a subject cannabinoid acid ester compound (e.g., as described herein) or subject pharmaceutical composition (e.g., as described herein) to a subject in need thereof.

Administration of the subject cannabinoid acid ester compound (e.g., as described herein) or subject pharmaceutical composition can be performed via any convenient methods depending on the target indication and subject. In some embodiments, the pharmaceutical composition is administered orally. In another embodiment, the composition is administered topically. In another embodiment, the pharmaceutical composition is administered systemically. In another embodiment, the pharmaceutical composition is administered intravenously. In another embodiment, the pharmaceutical composition is administered subcutaneously. In another embodiment, the pharmaceutical composition is administered inhalation. In another embodiment, the pharmaceutical composition is administered vaporization. In another embodiment, the pharmaceutical composition is administered nasally. In another embodiment, the pharmaceutical composition is administered rectally. In another embodiment, the pharmaceutical composition is administered topically. In another embodiment, the pharmaceutical composition is administered intramuscularly. In another embodiment, the pharmaceutical composition is administered intraperitoneally. In another embodiment, the pharmaceutical composition is administered transdermally. In another embodiment, the pharmaceutical composition is administered intra-arterially. In another embodiment, the pharmaceutical composition is administered intranasally. In another embodiment, the pharmaceutical composition is administered vaginally. In some embodiments, the pharmaceutical composition is embedded in an article.

It is understood that the amount of compound or composition administered will be determined by a physician, according to various parameters including the chosen route of administration, the age, weight, and the severity of the subject's symptoms for the target disease.

The dosage and regimen will vary depending on the target indication and subject being treated. In some embodiments, the pharmaceutical composition is administered once a day, twice a day, three times a day, or four times a day. In some embodiments, the pharmaceutical composition is administered once a week, once in two weeks, once in three weeks, or once in a month. In some embodiments, the pharmaceutical composition is administered once in two months, once in three months, once in four months, once in five months, or once in six months.

In some embodiments, the pharmaceutical composition is administered at least 30 minutes before ingestion of food. In another embodiment, the pharmaceutical composition is administered at least one hour, two hours, or three hours before ingestion of food.

In some embodiments, the pharmaceutical composition is administered for a period of greater than a week. In some embodiments, the pharmaceutical composition is administered for a period of greater than four weeks. In some embodiments, the pharmaceutical composition is administered for a period greater than two months. In another embodiment, the pharmaceutical composition is administered for a period greater than 3, 4, 5, or 6 months.

In some embodiments, the effective dose of cannabidiolic acid ester ranges from 0.1 to 500 mg/kg/day of body weight, from 1 to 250 mg/kg/day of body weight, from 2 to 100 mg/kg/day of body weight, or from 5 to 50 mg/kg/day, and may be in single dose or divided throughout the day.

In some embodiments, the pharmaceutical composition is administered in a unit dosage form of approximately 0.02 g/kg/day to approximately 0.5 g/kg/day. In another embodiment, the unit dosage form is administered with food at any time of the day, without food at any time of the day, or with food after an overnight fast (e.g. with breakfast).

In some embodiments, the pharmaceutical composition is administered in combination with one or more additional therapeutic agents.

In some embodiments, the pharmaceutical composition may include ingredients in additional to the excipients described herein.

In some embodiments, the pharmaceutical composition is in a dosage unit. In some embodiments, the dosage unit comprises the active pharmaceutical ingredient as described herein and one or more additional therapeutic agents. In some embodiments, the one or more therapeutic agents of the dosage unit optionally exist in an extended or controlled release formulation. In some embodiments, the cannabinoid compounds as described herein may exist in a controlled release formulation or extended release formulation in the same dosage unit with another agent that may or may not be in either a controlled release or extended release formulation. In some embodiments, the unit dosage comprises one or more therapeutic agents as described herein formulated for immediate release and one or more other therapeutic agents as described herein formulated for controlled or extended release.

In some embodiments, the pharmaceutical composition comprises a unit dosage form of at least about 20 mg of cannabinoid acid ester or a mixture of cannabinoids comprising cannabinoid acid ester. In another embodiment, the unit dosage form comprises about 20 mg to about 2,000 mg of cannabinoid acid ester or a mixture of cannabinoids comprising cannabinoid acid ester. In some embodiments, the pharmaceutical composition comprises a unit dosage form of at least about 20 mg of cannbidiolic acid ester or a mixture of cannabinoids comprising cannabidiolic acid ester. In another embodiment, the unit dosage form comprises about 20 mg to about 2,000 mg of cannabidiolic acid ester or a mixture of cannabinoids comprising cannabidiolic acid ester. In certain embodiments, the unit dosage form comprises about 50 mg, 100 mg, about 200 mg, about 300 mg, about 400 mg, about 500 mg, about 600, about 700 mg, about 800 mg, about 900 mg, or about 1000 mg of cannabidiolic acid ester or a mixture of cannabinoids comprising cannabidiolic acid ester.

Further aspects of the methods of using the subject cannabinoid compounds and pharmaceutical compositions comprising the same are discussed below.

Joint Disease or Dysfunction

Osteoarthritis (OA) is the most common form of arthritis. OA is a type of joint disease that results from breakdown of joint cartilage and underlying bone and can occur after injury or surgical intervention. Chronic-inflammatory-joint conditions drives catabolic metabolism and many downstream events that lead to osteoarthritis. The associated chronic pain creates abnormal muscle recruitment and gait patterns, leading to biomechanical overload of joint surfaces and associated tissues. Oral non-steroidal anti-inflammatory drugs (NSAIDs) control joint pain but prolonged usage puts patients at risks of cardiovascular, hepatic, renal, and gastrointestinal complications. Intra-articular injection of drugs combined with sustained release carrier represents a more practical and safe alternative than daily oral NSAIDs, in particular if a long pharmacodynamic effect is achieved.

Aspects of the present disclosure include methods of treating a joint disease or dysfunction that include administration to a subject a pharmaceutical composition including a cannabinoid acid ester compound, e.g., as described herein. The subject may have a joint disease or dysfunction. In some embodiments, the joint disease or dysfunction is an inflammatory disease.

In some embodiments, the joint disease or dysfunction is joint inflammation or joint degeneration. In some embodiments of the method, the joint disease is osteoarthritis.

In some embodiments of the method, the pharmaceutical composition is administered in a therapeutically effective amount to a subject. The pharmaceutical composition can be administered to the subject via any convenient methods.

In some embodiments, the administration is intra-articular, and the pharmaceutical composition is formulated for intra-articular administration. In another embodiment, the intra-articular administration is by injection. The term "intra-articular" refers to situated within, occurring within, or administered by entry into the joint.

It is disclosed herein for the first time that pharmaceutical compositions comprising a cannabinoid acid ester compound, such as CBDA-ME, can achieve efficacy in the subject methods of treating joint disease or dysfunction. The pharmaceutical composition can include a viscosity agent with the cannabinoid acid ester compound to achieve improved efficacy.

Examples 5-6 of the experimental section described the results of studies of CBDA-Me in a rat meniscectomy model of osteoarthritis. It was shown that treating the rats with EPM-301 as compared with no therapy, resolved the surgery induced incapacitance.

According to specific embodiments, the viscosity agent is selected from hyaluronic acid, and chitosan and the combination with the cannabinoid acid ester compound in a subject pharmaceutical composition achieves equal or even higher therapeutic efficacy in treating joint pain and/or function as compared to known injectable dosage forms of hyaluronic acid, or chitosan. In additional embodiments, the subject compositions further comprises platelet rich plasma or platelet rich fibrin, and optionally isolated fibrin(ogen) or other blood derived fractions (either autologous or allogeneic or xenogeneic) which may enhance the therapeutic activity of the composition in the subject methods.

In some embodiments, the pharmaceutical composition for use in treating a joint disease or dysfunction comprises a cannabinoid component, wherein the cannabinoid component comprises:

a cannabidiolic acid methyl ester (CBDA-Me) alone or in combination with one or more additional cannabinoid compounds; wherein CBDA-Me comprises more than 50% of the total weight of cannabinoids in the combination;

a solubilizing agent;

a viscosity agent; and a pharmaceutically acceptable carrier.

In some embodiments, the pharmaceutical composition for use in treating a joint disease or dysfunction comprises:

a cannabinoid component, wherein the cannabinoid component comprises a cannabidiolic acid methyl ester (CBDA-Me) alone or in combination with one or more additional cannabinoid compounds; wherein CBDA-Me comprises more than 51% of the total weight of cannabinoids in the combination;

a solubilizing agent; and
a viscosity agent.

In some embodiments, the pharmaceutical composition further comprises platelet rich plasma (PRP) or platelet rich fibrin (PRF). In some embodiments the platelet-rich-plasma (PRP) is selected from leukocyte-rich PRP (L-PRP), leukocyte reduced PRP, leukocyte platelet-rich fibrin or pure platelet-rich fibrin (PRF), and a combination thereof.

In some embodiments of the method, the pharmaceutical composition is administered once a week, once in two weeks, once in three weeks, or once in a month. In another embodiment, the pharmaceutical composition is administered once in two months, once in three month, once in four months, once in five months, or once in six months. In some embodiments of the method, the pharmaceutical composition is capable of treating all joints. In a preferred embodiment, the joint to be treated is the knee of the human subject. In another preferred embodiment, the joint to be treated is the hip of a dog. In another embodiment, the joint to be treated is selected from carpus, fetlock, and hock of a horse.

In some embodiments of the method of treating a joint disease or dysfunction, the pharmaceutical composition is administered in combination with one or more additional therapeutic agents for treating a joint disease or dysfunction.

Skin Diseases and Disorders

Skin diseases and disorders encompass numerous skin conditions ranging in severity from psoriasis, sever dermatitis, sever dry skin, bacterial infections, acne, rosacea, scleroderma, atopic dermatitis, etc., to less sever conditions, such as allergic reactions or reactions to insect bites. Skin disorders can be divide to inflammatory and non-inflammatory conditions. Important types of skin disorders that are due to impaired wound healing rather than predominantly inflammatory pathologies, are chronic sores or lesions such as diabetic skin ulcers or pressure sores. Inflammatory skin disease or disorders often result in benign hyperproliferative skin disorders, which are characterized by a higher than normal level of proliferation of epidermal cells known as keratinocytes, and by abnormal differentiation.

Psoriasis is a chronic inflammatory skin disease characterized by abnormal differentiation and hyperproliferation of the epidermis. Clinical symptoms include erythematous scaling plaques which are commonly present on the elbow, knees, and scalp. Flare-ups of psoriasis can occur randomly but have been known to follow period of physical and emotional stress, cutaneous trauma, infection, and as a reaction to certain compounds or medications, including β-adrenergic receptor antagonists, lithium, antimalarials, and systemic steroids.

One consideration in psoriasis therapy is the percent of body surface area involved. Patients with less than 15% body surface involvement can be treated with topical agents. Topical therapy for psoriasis includes emollient-based creams, keratolytic agents formulated with urea or salicylic acid, coal tar ointments, steroids, vitamin D and its analogs, anthralin and retinoid tazarotene. Undesirable side effects of therapy can include staining, irritation and allergic reactions.

Aspects of the present disclosure include methods of treating or at least ameliorating a skin disease or disorder using the subject compounds and pharmaceutical composition. The method can include administering a therapeutically effective amount of a pharmaceutical composition as described herein to a subject having a skin disease or disorder.

In some embodiments of the method, the skin disease or disorder is an inflammatory skin disease or disorder. In some embodiments, the inflammatory skin disease or disorder is selected from psoriasis, atopic dermatitis (AD), eczema, actinic keratosis, ichthyosis, pemphigus vulgaris, acne, Grover's disease (transient acantholytic dermatosis), keratoacanthoma, hidradenitis suppurativa, seborrheic keratosis, pityriasis lichenoid, alopecia areata, basal cell carcinoma, Bowen's disease, congenital erythropoietic porphyria, contact dermatitis, Darier's disease, dystrophic epidermolysis bullosa, pidermolysis bullosa simplex, erythropoietic protoporphyria, fungal infections of nails, herpes simplex, hidradenitis suppurativa, ichthyosis, impetigo, keloids, keratosis pilaris, lichen planus, lichen sclerosus, pemphigus vulgaris, plantar warts (verrucas), pityriasis lichenoides, polymorphic light eruption, pyoderma gangrenosum, rosacea, shingles, squamous cell carcinoma, Sweet's syndrome, and vitiligo. In another embodiment, the inflammatory skin disease is caused by microbial infection-induced dermatitis, solar dermatitis, atopic dermatitis, or allergic contact dermatitis. In some embodiments of the method, the inflammatory skin disease or disorder is psoriasis. In some embodiments of the method, the inflammatory skin disease or disorder is atopic dermatitis (AD).

In some embodiments of the method, the skin disorder is a diabetic skin disorder. In another embodiment, the diabetic skin disorder is chronic diabetic wounds.

In some embodiments of the method, the skin disease or disorder is epidermal hyperproliferation or dermal inflammation.

In some embodiments, the method reduces or at least alleviates the symptoms associated with a skin disease or disorder. In another embodiment, the method reduces pain associated with skin disease or disorder.

In some embodiments, the pharmaceutical composition is administered in a therapeutically effective amount to subject.

In some embodiments, the pharmaceutical composition is formulated for topical administration. In another embodiment, the pharmaceutical composition is formulated in a form selected from a cream, an ointment, a lotion, a paste, and a gel. In some embodiments, the pharmaceutical composition is formulated as a cream.

In some embodiments of the method, the pharmaceutical composition is administered once a day, twice a day, three times a day, or four times a day. In another embodiment, the pharmaceutical composition is administered once in two days in a week, once in three days in a week, once in four days in a week, or once in five days in a week.

In some embodiments, the pharmaceutical composition is administered topically in a therapeutically effective amount. In another embodiment, the therapeutically effective amount of the pharmaceutical composition is administered up to about four times a day. In another embodiment, the therapeutically effective amount of the pharmaceutical composition is administered twice a day. In another embodiment, the therapeutically effective amount of the pharmaceutical composition is administered twice daily at intervals of about 12 hours. In another embodiment, the therapeutically effective amount of the pharmaceutical composition is administered once a day.

In some embodiments of the method, the pharmaceutical composition is administered in combination with one or more additional therapeutic agents suitable for treating or preventing a skin disease or disorder.

Figure 6:
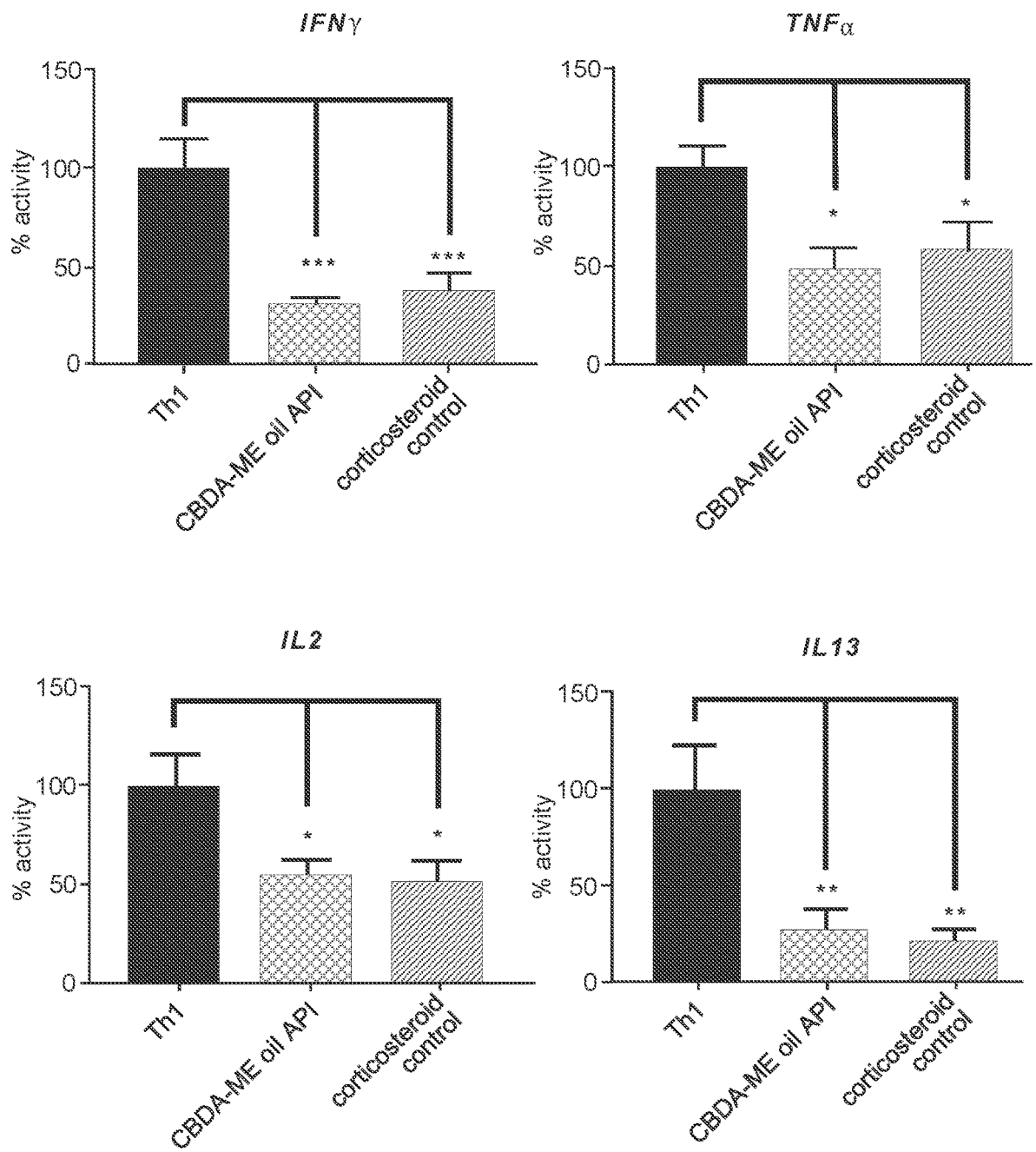
FIG. 6 shows the effect of CBDA-Me on suppression of inflammation in an ex vivo model of induced inflammation of human skin explants. The effect was examined on Th1 (chronic and acute AD) mediated inflammation. The anti-inflammatory effect was assessed using different biomarkers as indicated. Two donors, n=4 per donor (n=8 total replicates). Error bars represent SEM. Statistics are One-Way ANOVA to stimulated tissue $*p<0.05$, $*p<0.01$, $*p<0.001$, $*p<0.0001$.
Figure 7:
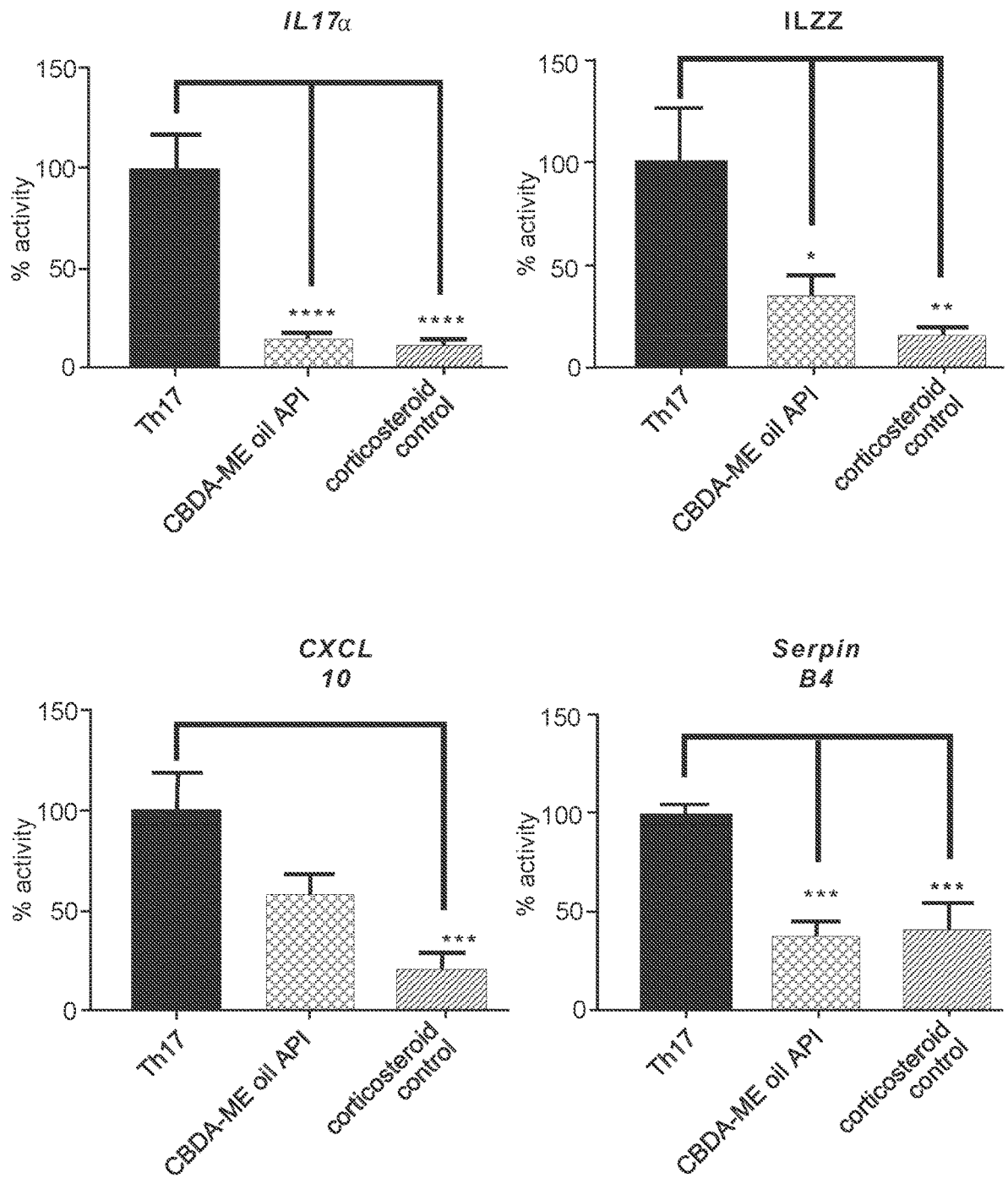
FIG. 7 shows the effect of CBDA-Me on suppression of inflammation in an ex vivo model of induced inflammation of human skin explants. The effect was examined on Th17 (psoriasis) mediated inflammation. The anti-inflammatory effect was assessed using different biomarkers as indicated. Two donors, n=4 per donor (n=8 total replicates). Error bars represent SEM. Statistics are One-Way ANOVA to stimulated tissue $*p<0.05$, $*p<0.01$, $*p<0.001$, $*p<0.0001$.

Examples 8-10 of the experimental section describe the preparation of an exemplary topical pharmaceutical composition including CBDA-Me, and assessment of activity in models of skin inflammatory disease. As shown in FIG. 6 and FIG. 7, CBDA-Me inhibits both Th1 (chronic and acute AD) and Th17 (psoriasis) mediated inflammation, in a degree at least comparable to that of a control corticosteroid formulation. The therapeutic potential for compositions including cannabinoid acid ester compounds such as CBDA-Me is unexpectedly similar in efficacy to corticosteroids without the potential for adverse effects.

Gastrointestinal Disease or Disorder

Gastrointestinal, or stomach disorders are very common and induce a significant amount of morbidity and suffering in the population. Gastrointestinal disorders are comprised of a variety of ailments including, inter alia, constipation, irritable bowel syndrome, diverticular disease, colon polyps, and colitis. Gastrointestinal disorders can result from various causes, including functional changes after surgery, inherited disorders, neurologic diseases, connective tissue disorders, metabolic abnormalities, and infections.

Aspects of the present disclosure include methods of treating a gastrointestinal disease or disorder using the subject compounds and pharmaceutical compositions. The method can include administering a therapeutically effective amount of the pharmaceutical composition as described herein to a subject having a gastrointestinal disease or disorder.

In some embodiments of the method, the gastrointestinal disease or disorder is selected from irritable bowel syndrome (IBS), inflammatory bowel disease (IBD), gastrointestinal motility disorders, constipation, functional gastrointestinal disorder, gastroesophageal reflux disease (GERD), duodenogastric influx, functional heartburn, dyspepsia, visceral pain, gastroparesis, Celiac disease, and chronic intestinal pseudo-obstruction.

In some embodiments of the method, the gastrointestinal disease is IBS. IBS symptoms are usually related to pain or discomfort generally felt in the center of the abdomen around or above the navel. Some examples of discomfort include fullness, early satiety, which is a feeling of fullness soon after starting to eat, bloating and nausea. Some IBS patients experience failure of the relaxation of the upper stomach following an ingestion of food, a condition known as abnormal gastric accommodation reflex. About half of the patients with these symptoms also have a sensitive or irritable stomach which causes sensations of discomfort when the stomach contains even small volumes.

According to some embodiments, administration of the pharmaceutical composition improves gastrointestinal function. According to certain embodiments, the pharmaceutical composition reduces abdominal pain. According to additional embodiments, the pharmaceutical composition improves mucosal healing, restores small intestine function, enhances fluid retention, and alleviates an array of associated disease symptoms including, but not limited to, malabsorption, diarrhea, nausea, vomiting, electrolyte imbalance, and dehydration.

According to some embodiments, the pharmaceutical composition reduces intestinal insufficiency. By "intestinal insufficiency" is meant a pathological state of the intestine, in particular of the small intestine, in which the absorption of nutriments is reduced relative to normal, the reduction in the absorption of nutriments being linked to a reduction in the number and/or functionality of intestinal cells capable of carrying out this absorption, this reduction in the number and/or functionality of intestinal cells being itself due either to a physical elimination of these cells (in particular by surgery or by radiation), or to a pathological dysfunction of these cells.

Intestinal insufficiency is also linked to ageing. Protein-energy malnutrition is highly frequent in the elderly in which approximately 40% of those aged over 70 years are affected. In a malnutrition situation, ageing is characterized by morphological and functional modifications of the small intestine; these changes can lead to malabsorption and aggravate the pre-existing malnutrition. Moreover, this malnutrition aggravates changes in the digestive system linked to age. The degradation of the nutritional state furthers the risks of infections.

According to some embodiments, the pharmaceutical composition is used for alleviation of short-bowel syndromes. short-bowel syndrome following an intestinal resection, in particular in the case of acute mesenteric ischemia, thrombosis of the superior mesenteric vein, volvulus of the small intestine and strangulated hernias, chronic intestinal pseudo-obstruction, radiation-damaged small intestine, Crohn's disease, abdominal traumatism; short-bowel syndrome results in particular from resections of the small intestine leaving a maximum of 1 meter of small intestine besides the duodenum; these resections lead in the immediate post-operative period to an intestinal insufficiency characterized by constant and major malabsorption, sometimes aggravated by gastric hypersecretion, which leads to the setting up of total parenteral nutrition, rapidly combined with continuous enteral nutrition, then to oral feeding; the adaptation of the remaining intestine is possible between 2 and 6 months after the procedure, but the improvement in the absorption capacities of the small intestine most often remains insufficient.

According to some embodiments, the gastrointestinal disease is gastrointestinal inflammatory disease. In some embodiments of the method, the gastrointestinal disease is IBD. IBD is a group of inflammatory conditions of the large intestine and small intestine. Symptoms of IBD are well known and include, without limitation, diarrhea, fever (e.g., low-grade fever), abdominal pain and cramping, blood in the stool (hematochezia), bleeding ulcers, bloating, bowel obstruction, unintended weight loss, and anemia. According to some embodiments, forms of inflammatory bowel disease include Crohn's disease, ulcerates colitis, indeterminate colitis, and/or chemotherapy-induced colitis. Ulcerative colitis is an inflammatory disease of the large intestine. In ulcerative colitis, the inner lining, or mucosa, of the intestine becomes inflamed (meaning the lining of the intestinal wall reddens and swells) and develops ulcers meaning an open, painful wound. Crohn's disease differs from ulcerative colitis in the areas of the bowel it involves, it most commonly affects the last part of the small intestine and parts of the large intestine. However, Crohn's disease isn't limited to these areas and can attack any part of the digestive tract. The treatment of moderate to severe IBD poses significant challenges to treating physicians because conventional therapy with corticosteroids and immunomodulator therapy (e.g., azathioprine, and methotrexate) is associated with side effects and intolerance and has not shown proven benefit in maintenance therapy (steroids). Monoclonal antibodies targeting tumor necrosis factor alpha (TNFα), such as infliximab (a chimeric antibody) and adalimumab (a fully human antibody), are currently used in the management of Crohn's disease. Infliximab has also shown efficacy and has been approved for use in treating ulcerates colitis. However, approximately 10%-20% of patients with Crohn's disease are primary non-responders to anti TNF therapy. Other adverse events (AEs) associated with anti TNFs include elevated rates of bacterial infection, including tuberculosis, and, more rarely, lymphoma and demyelination. In addition, most patients do not achieve sustained steroid-free remission and mucosal healing, clinical outcomes that correlate with true disease modification.

According to some embodiments, the treatment reduces inflammatory mediators such as TNF-alpha and IL-6.

According to some embodiments, the gastrointestinal disease is a celiac disease. Celiac disease is a chronic enteropathy characterized by a food intolerance to gluten, and more particularly to proteins contained in certain cereals, such as gliadin, hordein or secalin; this disease occurs in genetically predisposed subjects; the intestinal mucosa of a patient suffering from celiac disease is the seat of an inflammatory process, partly of an immune nature, which causes in particular atrophy of the villi; the resultant intestinal insufficiency is characterized by intestinal malabsorption, which manifests itself in diarrhoea with steatorrhoea, emaciation and malnutrition; the biological consequences of malabsorption are in particular anaemia associated with an iron, folate or vitamin B12 deficiency, a deficit of vitamin K-dependent coagulation factors, hypoproteinaemia, hypoalbuminaemia, hypocalcaemia, hypomagnesaemia and zinc deficiency.

According to some embodiments, the gastrointestinal disorder is constipation. The constipation can be chronic constipation, idiopathic constipation, due to post-operative ileus, or caused by opiate use. Clinically accepted criteria that define constipation include the frequency of bowel movements, the consistency of feces and the ease of bowel movement. One common definition of constipation is less than three bowel movements per week. Other definitions include abnormally hard stools or defecation that requires excessive straining. Constipation may be idiopathic (functional constipation or slow transit constipation) or secondary to other causes including neurologic, metabolic or endocrine disorders. Constipation may also be the result of surgery (postoperative ileus) or due to the use of drugs such as analgesics (like opioids), antihypertensives, anticonvulsants, antidepressants, antispasmodics and antipsychotics.

In some embodiments of the method, the gastrointestinal disease is acute colitis or chronic colitis.

In some embodiments, the administration of the pharmaceutical composition improves gastrointestinal function. In another embodiment, the administration of the pharmaceutical composition reduces abdominal pain. In another embodiment, the administration of the pharmaceutical composition improves mucosal healing, restores small intestine function, and/or enhances fluid retention. In another embodiment, the administration of the pharmaceutical composition alleviates an array of associated disease symptoms selected from malabsorption, diarrhea, nausea, vomiting, electrolyte imbalance, and dehydration. In some embodiments, the method is a method of at least alleviating one or more symptoms of the Gastrointestinal disease or disorder.

In some embodiments, the administration of the pharmaceutical composition reduces intestinal insufficiency. In some embodiments, the administration of the pharmaceutical composition alleviates short-bowel syndromes.

In some embodiment, the administration of the pharmaceutical composition reduces inflammatory mediators such as TNF-alpha and IL-6. The levels of inflammatory mediators can be monitored (e.g., before, during and/or after administration) using any convenient methods. In some cases, a sample is obtained from the subject (e.g., a blood sample) and assayed for the inflammatory mediator of interest.

In some embodiments of the method, the pharmaceutical composition is administered in a therapeutically effective amount to a subject. The route of administration can be by any route and will be determined based on the physician and the patient. All other routes of administration of a therapeutically effective amount of an agent to treat an IBD patient are contemplated herein and include, without limitation, enteral (e.g., orally or rectally), or parenteral (e.g., intravenous, intrathecal, subcutaneous), or other routes (e.g., intranasal, intradermal, intravitreal, subcutaneous, transdermal, topical, intraperitoneal, intravaginal, and intramuscular). In some cases, administration is achieved orally.

According to some embodiments, the pharmaceutical composition is administered once a day, twice a week, once a week, once in two weeks, once in three weeks or once a month. According to yet further embodiments, the composition is administered once in two months, once in three months, once in four months, once in five months or once in six months.

According to some embodiments, the pharmaceutical composition is administered at least 30 minutes before ingestion of food. According to some embodiments, the pharmaceutical composition is administered at least an hour, or two hours before ingestion of food.

Examples 11-13 of the experimental section, and FIGS. 8-22, describe experiments and show results of the demonstrated therapeutic effects in vivo of exemplary cannabinoid acid ester compound CBDA-Me on inflammatory bowel disease (IBD) in acute colitis and chronic colitis mouse models. CBDA-Me exhibited improved therapeutic effects in both acute colitis and chronic colitis mouse models and was found to have superior activity as compared to CBD.

Uterine-Related Disorders

Endometriosis and menstrual pain are common disorders affecting one in every ten women at reproductive ages. Endometriosis is characterized by the presence of endometrium-like tissue, which normally forms the lining of the uterus, outside the uterus. The symptoms experienced by women who are afflicted with endometriosis include lower abdominal and pelvic pain, dysmenorrhea which may be associated with severe uterine cramps, nausea, vomiting, diarrhea, and uterine ischemia, dyspareunia, dysuria, mittelschmerz, and infertility.

The common therapies for endometriosis include the administration of hormones such as oral contraceptives and/or the administration of prostaglandin synthetase inhibitors, particularly non-steroidal anti-inflammatory agents (NSAIDs). Although proven effective, administration of hormones is known to be accompanied by varying degrees of side effects including changes in uterine bleeding, fatigue, weakness, hot flashes, decreased sex drive, nausea, acne or skin rash, depression, irritability, mood changes, and weight gain. NSAID treatment for endometriosis, similar to the treatment arthritis, has also been known to result in adverse effects including, in particular, gastrointestinal disorders.

Aspects of the present disclosure include methods of attenuating, alleviating, or treating a uterine-related disorder using the subject compounds and pharmaceutical compositions. In some embodiments of the method, a therapeutically effective amount of the pharmaceutical composition is administered to a subject that is female.

In some embodiments of the method, the uterine-related disorder is selected from endometriosis, dysmenorrhea, irregular menstrual bleeding, and dyspareunia. In some embodiments, the uterine-related disorder is endometriosis. In some embodiments, the uterine-related disorder is dysmenorrhea. In some embodiments, the uterine-related disorder is irregular menstrual bleeding. In some embodiments, the uterine-related disorder is dyspareunia.

The term "treating uterine-related disorder" is intended to encompass ameliorating or relieving one or more symptoms associated with endometriosis, dysmenorrhoea, irregular menstrual bleeding, and dyspareunia. The term "treating endometriosis" can further comprise the reduction in the size and number of endometriosis lesions.

Any convenient methods of administration can be utilized. In some embodiments of the method, the pharmaceutical composition is administered vaginally, e.g., using an applicator suitable for vaginal administration. In some embodiments of the method, the pharmaceutical composition is administered orally.

In some embodiments, the method further comprises co-administration of one or more additional active agents, or active pharmaceutical ingredients (API).

In some embodiments, the one or more additional active agents is a non-steroidal anti-inflammatory drug (NSAID). In some embodiments, the NSAID is selected from acetyl salicylic acid, indometacin, sulindac, phenylbutazone, diclofenac, fentiazac, ketorolac, piroxicam, tenoxicam, mecoxicam, meloxicam, cinnoxicam, ibufenac, ibuprofen, naproxen, ketoprofen, nabumetone, niflumic acid, nimesulide, and pharmaceutically acceptable salts thereof. In some embodiments, the NSAID is a Cox-2 inhibitor. In some embodiments, the Cox-2 inhibitor is selected from celecoxib, rofecoxib, parecoxib, and valdecoxib. In another embodiment, the Cox-2 inhibitor is selected from 4-(4-cyclohexyl-2-methyl-1,3-oxazol-5-yl)-2-fluorobenzenesulfonamide, 5-chloro-3-(4-(methylsulfonyl)phenyl)-2-(methyl-5-pyridinyl)pyridine, 2-(3,5-difluorophenyl)-3-4-(methylsulfonyl)phenyl)-2-cyclopenten-1-one, 4-[5-(4-methylphenyl)-3-(trifluoromethyl)-1H-pyrazol-1-yl]benzenesulfonamide, 4-(4-methylsulfonyl)phenyl-3-phenyl-2(5H)-furanone), 4-[5-methyl-3-phenylisoxazol-4-yl]benzenesulfonamide, N-[[(5-methyl-3-phenylisoxazol-4-yl)-phenyl]sulfonyl]propanamide, 4-[5-(4-chlorophenyl)-3-(trifluoromethyl)-1H-pyrazol-1-yl]benzenesulfonamide, N-(2, 3-dihydro-1, 1-dioxido-6-phenoxy-1, 2-benzisothiazol-5-yl) methanesulfonamide, 6-[[5-(4-chlorobenzoyl)-1,4-dimethyl-1H-pyrrol-2-yl]methyl]-3(2H)-pyridazinone, N-(4-nitro-2-phenoxyphenyl) methanesulfonamide, 3-(3,4-difluorophenoxy)-5,5-dimethyl-4-[4-(methylsulfonyl) phenyl]-2 (SH)-furanone, N-[6-[(2, 4-difluorophenyl) thio]-2, 3-dihydro-1-oxo-1H-inden-5-yl]methanesulfonamide, 3-(4-chlorophenyl)-4-[4-(methylsulfonyl) phenyl]-2 (3H)-oxazolone, 4-[3-(4-fluorophenyl)-2,3-dihydro-2-oxo-4-oxazolyl] benzenesulfonamide, 3-[4-(methylsulfonyl) phenyl]-2-phenyl-2-cyclopenten-1-one, 4-(2-methyl-4-phenyl-5-oxazolyl)benzenesulfonamide, 3-(4-fluorophenyl)-4-[4-(methylsulfonyl) phenyl]-2 (3H)-oxazolone, 5-(4-fluorophenyl)-1-[4-(methylsulfonyl) phenyl]-3-(trifluoromethyl)-1H-pyrazole, 4-[5-phenyl-3-(trifluoromethyl)-1H-pyrazol-1-yl]benzenesulfonamide, 4-[1-phenyl-3-(trifluoromethyl)-1H-pyrazol-5-yl] benzenesulfonamide, 4-[5-(4-fluorophenyl)-3-(trifluoromethyl)-1H-pyrazol-1-yl] benzenesulfonamide, N-[2-(cyclohexyloxy)-4-nitrophenyl] methanesulfonamide, N-[6-(2, 4-difluorophenoxy)-2, 3-dihydro-1-oxo-1H-inden-5-yl] methanesulfonamide, 3-(4-chlorophenoxy-4-[(methylsulfonyl)amino]benzenesulfonamide, 3-(4-chlorophenoxy-4-[(methylsulfonyl)amino]benzenesulfonamide, 3-[(1-methyl-1H-imidazol-2-yl) thio]-4 [(methylsulfonyl) amino] benzenesulfonamide, 5,5-dimethyl-4-[4-(methylsulfonyl) phenyl]-3-phenoxy-2(5H)-furanone, N-[6-[(4-ethyl-2-thiazolyl) thio]-1,3-dihydro-1-oxo-5-isobenzofuranyl] methanesulfonamide, 3-[(2,4-dichlorophenyl)thio]-4-[(methylsulfonyl)amino]benzenesulfonamide, 1-fluoro-4-[2-[4-(methylsulfonyl) phenyl]cyclopenten-1-yl] benzene, 4-[5-(4-chlorophenyl)-3-(difluoromethyl)-1H-pyrazol-1-yl] benzenesulfonamide, 3-[1-[4-(methylsulfonyl)phenyl]-4-(trifluoromethyl)-1H-imidazol-2-yl] pyridine, 4-[2-(3-pyridinyl)-4-(trifluoromethyl)-1H-imidazol-1-yl] benzenesulfonamide, 4-[5-(hydroxymethyl)-3-phenylisoxazol-4-yl]benzenesulfonamide, 4-[3-(4-chlorophenyl)-2,3-dihydro-2-oxo-4-oxazolyl] benzenesulfonamide, 4-[5-(difluoromethyl)-3-phenylisoxazol-4-yl] benzenesulfonamide, [1, 1':2', 1"-terphenyl]-4-sulfonamide, [1,1':2',1"-terphenyl]-4-(methylsulfonyl), 4-(2-phenyl-3-pyridinyl)benzenesulfonamide, N-[3-(phenylamino)-4-oxo-6-phenoxy-4H-1-benzopyran-7-yl] methanesulfonamide, and (5Z)-2-amino-5-[(3, 5-ditert-butyl-4-hydroxyphenyl)methylidene]-1,3-thiazol-4-one.

In some embodiments of the method, the additional active agent comprises a hormonal agent. The hormonal agent can be danazol, an oral contraceptive, GnRH agonist and antagonist, progestin, antiprogestin, medroxyprogesterone acetate, or an aromatase inhibitor.

Examples 11-12 of the experimental section describe experiments and results of experiments indicating that exemplary cannabinoid acid ester compound CBDA-Me are active in in vitro and in vivo models of endometriosis.

Cardiovascular-Related Diseases and Disorders

Cholesterol is essential for all animal life, for building and maintaining cell membranes and modulating membrane fluidity over the range of physiological temperatures. Also, cholesterol is the precursor for the synthesis of biomolecules such as Vitamin D and steroid hormones. About 80% of total daily cholesterol production occurs in the liver and the intestines and its biosynthesis is directly regulated by the cholesterol level present.

Having an excessively high-level of cholesterol increases the risk of a wide variety of diseases, in particular heart-related diseases. Elevated levels of cholesterol in the blood can lead to atherosclerosis which may increase the risk of heart attack, stroke and peripheral vascular disease. High levels of low-density lipoprotein (LDL) are believed to be the ones that most contribute to atherosclerosis, while high-density lipoprotein (HDL) transports cholesterol back to the liver and can remove cholesterol from cells and atheromas.

Hyperlipidemia encompasses diseases and disorders characterized by, or associated with, elevated levels of lipids and/or lipoproteins in the blood. Hyperlipidemias include hypercholesterolemia, hypertriglyceridemia, combined hyperlipidemia, and elevated lipoprotein a (Lp(a)). A particular prevalent form of hyperlipidemia in many populations is hypercholesterolemia.

Hypercholesterolemia, particularly an increase in low-density lipoprotein cholesterol (LDL-C) levels, constitutes a major risk for the development of atherosclerosis and coronary heart disease (CHD). Low-density lipoprotein cholesterol is identified and accepted as the primary target of cholesterol lowering therapy. Numerous studies have demonstrated that reducing LDL-C levels reduces the risk of CHD with a strong direct relationship between LDL-C levels and CHD events.

Familial hypercholesterolemia (FH) is an inherited disorder of lipid metabolism that predisposes a person to premature severe cardiovascular disease (CVD). FH can be either an autosomal dominant or an autosomal recessive disease that results from mutations in the low density lipoprotein receptor (LDLR), or in at least 3 different genes that code for proteins involved in hepatic clearance of LDL-C can cause FH. Examples of such defects include mutations in the gene coding for the LDL receptor (LDLR) that removes LDL-C from the circulation, and in the gene for apolipoprotein (Apo) B, which is the major protein of the LDL particle. In all cases, FH is characterized by an accumulation of LDL-C in the plasma from birth and subsequent development of tendon xanthomas, xanthelasmas, atheromata, and CVD. FH can be classified as either heterozygous FH (heFH) or homozygous FH (hoFH) depending on whether the individual has a genetic defect in one (heterozygous) or both (homozygous) copies of the implicated gene. Various medications are used to lower blood cholesterol levels. Statins, also known as HMG-CoA reductase inhibitors, are a class of lipid-lowering medications. Statins are effective in lowering LDL cholesterol and widely used for primary prevention in people at high risk of cardiovascular disease, as well as in secondary prevention for those who have developed cardiovascular disease. Side effects of statins include muscle pain, increased risk of diabetes mellitus, and abnormal blood levels of liver enzymes.

Aspects of the present disclosure include methods of treating or preventing cardiovascular and/or obesity-related diseases and disorders using the subject compounds and pharmaceutical compositions. In some embodiments of the method, a therapeutically effective amount of the pharmaceutical composition is administered to a subject in need thereof.

The pharmaceutical composition for lowering cholesterol according to the present methods is preferably used in a case in which the amount of LDL cholesterol in blood of the subject is increasing (preferably, in a case in which the amount is increasing beyond the normal value) or in a case in which an increase in the amount of LDL cholesterol in blood is anticipated (for example, in a case in which although the amount of LDL cholesterol is temporarily being suppressed by taking medications, the amount of LDL cholesterol is expected to increase when the dosing of medications is stopped), in order to lower these increases.

In some embodiments, the method is a method of reducing or maintaining cholesterol levels in a subject. In some embodiments, the method is a method of treating a high-cholesterol related disease or disorder. In some embodiments, treating the disease includes reducing the cholesterol level in the subject from a high-cholesterol level that is assessed prior to treatment. After administration of the subject pharmaceutical composition according to the subject methods, the cholesterol level in the subject can be re-assessed. In some cases, the cholesterol level is reduced from an elevated level prior to treatment to an acceptable normal level.

In some embodiments, the subject has been previously treated with another cholesterol lowering drug.

The cholesterol levels in a subject can be monitored before, during and/or after administration via any convenient methods. In some embodiments, the cholesterol level is determined by assaying a sample obtained from the subject, e.g., a blood sample.

In some embodiments, the method is a method of lowering LDL/HDL ratio in the subject. The LDL/HDL ratio in a subject can be monitored before, during and/or after administration via any convenient methods. In some embodiments, the LDL/HDL ratio is determined by assaying a sample obtained from the subject, e.g., a blood sample.

In some embodiments, the method is a method of treating a cardiovascular disease. In some embodiments, the use of the pharmaceutical composition is for treating or preventing atherosclerosis. In another embodiment, the use of the pharmaceutical composition is for treating or preventing hypercholesterolemia.

In some embodiments of the method, the disease is a cardiovascular disease. In some embodiments, the disease is hypercholesterolemia. In another embodiment, the hypercholesterolemia is selected from heterozygous familial hypercholesterolemia (HeFH) and homozygous familial hypercholesterolemia (HoFH).

A therapeutically effective amount of the subject compound or composition refers to an amount that is effective in reducing at least one lipid parameter in a patient. Similarly, a "therapeutically effective amount" of a combination of cannabidiolic acid ester and a second compound refers to an amount of cannabidiolic acid ester and an amount of the second compound that, in combination, is effective for preventing, ameliorating, or treating the specified disease or disorder. In some embodiments, the administration of the pharmaceutical composition results in reduction of at least one lipid parameter in the subject. In another embodiment, the administration of the pharmaceutical composition results in at least 20% reduction from baseline of at least one lipid parameter in the subject. In another embodiment, the administration of the pharmaceutical composition results in at least 25%, 30%, 35%, 40%, or 50% reduction from baseline of at least one lipid parameter in the patient. According to some embodiments, the method increases or maintains HDL levels in the patient.

In some embodiments of the method, the subject has an LDL-C level greater than or equal to 70 mg/dL. In another embodiment, the subject has an LDL-C level greater than or equal to 70, 75, 80, 85, 90, 95, or 100 mg/dL.

In some embodiments, the pharmaceutical composition is administered in combination with one or more additional therapeutic agents for reducing cholesterol. In another embodiment, the one or more additional therapeutic agents is a statin. In another embodiment, the statin is selected from Atorvastatin, Cerivastatin, Fluvastatin, Lovastatin, Mevastatin, Pitavastatin, Pravastatin, Rosuvastatin or Simvastatin or any combination thereof.

In some embodiments of the method, the one or more additional therapeutic agent is Niacin. In another embodiment, the one or more additional therapeutic agent is an antagonist of PCSK9. In another embodiment, the one or more additional therapeutic agent is Ezetimibe.

In some embodiments of the method of treating a cardiovascular disease, the administration of the pharmaceutical composition decreases cholesterol level in said patient as compared to that in said patient prior to administration of the pharmaceutical composition.

The pharmaceutical composition may be used in combination with other drugs that may also be useful in the reducing or maintaining cholesterol levels, reducing LDL/HDL levels, and/or treating or ameliorating of the diseases or conditions for which the cannabinoid acid esters described herein is useful. Such combinations may be used to treat one or more of such diseases as diabetes, obesity, atherosclerosis, and dyslipidemia, or diseases associated with metabolic syndrome. The combinations may exhibit synergistic activity in treating these diseases, allowing for the possibility of administering reduced doses of active ingredients, such as doses that otherwise might be sub-therapeutic. According to some embodiments, the pharmaceutical composition is used in combination with an additional therapeutic agent for reducing cholesterol.

According to some embodiments, the additional therapeutic agent is administered before, during, or after treatment with the pharmaceutical composition described herein.

Elevated LDL-C is most frequently treated with statins (3-hydroxy-3-methylglutaryl-co-enzyme-A reductase inhibitors). Statins lower LDL-C up to 50% from baseline, and reduce ASCVD risk by 15-37%. According to some embodiments, the additional therapeutic agent is statin. According to certain embodiments, the statin is selected from the group consisting of Atorvastatin, Cerivastatin, Fluvastatin, Lovastatin, Mevastatin, Pitavastatin, Pravastatin, Rosuvastatin or Simvastatin or any combination thereof. According to certain embodiments, the other therapeutic agent is Niacin. According to some embodiments, the treatment decreases cholesterol in said patient compared to said patient prior to treatment with cannabidiolic acid ester.

Fatty Liver, Chronic Kidney, and Metabolic-Related Disease and Disorders

The prevalence of obesity has risen significantly in the past decade in the United States and many other developed countries around the world. Obesity is associated with a significantly elevated risk for Non-alcoholic Fatty Liver Disease (NAFLD), chronic kidney disease (CKD), type 2 diabetes, coronary heart disease, hypertension, and numerous other major illnesses, and overall mortality from all causes.

Chronic kidney disease, also referred to as chronic kidney failure, describes the gradual loss of kidney function. Initially there are generally no symptoms; later, symptoms may include leg swelling, feeling tired, vomiting, loss of appetite, and confusion. Complications include an increased risk of heart disease, high blood pressure, bone disease, and anemia. Chronic kidney disease affected 753 million people globally in 2016: 417 million females and 336 million males. In 2015 it caused 1.2 million deaths. Despite the impact on human health and society, there are no successful targeted treatments to slow development of CKD and circumvent CKD progression to end stage kidney disease (ESKD). There are also few successful biomarkers for indicating early development and progression of CKD.

Non-alcoholic fatty liver disease (NAFLD) is a common chronic liver disease in developed countries. NAFLD can be classified as nonalcoholic fatty liver (NAFL) or nonalcoholic steatohepatitis (NASH). The spectrum of NAFLD disease itself includes simple hepatic steatosis, NASH, fibrosis, cirrhosis, and subsequent complications such as hepatocellular carcinoma (HCC). The etiology is multifactorial and yet incompletely understood, but involves accumulation of intrahepatic lipids (IHL), alterations of energy metabolism, insulin resistance, and inflammatory processes (Jasirwan et al. Biosci Microbiota Food Health. 2019; 38(3): 81-88).

Aspects of the present disclosure include methods of treating NAFLD, CKD, diabetes (e.g., Type-2 diabetes), dyslipidemia, metabolic syndrome, hyperglycemia, or obesity. In some embodiments, the method includes administering a therapeutically effective amount of a subject compound or pharmaceutical composition to a subject in need thereof. In some embodiments, the subject is diagnosed as having NAFLD, CKD, diabetes, dyslipidemia, metabolic syndrome, hyperglycemia, or obesity.

Example 17 of the experimental section, and FIGS. 22-30 describe experiments and results indicating the exemplary cannabinoid acid ester compound CBDA-Me demonstrates an impressive ability to prevent or mitigate various metabolic conditions by (i) ameliorating weight gain; (ii) preventing body and liver fat storage; (iii) preserving normal glucose homeostasis; and (iv) preserving kidney and liver function.

In another embodiment, the pharmaceutical composition for use is administered in combination with one or more additional therapeutic agents, such as additional therapeutic agents suitable for treating NAFLD or CKD.

Methods of Preparation

The compositions of the present disclosure may be formulated as single-phase aqueous, emulsion or multiple emulsions. According to some embodiments, the composition is formulated as emulsion. These emulsions may be oil-in-water (o/w) (including silicone in water) emulsions, water-in-oil (including water-in-silicone) (w/o) emulsions, or multiple emulsions such as oil-in-water-in-oil (o/w/o) or water-in-oil-in-water (w/o/w). It is understood that the oil phase can comprise silicone oils, non-silicone organic oils, or mixtures thereof. The compositions can comprise two immiscible phases that are admixed at the time of use by shaking. Each possibility represents a separate embodiment of the present disclosure.

According to some embodiments, the composition is made by preparing a dispersion of each component in a suitable solvent (dispersant), adjusting the dispersion pH with a pH adjusting agent, if necessary, and admixing the dispersions with shear to permit the formation of the desired matrix.

A common mode of administration of medical cannabis is by dissolving the cannabis extract or pure cannabinoid in triglyceride oils, such as vegetable oils, for oral delivery and administration. The oil is either filled into capsules or used as-in in various volumes. In contrast to administration by inhalation, the oral route of administration is perceived as an acceptable mode of self-medication, such as consuming a pill, a tablet, or a capsule. In such cases, an immediate release of the cannabinoid is obtained with fast absorption and an intermediate duration time of activity, but longer than smoking or vaporization.

A person of ordinary skill in the art can select the appropriate presentation or administration form, and the method of preparing it on the basis of general knowledge, taking into account the nature of the constituents used and the intended use of the composition.

The present disclosure also provides for kits comprising the above compositions. The compositions as described herein can be packaged to comprise, either separately or in the kit form together with a container, instructions for using or instruction brochures for using the compositions as described herein.

Combination Therapy

The compositions of the present disclosure may be used in pharmaceutical combinations with other therapeutic agents that may also be useful for treating the diseases or disorders as described herein. Such therapeutic agents may be administered by a route, in a therapeutically effective amount as commonly used thereof, contemporaneously or sequentially with the compositions as described herein.

The compositions as described in the present disclosure may be used contemporaneously with one or more other therapeutic agents in a unit dosage form. The combination therapy described herein may also comprise therapies in which the composition as described herein and the one or more other therapeutic agents are administered concomitantly, wherein the one or more other therapeutic agents are administered on the same or different schedules as the composition as described herein.

When oral formulations are used, the composition described herein and the other therapeutic agents may be combined into a single combination tablet or other oral dosage form, or the other therapeutic agents may be packaged together as separate tablets or other oral dosage forms. When used in combination with one or more other active ingredients, the active ingredients may be used in lower doses than when each is used alone.

In some embodiments, the pharmaceutical composition as described herein is used in combination with one or more additional therapeutic agents for treating various diseases and disorders as described herein.

In some embodiments, the pharmaceutical composition as described herein and the one or more additional therapeutic agents is administered simultaneously, concurrently, alternately, sequentially, or successively. In another embodiment, the pharmaceutical composition as described herein and the one or more additional therapeutic agents are administered according to an overlapping schedule.

In some embodiments, the pharmaceutical composition described herein may be administered at any point prior to another treatment, wherein the time prior another treatment is 150 hr, 145 hr, 140 hr, 135 hr, 130 hr, 125 hr, 120 hr, 115 hr, 110 hr, 105 hr, 100 hr, 95 hr, 90 hr, 85 hr, 80 hr, 75, 70 hr, 65 hr, 60 hr, 55 hr, 50 hr, 45 hr, 40 hr, 35 hr, 30 hr, 25 hr, 20 hr, 15 hr, 10 hr, 5 hr, 4 hr, 3 hr, 2 hr, 1 hr, 50 mins., 40 mins., 30 mins., 20 mins., 15 mins, 10 mins, 9 mins, 8 mins, 7 mins., 6 mins., 5 mins., 4 mins., 3 mins, 2 mins, or 1 min prior to the other treatment.

In some embodiments, the pharmaceutical composition described herein may be administered at any point prior to a second treatment of the pharmaceutical composition as described herein, wherein the time prior to the second treatment is about 150 hr, 145 hr, 140 hr, 135 hr, 130 hr, 125 hr, 120 hr, 115 hr, 110 hr, 105 hr, 100 hr, 95 hr, 90 hr, 85 hr, 80 hr, 75, 70 hr, 65 hr, 60 hr, 55 hr, 50 hr, 45 hr, 40 hr, 35 hr, 30 hr, 25 hr, 20 hr, 15 hr, 10 hr, 5 hr, 4 hr, 3 hr, 2 hr, 1 hr, 50 mins., 40 mins., 30 mins., 20 mins., 15 mins, 10 mins, 9 mins, 8 mins, 7 mins, 6 mins., 5 mins., 4 mins., 3 mins, 2 mins, or 1 min.

In some embodiments, the route of administration of the pharmaceutical composition as described herein or the one or more additional therapeutic agents can be by any route and will be determined based on the physician and the subject on an individual basis. All other routes of administration of a therapeutically effective amount of an agent or the pharmaceutical composition as described herein are included by the present disclosure.

Definitions

Unless defined otherwise, all technical and scientific terms used herein have the same meaning as commonly understood by one of ordinary skill in the art to which this disclosure pertains.

It is understood that the definitions provided herein are not intended to be mutually exclusive. Accordingly, some chemical moieties may fall within the definition of more than one term.

As used herein, the symbol " ------- " refers to a covalent bond comprising a single or a double bond.

The term "alkyl" refers to an unbranched or branched saturated hydrocarbon chain. In some embodiments, alkyl as used herein has 1 to 50 carbon atoms (($C_1$-$C_{50}$)alkyl), 1 to 20 carbon atoms (($C_1$-$C_{20}$)alkyl), 1 to 10 carbon atoms (($C_1$-$C_{10}$)alkyl), 1 to 8 carbon atoms (($C_1$-$C_8$)alkyl), 1 to 6 carbon atoms (($C_1$-$C_6$)alkyl), or 1 to 4 carbon atoms (($C_1$-$C_4$)alkyl). Examples of alkyl groups may, for example, include methyl, ethyl, n-propyl, isopropyl, n-butyl, sec-butyl, tert-butyl, n-pentyl, 2-pentyl, isopentyl, neopentyl, n-hexyl, 2-hexyl, 3-hexyl, and 3-methyl pentyl. When an alkyl residue having a specific number of carbons is named, all geometric isomers having that number of carbons may be encompassed. Thus, for example, "butyl" can include n-butyl, sec-butyl, isobutyl and t-butyl, and "propyl" can include n-propyl and isopropyl.

The term "substituted alkyl" refers to an alkyl group as defined herein wherein one or more carbon atoms in the alkyl chain have been optionally replaced with a heteroatom such as O-, N-, S-, —S(O)n- (where n is 0 to 2), —NR— (where R is hydrogen or alkyl) and having from 1 to 5 substituents selected from the group consisting of alkoxy, substituted alkoxy, cycloalkyl, substituted cycloalkyl, cycloalkenyl, substituted cycloalkenyl, acyl, acylamino, acyloxy, amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-aryl, —SO-heteroaryl, —$SO_2$-alkyl, —$SO_2$-aryl, $SO_2$-heteroaryl, and —NR'R", wherein R' and R" may be the same or different and are chosen from hydrogen, optionally substituted alkyl, cycloalkyl, alkenyl, cycloalkenyl, alkynyl, aryl, heteroaryl and heterocyclic.

The term "alkylene" refers to a di-radical alkyl group. Unless otherwise indicated, such groups include saturated hydrocarbon chains containing from 1 to 24 carbon atoms, which may be substituted or unsubstituted, may contain one or more alicyclic groups, and may be heteroatom-containing. "Lower alkylene" refers to alkylene linkages containing from 1 to 6 carbon atoms. Examples include, methylene (—$CH_2$-), ethylene (—$CH_2CH_2$-), propylene (—$CH_2CH_2CH_2$-), 2-methylpropylene (—$CH_2$—CH ($CH_3$)—$CH_2$—), hexylene (—$(CH_2)_6$—) and the like.

The term "alkenyl" refers to an aliphatic hydrocarbon group containing at least one carbon-carbon double bond including straight-chain, branched-chain and cyclic alkenyl groups. In some embodiments, the alkenyl group has 2-10 carbon atoms (a $C_{2-10}$ alkenyl). In another embodiment, the alkenyl group has 2-4 carbon atoms in the chain (a $C_{2-4}$ alkenyl). Exemplary alkenyl groups include, but are not limited to, ethenyl, propenyl, n-butenyl, i-butenyl, 3-methylbut-2-enyl, n-pentenyl, heptenyl, octenyl, cyclohexylbutenyl and decenyl. An alkylalkenyl is an alkyl group as defined herein bonded to an alkenyl group as defined herein. The alkenyl group can be unsubstituted or substituted through available carbon atoms with one or more groups defined hereinabove for alkyl The term "alkynyl" refers to straight or branched monovalent hydrocarbyl groups having from 2 to 6 carbon atoms and preferably 2 to 3 carbon atoms and having at least 1 and preferably from 1 to 2 sites of acetylenic (C≡C—) unsaturation. Examples of such alkynyl groups include, but are not limited to, acetylenyl (C≡CH), and propargyl ($CH_2$C≡CH).

The terms "alkenylene," "alkynylene," "arylene," "arylalkylene," and "alkylarylene" refer to di-radical alkenyl, alkynyl, aryl, arylalkyl, and alkylaryl groups, respectively.

The terms "cycloalkyl" and "bicycloalkyl" refers to cyclic alkyl groups of from 3 to 10 carbon atoms having single or multiple cyclic rings including fused, bridged, and spiro ring systems. Examples of suitable cycloalkyl groups include, but are not limited to, adamantyl, cyclopropyl, cyclobutyl, cyclopentyl, cyclooctyl and the like. Such cycloalkyl groups include, by way of example, single ring structures such as cyclopropyl, cyclobutyl, cyclopentyl, cyclooctyl, and the like, or multiple ring structures such as adamantanyl, and the like.

The terms "substituted cycloalkyl" and "substituted bicycloalkyl" refer to cycloalkyl groups having from 1 to 5 substituents, or from 1 to 3 substituents. selected from alkyl, substituted alkyl, alkoxy, substituted alkoxy, cycloalkyl, substituted cycloalkyl, bicycloalkyl, substituted bicycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

The term "substituted" refers that any one or more hydrogen atoms on the designated atom or group is replaced with one or more substituents other than hydrogen, provided that the designated atom's normal bonding valence is not exceeded. The one or more substituents include, but are not limited to, alkyl alkenyl, alkynyl, alkoxy, acyl, amino, amido, amidino, aryl, azido, carbamoyl, carboxyl, carboxyl ester, cyano, guanidino, halo, haloalkyl, heteroalkyl, heteroaryl, heterocycloalkyl, hydroxy, hydrazino, imino, oxo, nitro, alky sulfinyl, sulfonic acid, alkylsulfonyl, thiocyanate, thiol, thione, or combinations thereof. By way of example, there may be one, two, three, four, five, or six substituents.

The phrase "optionally substituted" means that a non-hydrogen substituent may or may not be present on a given atom, and, thus, the description includes structures wherein a non-hydrogen substituent is present and structures wherein a non-hydrogen substituent is not present.

The phrases "of the formula" and "of the structure" are not intended to be limiting and are used in the same way that the term "comprising" is commonly used. The term "independently selected from" is used herein to indicate that the recited elements, i.e., R groups or the like, can be identical or different.

The term "isomers" refers to two or more compounds comprising the same numbers and types of atoms, groups or components, but with different structural arrangement and connectivity of the atoms.

The term "tautomer" refers to one of two or more structural isomers which readily convert from one isomeric form to another and which exist in equilibrium.

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are non-superimposeable mirror images of one another.

Individual enantiomers and diastereomers of compounds of the present disclosure can be prepared synthetically from commercially available starting materials that contain asymmetric or stereogenic centers, or by preparation of racemic mixtures followed by resolution methods well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, (3) direct separation of the mixture of optical enantiomers on chiral liquid chromatographic columns, or (4) kinetic resolution using stereoselective chemical or enzymatic reagents. Racemic mixtures also can be resolved into their respective enantiomers by well-known methods, such as chiral-phase gas chromatography or crystallizing the compound in a chiral solvent. Stereoselective syntheses, a chemical or enzymatic reaction in which a single reactant forms an unequal mixture of stereoisomers during the creation of a new stereocenter or during the transformation of a pre-existing one, are well known in the art. Stereoselective syntheses encompass both enantio- and diastereoselective transformations. See, for example, Carreira and Kvaerno, Classics in Stereoselective Synthesis, Wiley-VCH: Weinheim, 2009.

Geometric isomers, resulting from the arrangement of substituents around a carbon-carbon double bond or arrangement of substituents around a cycloalkyl or heterocyclic ring, can also exist in the compounds of the present disclosure. The symbol = denotes a bond that may be a single, double or triple bond as described herein. Substituents around a carbon-carbon double bond are designated as being in the "Z" or "E" configuration, where the terms "Z" and "E" are used in accordance with IUPAC standards. Unless otherwise specified, structures depicting double bonds encompass both the "E" and "Z" isomers.

Substituents around a carbon-carbon double bond alternatively can be referred to as "cis" or "trans," where "cis" represents substituents on the same side of the double bond and "trans" represents substituent on opposite sides of the double bond. The arrangement of substituents around a carbocyclic ring can also be designated as "cis" or "trans." The term "cis" represents substituents on the same side of the plane of the ring and the term "trans" represents substituents on opposite sides of the plane of the ring. Mixtures of compound wherein the substituents are disposed on both the same and opposite sides of the plane of the ring are designated "cis/trans."

The present disclosure also encompasses isotopically-labeled compounds which are identical to those compounds recited herein, except that one or more atoms are replaced by an atom having an atomic mass or mass number different from the atomic mass or mass number usually found in nature ("isotopologues"). Examples of isotopes that can be incorporated into compounds described herein include isotopes of hydrogen, carbon, nitrogen, oxygen, phosphorus, fluorine and chlorine, such as $^2$H ("D"), $^3$H, $^{13}$C, $^{14}$C, $^{13}$N, $^{18}$O, $^{17}$O, $^{31}$P, $^{32}$P, $^{35}$S, $^{18}$F, and $^{36}$Cl, respectively. For example, a compound described herein can have one or more H atoms replaced with deuterium.

Certain isotopically-labeled compounds, such as those labeled with $^3$H and $^{14}$C, can be useful in compound and/or substrate tissue distribution assays. Tritiated ($^3$H) and carbon-14 ($^{14}$C) isotopes can be particularly preferred for their ease of preparation and detectability. Further, substitution with heavier isotopes such as deuterium can afford certain therapeutic advantages resulting from greater metabolic stability, such as increased in vivo half-life or reduced dosage requirements, and hence can be preferred in some circumstances. Isotopically-labeled compounds can generally be prepared by following procedures analogous to those disclosed herein, for example, in the Examples section, by substituting an isotopically-labeled reagent for a non-isotopically-labeled reagent.

Singular articles such as "a," "an" and "the" and similar referents in the context of describing the elements are to be construed to cover both the singular and the plural, unless otherwise indicated herein or clearly contradicted by context. Recitation of ranges of values herein are merely intended to serve as a shorthand method of referring individually to each separate value falling within the range, including the upper and lower bounds of the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (i.e., "such as") provided herein, is intended merely to better illuminate the embodiments and does not pose a limitation on the scope of the claims unless otherwise stated.

In some embodiments, where the use of the term "about" is before a quantitative value, the present disclosure also includes the specific quantitative value itself, unless specifically stated otherwise. As used herein, the term "about" refers to a ±10% variation from the nominal value unless otherwise indicated or inferred. Where a percentage is provided with respect to an amount of a component or material in a composition, the percentage should be understood to be a percentage based on weight, unless otherwise stated or understood from the context.

Where a molecular weight is provided and not an absolute value, for example, of a polymer, then the molecular weight should be understood to be an average molecule weight, unless otherwise stated or understood from the context.

It should be understood that the order of steps or order for performing certain actions is immaterial so long as the present disclosure remain operable. Moreover, two or more steps or actions can be conducted simultaneously.

A dash ("-") symbol that is not between two letters or symbols refers to a point of bonding or attachment for a substituent. For example, —NH$_2$ is attached through the nitrogen atom.

The terms "active agent," "drug," "pharmacologically active agent," and "active pharmaceutical ingredient" are used interchangeably to refer to a compound or composition which, when administered to a subject, induces a desired pharmacologic or physiologic effect by local or systemic action or both.

The terms "individual," "host," and "subject," are used interchangeably, and refer to an animal, including, but not limited to, human and non-human primates, including simians and humans; rodents, including rats and mice; bovines; equines; ovines; felines; canines; and the like. "Mammal" means a member or members of any mammalian species, and includes, by way of example, canines, felines, equines, bovines, ovines, rodentia, etc. and primates, i.e., non-human primates, and humans. Non-human animal models, i.e., mammals, non-human primates, murines, lagomorpha, etc. may be used for experimental investigations.

"Patient" refers to a human subject.

The terms "treating," "treatment," and the like, refer to obtaining a desired pharmacologic and/or physiologic effect, such as reduction of one or more symptoms of the disease or disorder. The effect may be prophylactic in terms of completely or partially preventing a disease or symptom thereof and/or may be therapeutic in terms of a partial or complete cure for a disease and/or adverse effect attributable to the disease. "Treatment," as used herein, covers any treatment of a disease in a mammal, particularly in a human, and includes: (a) preventing the disease or a symptom of a disease from occurring in a subject which may be predisposed to the disease but has not yet been diagnosed as having it (i.e., including diseases that may be associated with or caused by a primary disease); (b) inhibiting the disease, i.e., arresting its development; and (c) relieving the disease, i.e., causing regression of the disease (i.e., reduction in pain or other symptom).

The term "amelioration" or any grammatical variation thereof (e.g., ameliorate, ameliorating, and amelioration etc.), includes, but is not limited to, delaying the onset, or reducing the severity of a disease or condition (e.g., diarrhea, bacteremia and/or endotoxemia). Amelioration, as used herein, does not require the complete absence of symptoms.

The term "pharmaceutically acceptable salt" refers to a salt which is acceptable for administration to a subject. It is understood that such salts, with counter ions, will have acceptable mammalian safety for a given dosage regime. Such salts can also be derived from pharmaceutically acceptable inorganic or organic bases and from pharmaceutically acceptable inorganic or organic acids, and may comprise organic and inorganic counter ions. The neutral forms of the compounds described herein may be converted to the corresponding salt forms by contacting the compound with a base or acid and isolating the resulting salts.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like.

Other examples of salts include anions of the compounds of the present disclosure compounded with a suitable cation such as N$^+$, NH$_4^+$, and NW$_4^+$ (where W can be a C$_1$-C$_8$ alkyl group), and the like. For therapeutic use, salts of the compounds of the present disclosure can be pharmaceutically acceptable. However, salts of acids and bases that are non-pharmaceutically acceptable may also find use, for example, in the preparation or purification of a pharmaceutically acceptable compound.

Compounds included in the present compositions that are basic in nature are capable of forming a wide variety of salts with various inorganic and organic acids. The acids that can be used to prepare pharmaceutically acceptable acid addition salts of such basic compounds are those that form non-toxic acid addition salts, i.e., salts containing pharmacologically acceptable anions, including but not limited to, malate, oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts.

Compounds included in the present compositions that are acidic in nature are capable of forming base salts with various pharmacologically acceptable cations. Examples of such salts include alkali metal or alkaline earth metal salts and, particularly, calcium, magnesium, sodium, lithium, zinc, potassium, and iron salts.

Compounds included in the present compositions that include a basic or acidic moiety can also form pharmaceutically acceptable salts with various amino acids. The compounds of the disclosure can contain both acidic and basic groups; for example, one amino and one carboxylic acid group. In such a case, the compound can exist as an acid addition salt, a zwitterion, or a base salt.

The phrase "therapeutically effective amount" refers to the amount of a compound that, when administered to a mammal or other subject for treating a disease, condition, or disorder, is sufficient to affect such treatment for the disease, condition, or disorder. The "therapeutically effective amount" will vary depending on the compound, the disease and its severity and the age, weight, etc., of the subject to be treated.

The terms "pharmaceutically acceptable excipient," "pharmaceutically acceptable diluent," "pharmaceutically acceptable carrier," and "pharmaceutically acceptable adjuvant" are used interchangeably and refer to an excipient, diluent, carrier, or adjuvant that is useful in preparing a pharmaceutical composition that are generally safe, non-toxic and neither biologically nor otherwise undesirable, and include an excipient, diluent, carrier, and adjuvant that are acceptable for veterinary use as well as human pharmaceutical use. The phrase "pharmaceutically acceptable excipient" includes both one and more than one such excipient, diluent, carrier, and/or adjuvant.

The term "pharmaceutical composition" is meant to encompass a composition suitable for administration to a subject, such as a mammal, especially a human. In general a "pharmaceutical composition" is sterile, and preferably free of contaminants that are capable of eliciting an undesirable response within the subject (i.e., the compound(s) in the pharmaceutical composition is pharmaceutical grade). Pharmaceutical compositions can be designed for administration to subjects or patients in need thereof via a number of different routes of administration including oral, buccal, rectal, parenteral, intraperitoneal, intradermal, intracheal, intramuscular, subcutaneous, and the like.

As used herein, the term "sustained release", "delayed release", and "controlled release" refer to prolonged or extended release of the therapeutic agent or API of the pharmaceutical formulation. These terms may further refer to composition which provides prolonged or extended duration of action, such as pharmacokinetics (PK) parameters of a pharmaceutical composition comprising a therapeutically effective amount of the active pharmaceutical ingredient as described herein.

As used herein, the term "extract" as used herein refers a product prepared by extraction by physical means (e.g. by comminuting, pressing, heating, pulsed electric field assisted treatments, shear treatments and pressure wave treatments), by chemical means (e.g. by treatment with an acid, a base, a solvent) and/or by biochemical means (e.g. by treatment with hydrolytic enzymes, microorganisms). The term refers to a liquid substance obtained through extraction from a given substance, or to a concentrate or essence which is free of, or substantially free of solvent. The term extract may be a single extract obtained from a particular extraction step or series of extraction steps. Extract also may be a combination of extracts obtained from separate extraction steps or separate feedstocks. Such combined extracts are thus also encompassed by the term "extract". Any methods of extraction with suitable solvent are encompassed. Exemplary extraction methods can be found for example in U.S. Pat. No. 6,403,126. The extract may be obtained from any part of the plant e.g. from leaves, flowers, stems, roots, fruits and seeds. The extract may be aqueous or oily.

As used herein, the term "cannabis extract" refers to one or more plant extracts from the cannabis plant. A cannabis extract contains, in addition to one or more cannabinoids, one or more non-cannabinoid components which are co-extracted with the cannabinoids from the plant material. Their respective ranges in weight will vary according to the starting plant material and the extraction methodology used. Cannabinoid-containing plant extracts may be obtained by various means of extraction of cannabis plant material. Such means include but are not limited to supercritical or sub-critical extraction with $CO_2$, extraction with hot or cold gas and extraction with solvents. In some embodiments, the term refers to a mixture of liquid or semi-solid, resinous substances obtained through extraction from two or more different cannabis species. In some embodiments, the term refers also to a compound purified from the extract.

As used herein, the term "semi-solid" refers to a form which is a capable of supporting its own weight and holds its shape, or is capable of conforming to other shapes.

As used herein, the term "cannabis plant" refers to plants of the genus *Cannabis*, including but not limited to *Cannabis sativa*, *Cannabis indica*, and *Cannabis ruderalis*. According to some embodiment, cannabis plant is a CBD-rich strain of cannabis plant or THC-rich strain of cannabis plant. Each possibility represents a separate embodiment.

As used herein, "hybrid strain" refers to different strains of *Cannabis* which include differing amounts and/or ratios of the various cannabinoid compounds. For example, *Cannabis sativa* typically has a relatively high THC/CBD ratio. Conversely, *Cannabis* indica generally has a relatively low THC/CBD ratio compared to *Cannabis sativa*, although the absolute amount of THC can be higher in *Cannabis* indica than in *Cannabis sativa*.

As used herein, the terms "high-CBD strain" and "CBD-rich strain" are directed to a strain of cannabis plant which comprises CBD and optionally one or more additional cannabinoids, such as, for example but not limited to: THC, CBN, and the life.

As used herein, the terms "high-THC strain" and "THC-rich strain" are directed to a strain of cannabis plant which comprises THC and optionally one or more additional cannabinoids, such as, for example but not limited to: CBD, CBN, and the like.

In some embodiments, the compound of formula (II) is EPM-301.

In some embodiments, the compound of formula (IIb) is HU-580.

In some embodiments, the compound of formula (V) is EPM-302.

The cannabinoid component combination of the present disclosure is generally prepared by conventional methods such as are known in the art of making a mixture in the ratio described above. Such methods typically involve mixing of the CBDA ester and one or more additional cannabinoid compound(s), or one or more extract of a cannabis plant in one or more steps to a relatively uniform state, with or without heating, cooling, application of vacuum, and the like.

The above definitions are not intended to include impermissible substitution patterns (i.e., methyl substituted with 5 fluorines or heteroaryl groups having two adjacent oxygen ring atoms). Such impermissible substitution patterns are well known to the skilled artisan. When used to modify a chemical group, the term "substituted" may describe other chemical groups defined herein. For example, the term "substituted aryl" includes, but is not limited to, "alkylaryl." Unless specified otherwise, where a group is described as optionally substituted, any substituents of the group are themselves unsubstituted.

Generally, reference to or depiction of a certain element such as hydrogen or H is meant to include all isotopes of that element. For example, if an R group is defined to include hydrogen or H, it also includes deuterium and tritium. Compounds comprising radioisotopes such as tritium, $^{14}C$, $^{32}P$ and $^{35}S$ are thus within the scope of the present technology. Procedures for inserting such labels into the compounds of the present technology will be readily apparent to those skilled in the art based on the disclosure herein.

Unless the specific stereochemistry is expressly indicated, all chiral, diastereomeric, and racemic forms of a compound are intended. Thus, compounds described herein include enriched or resolved optical isomers at any or all asymmetric atoms as are apparent from the depictions. Racemic mixtures of R-enantiomer and S-enantiomer, and enantio-enriched stereomeric mixtures comprising of R- and S-enantiomers, as well as the individual optical isomers can be isolated or synthesized so as to be substantially free of their enantiomeric or diastereomeric partners, and these stereoisomers are all within the scope of the present technology.

The compounds described herein may exist as solvates, especially hydrates, and unless otherwise specified, all such solvates and hydrates are intended. Hydrates may form during manufacture of the compounds or compositions comprising the compounds, or hydrates may form over time due to the hygroscopic nature of the compounds. Compounds of the present technology may exist as organic solvates as well, including DMF, ether, and alcohol solvates, among others. The identification and preparation of any particular solvate is within the skill of the ordinary artisan of synthetic organic or medicinal chemistry.

As described herein, the text refers to various embodiments of the present compounds, compositions, and methods. The various embodiments described are meant to provide a variety of illustrative examples and should not be construed as descriptions of alternative species. Rather, it should be noted that the descriptions of various embodiments provided herein may be of overlapping scope. The embodiments discussed herein are merely illustrative and are not meant to limit the scope of the present technology.

EXAMPLES

The following examples are offered to illustrate the present disclosure and are not to be construed in any way as limiting the scope of the present technology. Any methods that are functionally equivalent are within the scope of the present technology. Various modifications of the present technology in addition to those described herein will become apparent to those skilled in the art from the foregoing description and accompanying figures. Such modifications fall within the scope of the appended claims.

Unless otherwise stated, all temperatures are in degrees Celsius. Efforts have been made to ensure accuracy with respect to numbers used (e.g., amounts, temperatures, etc.), but some experimental errors and deviation should be allowed for.

All experiments conformed to the ethical guidelines for investigation in conscious animals and in full compliance with the central Israeli animal care commission.

In the examples below, if an abbreviation is not defined, it has its generally accepted meaning.
General Synthetic Methods
Compound Characterization Final compounds were confirmed by HPLC/MS (high-performance liquid chromatography/mass spectrometry) analysis and determined to be ≥90% pure by weight. $^1$H and $^{13}$C NMR spectra were recorded in $CDCl_3$ (residual internal standard $CHCl_3=\delta$ 7.26), DMSO-$d_6$ (residual internal standard $CD_3SOCD_2H=\delta$ 2.50), methanol-$d_4$ (residual internal standard $CD_2HOD=\delta$ 3.20), or acetone-$d_6$ (residual internal standard $CD_3COCD_2H=\delta$ 2.05). The chemical shifts (δ) reported are given in parts per million (ppm) and the coupling constants (J) are in Hertz (Hz). The spin multiplicities are reported as s=singlet, bs=broad singlet, bm=broad multiplet, d=doublet, t=triplet, q=quartet, p=pentuplet, dd=doublet of doublet, ddd=doublet of doublet of doublet, dt=doublet of triplet, td=triplet of doublet, tt=triplet of triplet, and m=multiplet.
Biological Studies The biological activities of cannabinoid acid ester compounds of interest such as CBDA-Me are assessed according to a variety of methods, e.g., as described in the examples below.

Example 1—Synthesis of Cannabinoid Acid Compounds

The method described in PCT application WO2018/235079 was followed to prepare cannabidiolic acid (CBDA). A mixture of Cannabidiol (CBD, 314 mg, 1 mmol) and 2 molar solution of magnesium methyl carbonate (MMC/2M, 1.5 ml, 3 mmol) in dimethylformamide (DMF) was heated at 130° C. for 3 hours. Then the reaction was cooled to 0° C., acidified with 10% hydrochloric acid and extracted with ether. The organic layer was washed with saline, dried over the drying agent magnesium sulfate ($MgSO_4$) and then evaporated. The crude compound was then cleaned by column chromatography (20% ether-petroleum ether).

The synthetic method above is adapted to prepare carboxylic acid derivatives of a variety of cannabinoid compounds of interest.

Example 2—Synthesis of Cannabinoid Acid Ester Compounds

The method described in WO 2018/235079 was followed to prepare cannabidiolic acid methyl ester (CBDA-Me). To a solution of cannabidiolic acid (CBDA) (175 mg, 0.488 mmol) in 2.5 ml dichloromethane ($CH_2Cl_2$), was added 0.02 ml of methanol ($CH_3OH$, 0.488 mmol) and 7.2 mg of 4-pyrrolidinopyridine (0.048 mmol). The reaction was stirred for 5 minutes at room temperature followed by the addition of the coupling agent, N. N'-dicyclohexylcarbodiimide (DCC) (121 mg, 0.585 mmol) and stirring overnight. Then the solvent was evaporated and the crude mixture acidified with 5% hydrochloric acid and extracted with dichloromethane ($CH_2Cl_2$). The organic layer was washed with saturated aqueous sodium bicarbonate ($NaHCO_3$), dried over the drying agent magnesium sulfate ($MgSO_4$) and then evaporated. The crude compound is then cleaned by column chromatography (2% ether-petroleum ether).

$^1$H-NMR spectra were obtained using a Bruker AMX 300 MHz apparatus using deuterated DMSO. Thin-layer chromatography (TLC) was run on silica gel 60F254 plates (Merck). Column chromatography was performed on silica gel 60 Å (Merck). Compounds were located using a UV lamp at 254 nm.

$^1$H NMR (300 MHz, (($CD_3$)$_2$SO)) δ 6.18 (1H, s, Ar), 5.07 (1H, s), 4.44 (1H, s), 4.41 (1H, s), 3.82 (3H, s), 3.35 (1H, m), 2.66 (1H, m), 2.49 (2H, t), 2.09 (1H, b), 1.95 (3H, s), 1.71-1.05 (12, ms), 0.86 (3H, t).

The synthetic methods above are adapted to prepare a variety of cannabinoid acid ester compounds of interest.

Example 3—Synthesis of the Compound of Formula (V) (EPM-302)

CBDA-Me compound was dissolved in EtOH, followed by the addition of Pt/C catalyst and a 0.5% sulfide/H$_2$ solution under inert atmosphere, and the resulting mixture was allowed to react at room temperature. Solvent was then removed to give the crude mixture, and the desired product was isolated and purified by standard synthetic protocols to give the compound of formula (V) (EPM-302).

Example 4—Comparative Example Using Injectable Compositions of HA, CBDA-Me, CBDA-Me Combined with Chitosan or PRF Administration and Main Assessments in Rats Knee instability injuries are performed by a combined operation of an open meniscectomy, anterior cruciate ligament (ACL) transection and medial collateral ligament (MCL). The combined operation is performed under general anesthesia in 36 rats and result in progressive osteoarthritis of the medial knee compartment slowly spreading to the lateral compartment. Then groups of rats are then separated according to Table 1, and pain assessment is conducted based on a validated weight bearing method as measured by an incapacitance meter (LINTON Incapacitance meter). The technique involves measuring the amount of weight an animal places on an afflicted joint and the contralateral knee served as control. Five groups are tested and treated with four different injectable formulations. CBDA-Me is solubilized in the form of liposomes with phosphatidyl choline. Group No. 1 is treated with a formulation which include 10 mg of CBDA-Me, and chitosan suspended in aqueous, and is administrated immediately post-operative (PO) (day 0). Group No. 2 is treated with the same formulation of 10 mg of CBDA-Me and chitosan suspended in aqueous solution and is administrated 14 days PO. Group No. 3 is treated with a formulation of 10 mg of CBDA-Me and PRF suspended in aqueous solution, and is administrated 14 days PO. Group No. 4 is treated with a formulation of hyaluronic acid (HA) high molecular weight (1%, 100 μL, Arthrease, Ferring), and is administrated immediately PO (day 0). Group No. 5 is treated with the liposome formulation of 10 mg of CBDA-Me and phosphatidyl choline in aqueous solution, administrated 14 days PO. The groups are followed up to 42 days and then are sacrificed.

TABLE 1

Pain Assessments in Rats with HA, CBD, CBD and chitosan, or CBD and PRF

| Group No. | No. of animals | Composition | Administration clay post operation (PO) |
|---|---|---|---|
| 1 | 8 | CBDA-Me (10 mg)/chitosan | 0 |
| 2 | 8 | CBDA-Me (10 mg)/chitosan | 14 |
| 3 | 8 | CBDA-Me (10 mg)/PRF | 14 |
| 4 | 6 | HA (1%, 100 μL) | 0 |
| 5 | 6 | liposome formulation of CBDA-Me (10 mg) | 14 |

Example 5—Cannabidiolic Acid Methyl Ester (CBDA-Me) in an Animal Meniscectomy Model of Osteoarthritis This example illustrates the effects of EPM-301 on a partial meniscectomy/ACL transection rat model of surgical induced osteoarthritis and pain induced incapacitance.
Study Background Osteoarthritis is the most common joint disease, affecting most people over the age of 50 years. The disease is progressive, leads to debilitation and often requires expensive medical and surgical interventions. In contrast to other arthritis, there are no disease modifying agents available today to affect the joint destruction.

The model used is a well-established surgical model of osteoarthritis induction. The progress of the osteoarthritic changes is predictable and progressive (Bendele et al. *J Musculoskelet Neuronal Interact*. June 2001; 1(4):363-376). The evaluation of osteoarthritic changes is well correlated with the findings of incapacitance tester (Philpott et al., *Pain*, December 2017; 158 (12): 2442-2451). The evaluation of injectables into joints is often done using this animal model and evaluated using the incapacitance tester.
Study Design and Methods Rats were allowed to acclimatize for 1 week, followed by assessment of their weight bearing preference using an incapacitance meter. Unilateral medical meniscectomy and anterior cruciate ligament ligation (MMX/ACLT) surgery was performed on the right knee of a subject rat. Weight bearing preference was tested before and after surgery. After 2 weeks, treatments with both intra-articular (1) and. intra-peritoneal (6) administrations of EPM-301 began in the EPM-301 group. Weight bearing preference was then assessed 4 and 7 days after the start of therapy.

Wistar Rats (HsdHan female rats 225-249 grams) were acquired from Envigo. The rats were evaluated using an incapacitance tester. They were tested pre-operation, one-week post-operation, two weeks post-operation, prior to injection, 4 and 7 days post injections.

Morphological evaluation of the joint surfaces was performed using digital images of the joint EPM-301 was dissolved in a solution mixture of 1:1:18 EtOH:cremophor:seline to a final concentration of 3.5 mg/mL.

Intra-articular (i.a.) injection was carried out with 100 uL and intra-peritoneal (i.p.) injections were carried out with 150 uL. All were injected i.a. in the first day. EPM-301 was injected via i.p. administration on the first day, and for 5 additional days everyday via i.p. administration.

The animals were treated in a GCP approved facility. The EPM-301 was stored as 70 mg/ml stock solution dissolved in EtOH in a temperature monitored refrigerator at 4 degrees Celsius.

Student's t-test was performed at the last follow-up time to determine effect of the therapy as primary endpoint. The level of significance was 0.05 alpha. ANOVA was used to compare all time points, a post-hob analysis with the Scheffe all comparisons method was performed. Calculations were performed using the Analyze-it Excel add-on function.

The percentage weight bearing was calculated as the amount of weight born (in grams) on the right hind limb divided by the amount of weight born on the left hind limb. The ratio was expressed as percentage weight bearing. There were 6 animals in the EPM-301 treated group and 4 animals in the control group.
Results Prior to operation, the Rt/Lt weight bearing in both groups was similar, with an average value of 139.6% for the EPM-301 tested group and an average value of 95% for the control group (t-test p>0.08).

Immediately prior to injection (two weeks following model induction), the weight bearing was similar for both groups, with an average value of 42.25% for the EPM-301 group and 47.75% for the control group.

Following injection, the Rt limb weight was significantly better in the EPM-301 group as compared with the control group, with 106.7% for the EPM-301 treated group, and 59.0% for the control group. Such difference was found to be significant based on student t-test (p>0.0151). The change in weight bearing overtime in both groups is shown in FIG. 1.

Conclusion

It was shown that there was an advantage of treating rats with EPM-301 as compared with no therapy, and the surgery induced incapacitance was also resolved by the EPM-301 treatment. Such results demonstrate the superiority of the EPM-301 treatment in the partial meniscectomy/ACL transection rat model of surgical induced osteoarthritis and pain induced incapacitance.

Example 6—Comparison Study of CBDA-Me with Hyaluronic Acid (HA) and Corticosteroid (CS) in a Rat Meniscectomy Model of Osteoarthritis This example illustrates the comparison of EPM-301 therapy versus the gold standard intra-articular therapies such as hyaluronic acid and corticosteroid intra articular injections, in a partial meniscectomy/ACL transection rat model of surgical induced osteoarthritis and pain induced incapacitance.

Study Background

Osteoarthritis is the most common joint disease, affecting most people over the age of 50 years. The disease is progressive, leads to debilitation and often requires expensive medical and surgical interventions. In contrast to other arthritides, there are no disease modifying agents available today to affect the joint destruction.

The model used is a well-established surgical model of osteoarthritis induction. The progress of the osteoarthritic changes is predictable and progressive (Bendele et al. *J Musculoskelet Neuronal Interact*. June 2001; 1(4):363-376). The evaluation of osteoarthritic changes is well correlated with the findings of incapacitance tester (Philpott et al., *Pain*, December 2017; 158 (12): 2442-2451). The evaluation of injectables into joints is often done using this animal model and evaluated using the incapacitance tester.

Study Design and Methods

Rats were allowed to acclimatize for 1 week, followed by assessment of their weight bearing preference using an incapacitance meter. Unilateral medical meniscectomy and anterior cruciate ligament ligation (MMX/ACLT) surgery was performed on the right knee of a subject rat. Weight bearing preference was tested before and after surgery. After 2 weeks, treatments with both intra-articular (1) and. intra-peritoneal (6) administrations of EPM301 began in the EPM301 group. In the hyaluronate (HA) and corticosteroid (CS) groups, a single intra-articular injection was performed 2 weeks after model induction. Weight bearing preference was then assessed 4 and 7 days after the start of therapy.

Wistar Rats (HsdHan female rats 225-249 grams) were acquired from Envigo. The rats were evaluated using an incapacitance tester. They were tested pre-operation, one-week post-operation, two weeks post-operation, prior to injection, 4 and 7 days post injections.

Morphological evaluation of the joint surfaces was performed using digital images of the joint. The parameters evaluated included percentage of articular surface damage of the proximal tibia calculated as the area of lesions divided by the total condylar surface area, gross surface score and osteophyte score as described (Yanagisawa et al. *BMC Musculoskeletal Disorders*. April 2016; 17:188).

The gross finding score in the articular cartilage was graded as follows:
  (i) Grade 1—intact articular surface;
  (ii) Grade 2—minimal osteophyte;
  (iii) Grade 3—over spur formation;
  (iv) Grade 4—width of erosion area 0 to 0.5 mm
  (v) Grade 5—width of erosion area 0.5 to 1 mm.
  (vi) Grade 6—width erosion area 1 to 1.5 mm
  (vii) Grade 7—width of erosion area 1.5 to 2.0 mm
  (viii) Grade 8—width of erosion area >2.0 mm The osteophyte score was graded as follows:
  (i) Grade 0—normal around the medial tibia;
  (ii) Grade 1—osteophyte formation ⅓ around the medial tibia;
  (iii) Grade 2—osteophyte formation halfway around the medial tibia;
  (iv) Grade 3—osteophyte formation ⅔ around the medial tibia;
  (v) Grade 4—osteophyte formation all around the medial tibia.

EPM-301 was dissolved in a solution mixture of 1:1:18 EtOH:cremophor:seline to a final concentration of 3.5 mg/mL. Hyaluronic acid (Arthrease, 1% sodium hyaluronate) and Dexamethasone (kem Pharma, Venus, 72, Pol. Ind. Colom II, 08228 Terrassa, Barcelona) were acquired.

Intra-articular (i.a.) injection was carried out with 100 uL and intra-peritoneal (i.p.) injections were carried out with 150 uL. All were injected i.a. in the first day. EPM-301 was injected via i.p. administration on the first day, and for 5 additional days everyday via i.p. administration.

Student's t-test was performed at the last follow-up time to determine effect of the therapy as primary endpoint. The level of significance was 0.05 alpha. ANOVA was used to compare all time points, a post-hob analysis with the Scheffe all comparisons method was performed. Calculations were performed using the Analyze-it Excel add-on function.

The animals were treated in a GCP approved facility. The EPM-301 was stored as 70 mg/ml stock solution dissolved in EtOH in a temperature monitored refrigerator at 4 degrees Celsius.

The percentage of weight bearing was calculated as the amount of weight born (in grams) on the right hind limb divided by the amount of weight born on the left hind limb. This ratio was expressed as percentage weight bearing. Prior to operation the Rt/Lt weight bearing in both groups was similar. There were 4 animals in the EPM-301 treated group and 8 animals in each of the HA and CS treated groups, with a total of 20 tested subjects.

Results

Immediately prior to injection (two weeks following model induction), the weight bearing was similar for all groups, with 56.6% for the EPM-301 treated group, 57.9% for the HA treated group, and 52.5% for the CS treated group.

Figure 2:
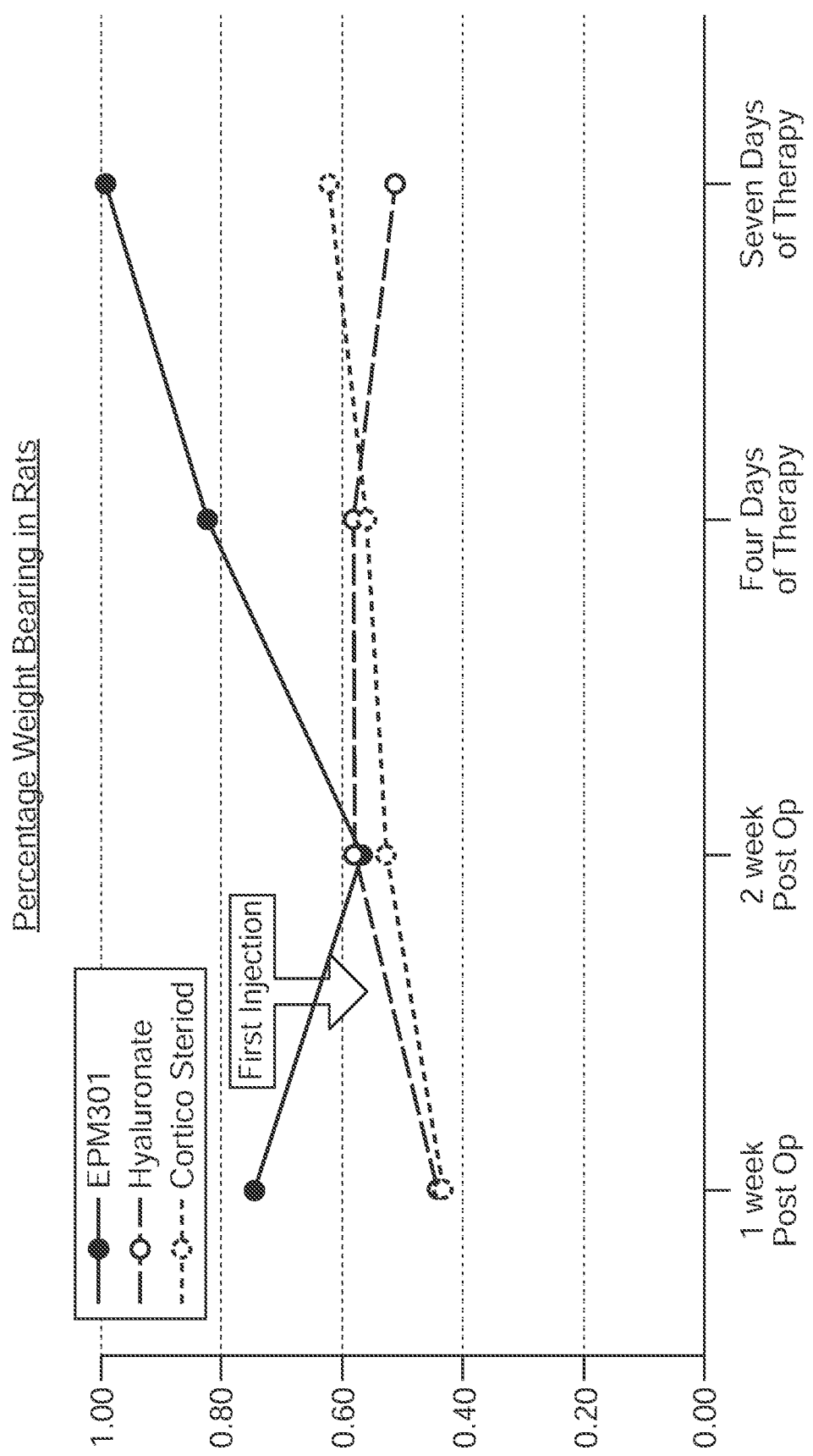
FIG. 2 shows the effect of CBDA-Me (EPM-301) treatment on percent weigh bearing in a rat partial meniscectomy\ACL transection model of surgical induced osteoarthritis and pain induced incapacitance as compared to hyaluronate and steroid treatments.

Following injections, the Rt limb weight bearing was significantly better in the EPM-301 group (99.1%) as compared with the HA (51.1%) and CS (62.1%) treated groups. Such difference was found to be statistically significant with t-test (p>0.0035) and the Scheffe test. The change in weight bearing over time (1 week after operation, 2 weeks after operation, 4 days after therapy, and 7 days after therapy) in both groups is shown in FIG. 2.

Figure 3:
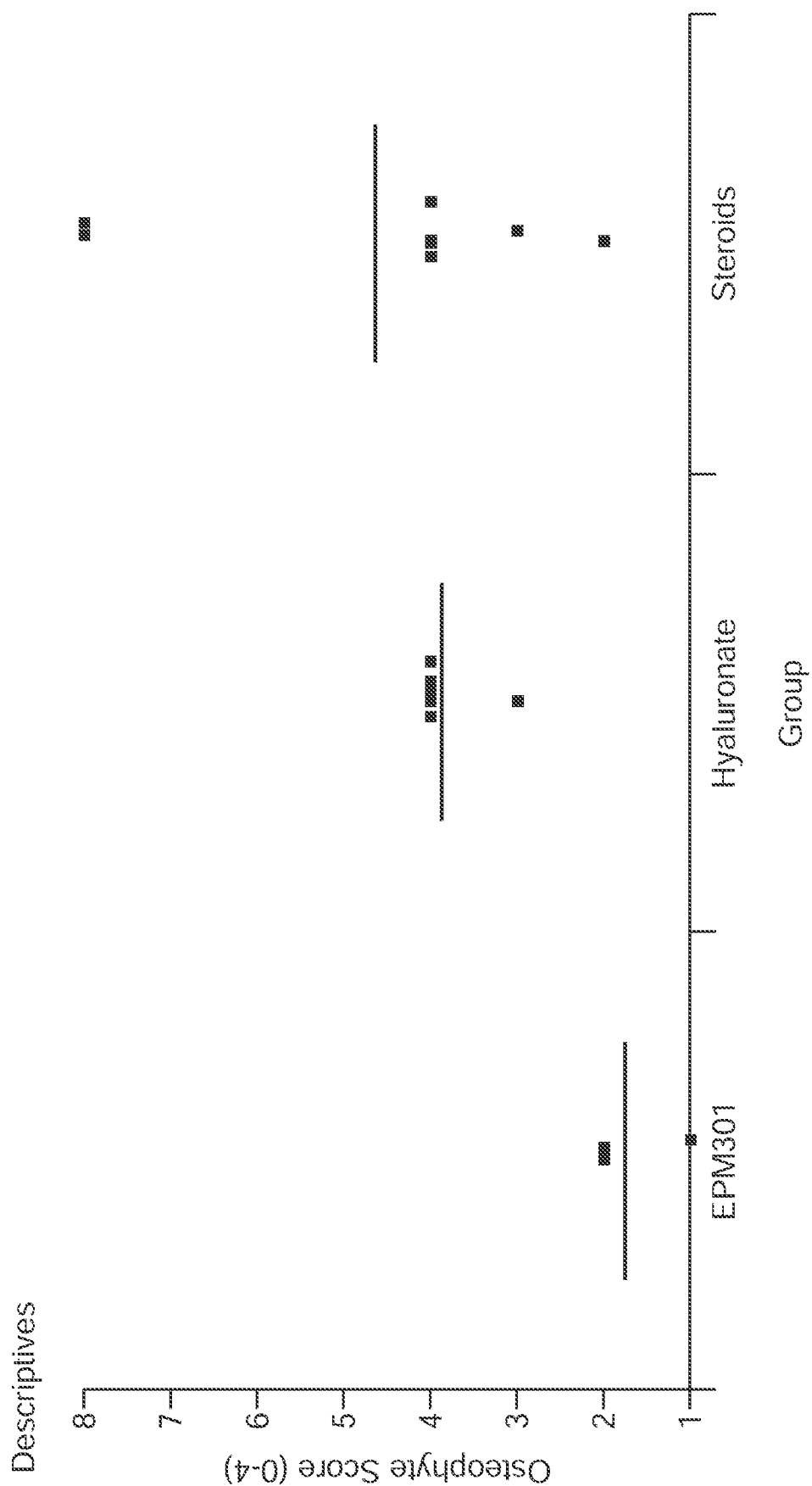
FIG. 3 shows the osteophyte scores of CBDA-Me (EPM-301) treated subjects as compared to hyaluronate and steroid treated groups.
Figure 4:
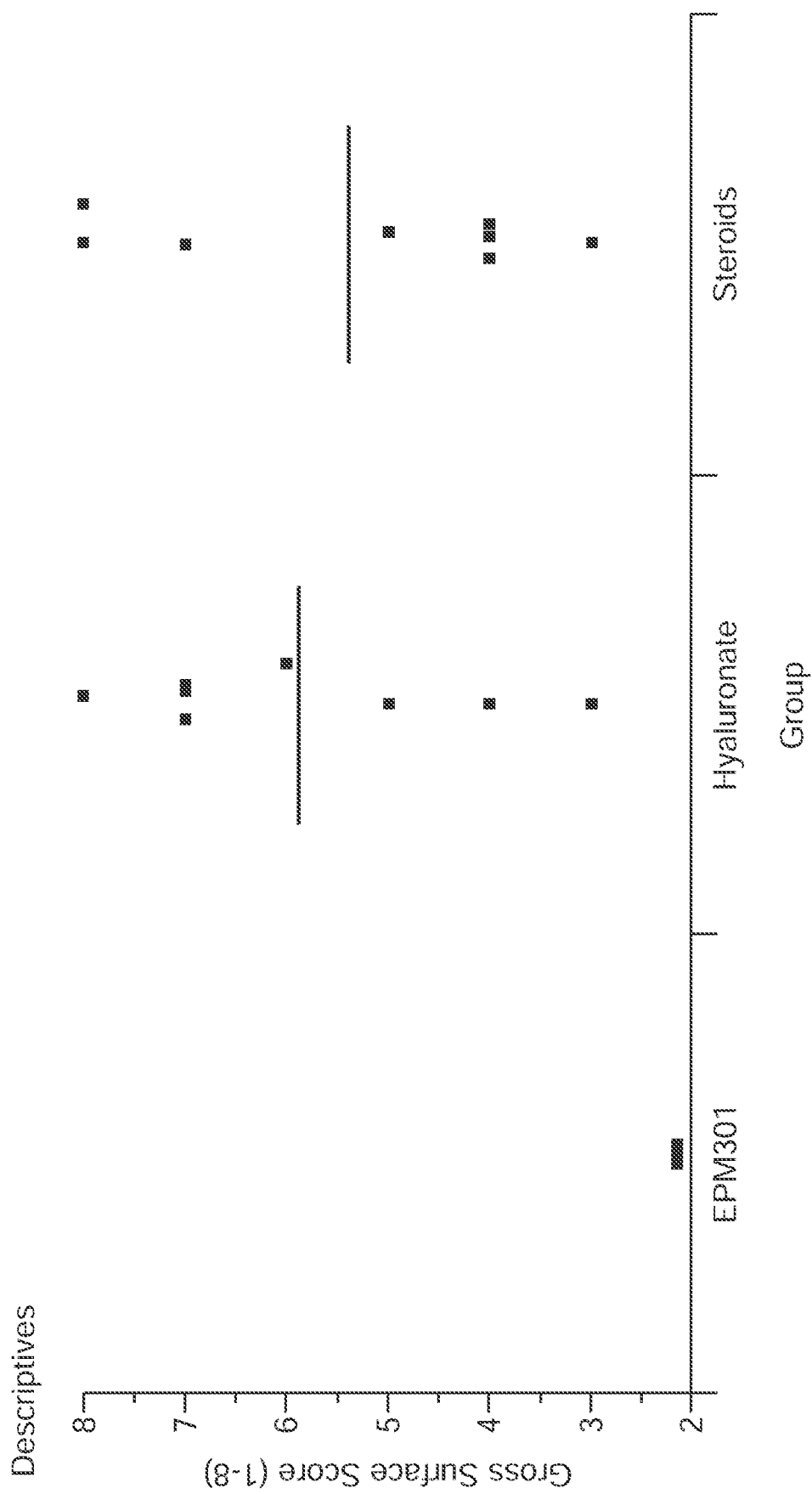
FIG. 4 shows the gross surface score of CBDA-Me (EPM-301) treated subjects as compared to hyaluronate and steroid treated groups.
Figure 5:
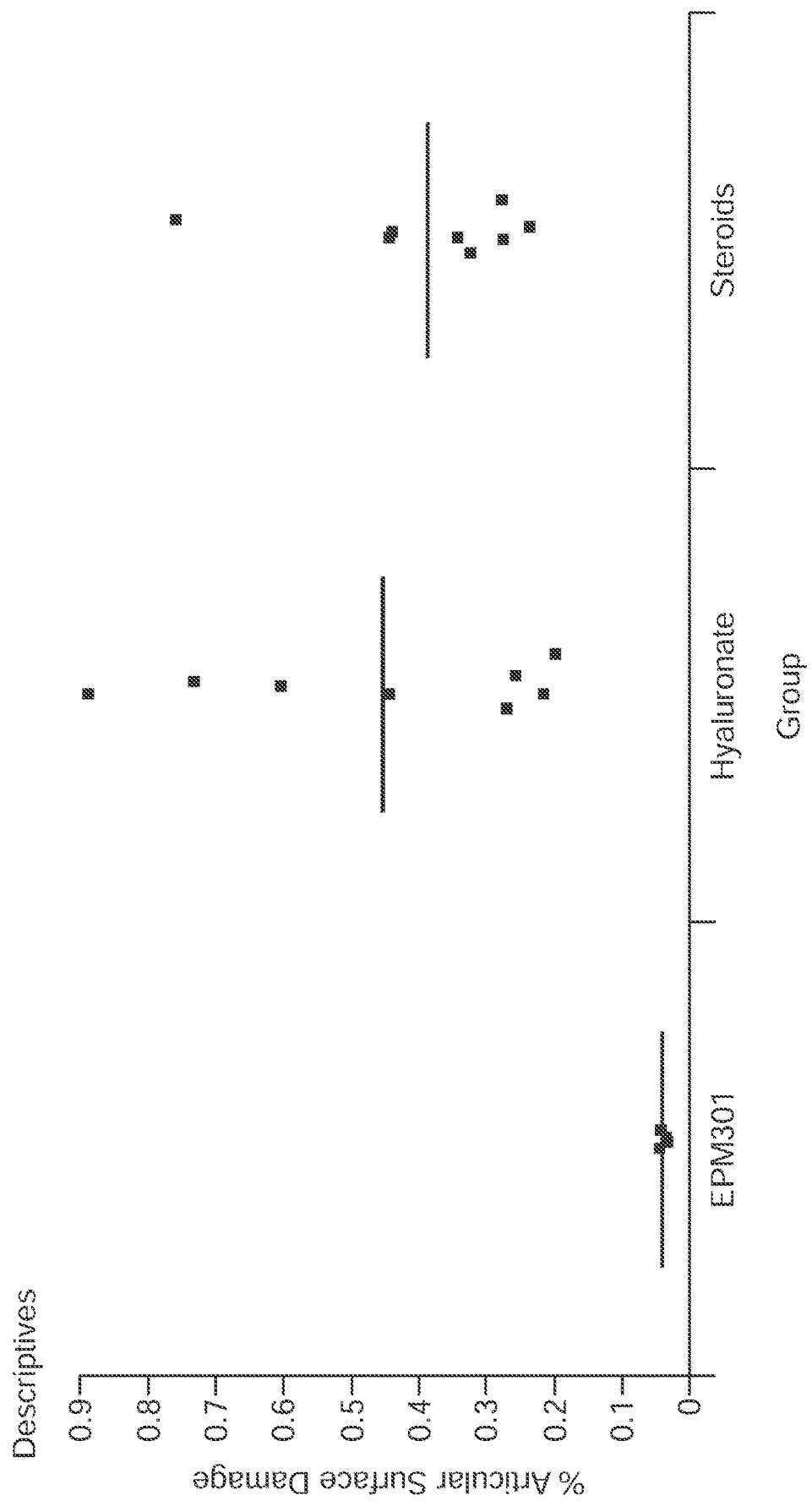
FIG. 5 shows the articular surface damage scores of CBDA-Me (EPM-301) treated subjects as compared to hyaluronate and steroid treated groups.

The osteophyte, gross surface, and articular surface damage scores were also measured in all the treated groups and shown in FIGS. 3-5 respectively. The osteophyte scores provided evidence of superiority of the EPM-301 treatment relative to the hyaluronic acid and the corticosteroid treatments, as shown in FIG. 3. The gross surface score also showed improvement of the EPM-301 treated group as compared to the HA and CS treated groups as shown in FIG. 4. Lastly, as shown in FIG. 5, less percentage of articular surface damage was observed in the EPM-301 treated group as compared to the HA and CS treated groups.

Conclusion

As demonstrated by the results of this experiment, treatment with EPM-301 was shown to exhibit advantages in rats as compared to treatment with hyaluronate and corticosteroid treatments. More significantly, the incapacitance induced by surgical treatment in rats was also resolved by EMP-301 treatment.

Example 7—Cannabidiolic Acid Methyl Ester (CBDA-Me) Liquid Formulations

Two different formulations of CBDA-Me are prepared and analyzed according to the below:
1.) CBDA-Me+hydroxypropyl β-cyclodextrin (βCD)+ PEG in an acceptable physiological buffer, adjusted to physiological pH. The liquid formulation is sterilized and sodium hyaluronate is added.
2.) CBDA-Me+phosphatidylcholine+cholesterol in PBS. The mixture is homogenated with 1:1 hyaluronic acid.

The effect of the two formulations is examined in a rat knee stability model as described in Example 4. The formulations efficacy is compared to CBD formulations and control.

Example 8—Cannabidiolic Acid Methyl Ester (CBDA-Me) Cream Topical Formulation A cream is formulated by blending an oil phase with an aqueous phase to form an emulsion. The oil phase is made by dispersing talc powder or silica powder into mineral oil or silicon oil. Aqueous phase is made by dispersing emulsifier such as PEG-100 or sorbitan thickener such as cellulose derivative and stabilizer such as methyl phenyl into water. Then the cannabinoid combination of the present invention is added into the emulsion. It may be stirred with or without heating, cooling, application of vacuum, to form relatively uniform state.

The effect of the above formulations is examined in vitro in four different models of skin inflammatory diseases: (1) microbial infection-induced dermatitis; (2) solar dermatitis; (3) atopic dermatitis; and (4) allergic contact dermatitis.

The formulation efficacy in each disease model is then compared to other CBD formulations and control.

Different human skin samples such as human skin organ culture (hSOC) are used to determine efficacy and cytotoxicity.

Example 9—In Vitro Evaluation of Anti-Psoriatic Activity of Cannabidiolic Acid Methyl Ester (CBDA-Me)

CBDA-Me efficacy is evaluated by a quantitative method for measuring anti-psoriatic activity by the mouse tail test (Bosman B. Skin Pharmacol. 1992; 5:41-48). Male albino mice (ICR) (6 for each formulation) are treated daily for 6 days. Treatment includes topical administration once a day on the tail base, about 1 cm from the proximal end of the tail to about 2 cm section long. At the end of experiment the mice are sacrificed and the treated section of the tail is removed. Longitudinal histological sections from the treated tail are prepared and % of orthokeratosis is evaluated. The CBDA-Me efficacy is compared to other cannabinoids.

Example 10—Ex Vivo Efficacy of Cannabidiolic Acid Methyl Ester (CBDA-Me) in Suppression of Dermal Inflammatory Mediators The efficacy of CBDA-Me was compared to that of corticosteroid treatment in an ex vivo model of induced inflammation of human skin explants (see for example WO2019/063122 and WO2014/182655).

Freshly excised healthy human skin was dermatomed to an approximate thickness of 750±100 μm. The dermatomed skin was cut into 1 cm$^2$ sections and mounted onto static Franz cells with a dosing area of approximately 0.6 cm$^2$.

The experiment was performed as follows:
(i) Static Franz cells (n=4 per treatment), with an average surface area of approximately 0.6 cm$^2$ and a volume of approximately 2.0 mL were employed.
(ii) Skin was mounted onto the static Franz cell, Stratum corneum side up, and clamped into place.
(iii) The receptor compartment was filled with approximately 2 mL of warm (ca. 37° C.) Cornification media.
(iv) CBDA-Me or 1% Perrigo® hydrocortisone ointment (control) was applied topically at 40 hours and 16 hours prior to stimulation and was incubated at 37° C. with 5% $C_{o2}$.
(v) The contents of the receptor compartment from each cell was vacuum aspirated and replaced with 2 mL pre-warmed (ca. 37° C.) cornification media, containing either Th1 or Th17 stimulation cocktail.
(vi) Tissue explants were harvested at 24 hours post-stimulation and placed in RNAlater® solution for further processing. A total of five biomarkers per stimulation were analysed via RT-qPCR.
Th1: IFNγ, TNFα, IL1β, IL2, IL13
Th17: IL17α, IL22, CXCL10, IL36g, SerpinB4
GAPDH was used as an internal control.

As shown in FIG. 6 and FIG. 7, CBDA-Me was shown to cause inhibition of both Th1 (chronic and acute atopic dermatitis (AD)) and Th17 (psoriasis) mediated inflammation, respectively, in a degree comparable/improved to that of the corticosteroid formulation. CBDA-Me's therapeutic potential is unexpectedly similar in efficacy to corticosteroids without the potential for adverse effects.

Example 11—CBDA-Me Efficacy in an Acute Colitis Model

The therapeutic effect of CBDA-Me on inflammatory bowel disease (IBD) was examined in an acute colitis mouse model. Colitis was induced in 10 weeks old female C57BL/6 mice using dextran sodium sulphate (DSS). Mice were fed for 8 days with 2% (wt/vol) DSS in their drinking water. Mice were administered (3 animals in each group) one of the following treatments by gavage: CBD (400 mg/kg), CBDA-Me (10 mg/kg or 40 mg/kg), DSS alone (untreated control), prednisone (90 mg/kg, control), none (healthy mice).

Figure 8:
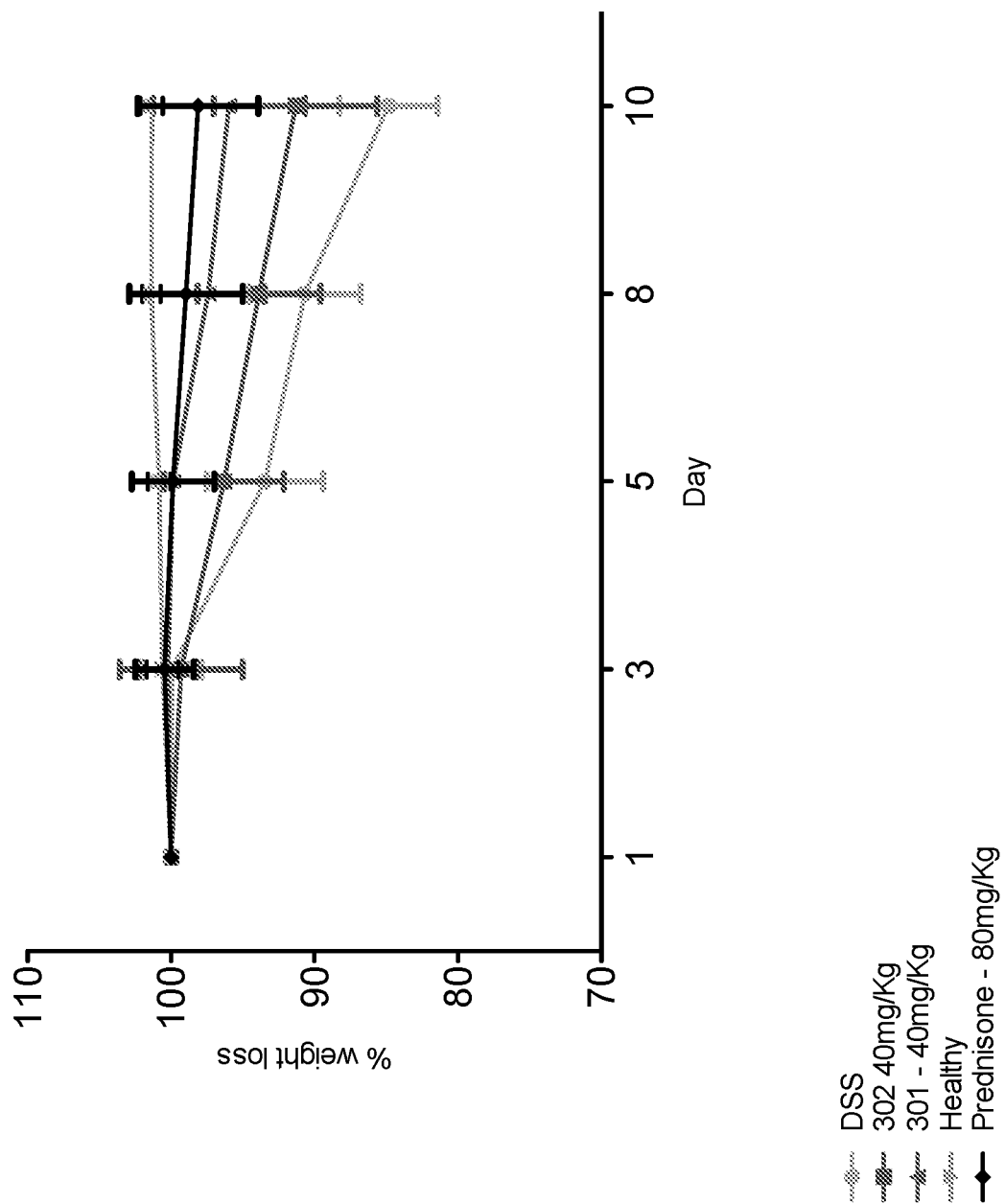
FIG. 8 shows the effect of CBDA-Me on weight loss in mouse models of acute colitis. Colitis was induced in 10 weeks old female C57BL/6 mice using dextran sodium sulphate (DSS). Mice were treated for 10 days with DSS, DSS+CBD, DSS+CBDA-Me, no DSS (healthy; negative control), or DSS+Prednisone (positive control). Mice weight was measured in days 1, 3, 5, 8, and 10.

Weight loss was measured on days 1, 3, 5, 8, and 10. As shown in FIG. 8 CBDA-Me treatment resulted in a reduced weight loss compared to CBD when treated with 40 mg/kg.

Figure 9:
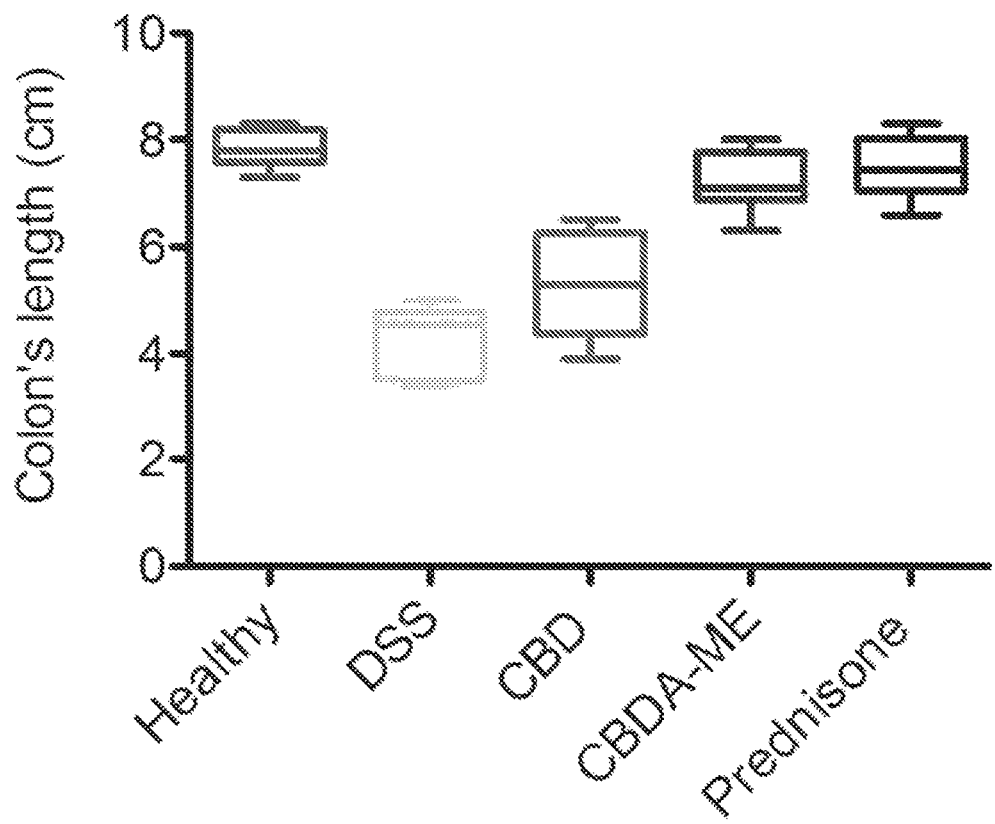
FIG. 9 shows the effect of CBD, CBDA-Me, or prednisone on colon length in mouse models of DSS induced acute colitis.
Figure 10:
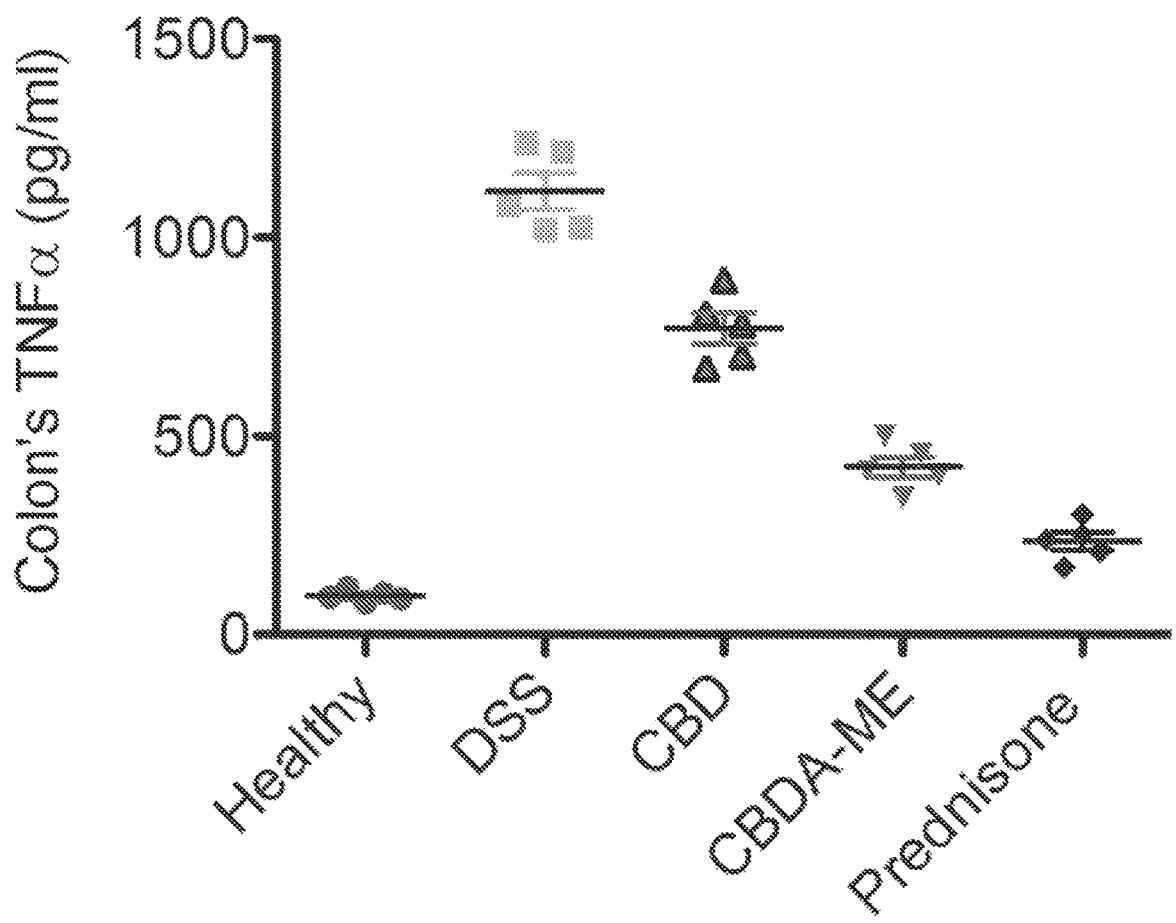
FIG. 10 shows the effect of CBD, CBDA-Me, or Prednisone on TNFα expression in the colon in mouse models of DSS induced acute colitis.
Figure 11:
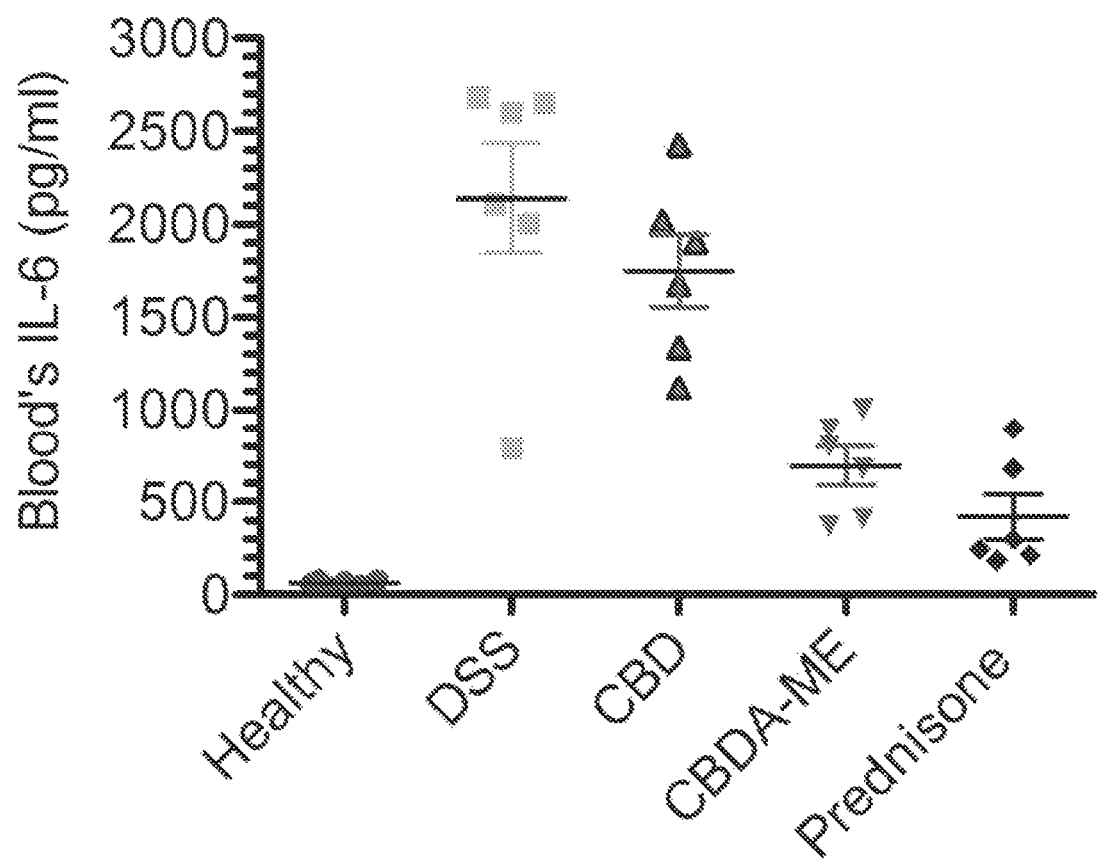
FIG. 11 shows the effect of CBD, CBDA-Me, or Prednisone on IL-6 levels in the blood in mouse models of DSS induced acute colitis.
Figure 12:
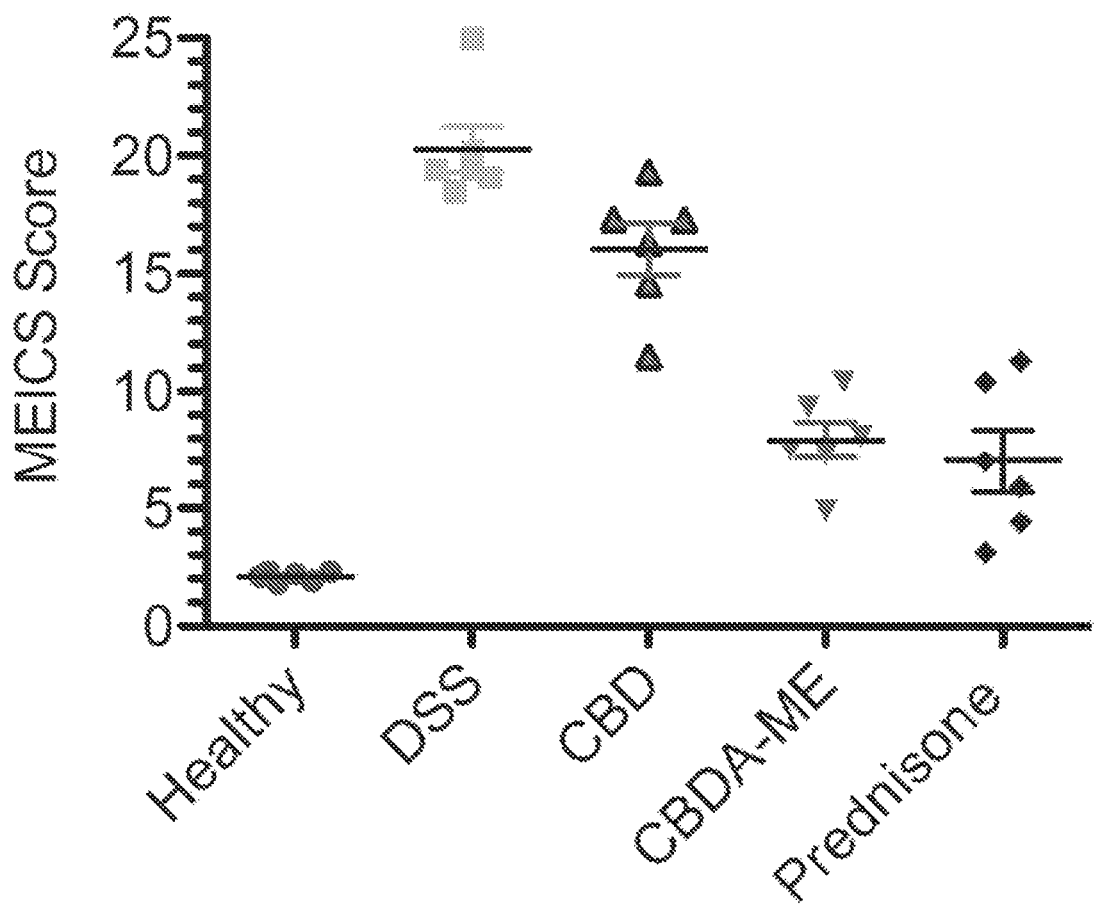
FIG. 12 shows the mouse endoscopic index of colitis severity (MEICS) scoring effect of CBD, CBDA-Me, or Prednisone in mouse models of DSS induced acute colitis.
Figure 13A:
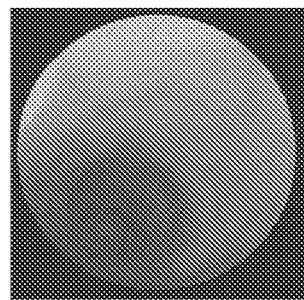
FIG. 13A-13E show the representative colonoscopy photos from healthy mouse (FIG. 13A) and from mouse models of DSS induced acute colitis after no treatment (FIG. 13B), after treatment with CBD (FIG. 13C), after treatment with CBDA-Me (FIG. 13D), and after treatment with Prednisone (FIG. 13E).
Figure 13B:
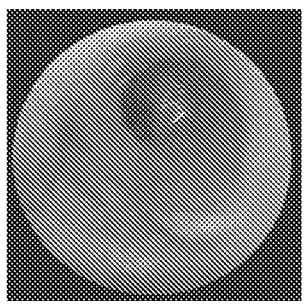
Figure 13C:
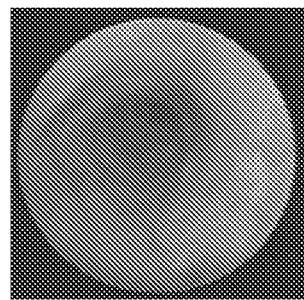
Figure 13D:
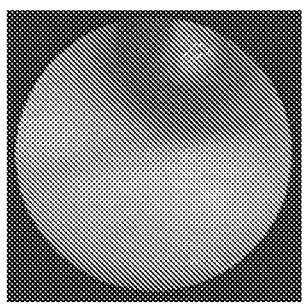
Figure 13E:
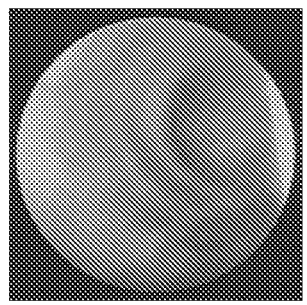
Figure 14:
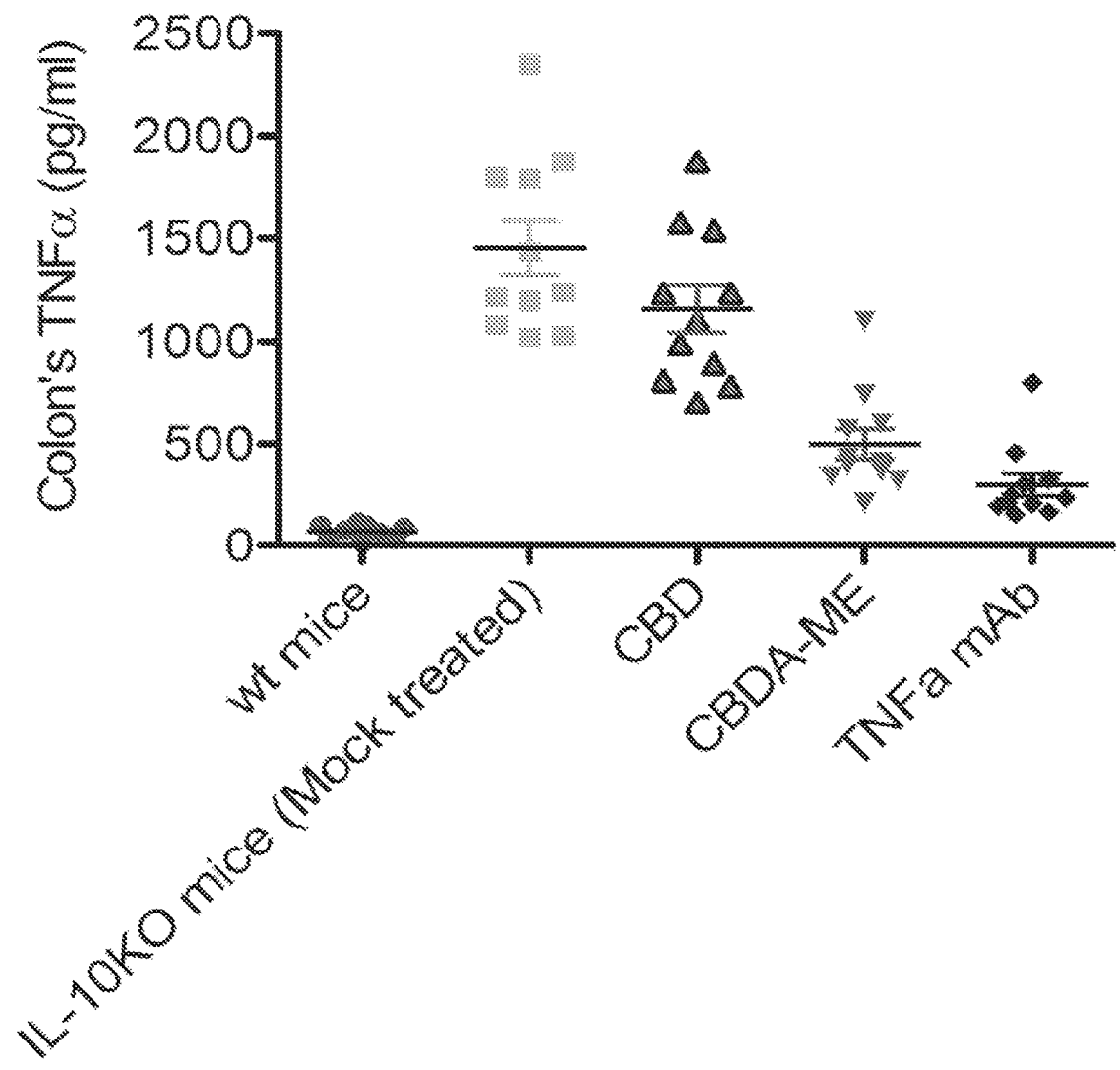
FIG. 14 shows TNFα expression in the colon of wild type mice, IL-10KO mice, and IL-10KO mice treated with CBD, CBDA-Me, or TNFα mAb.
Figure 15:
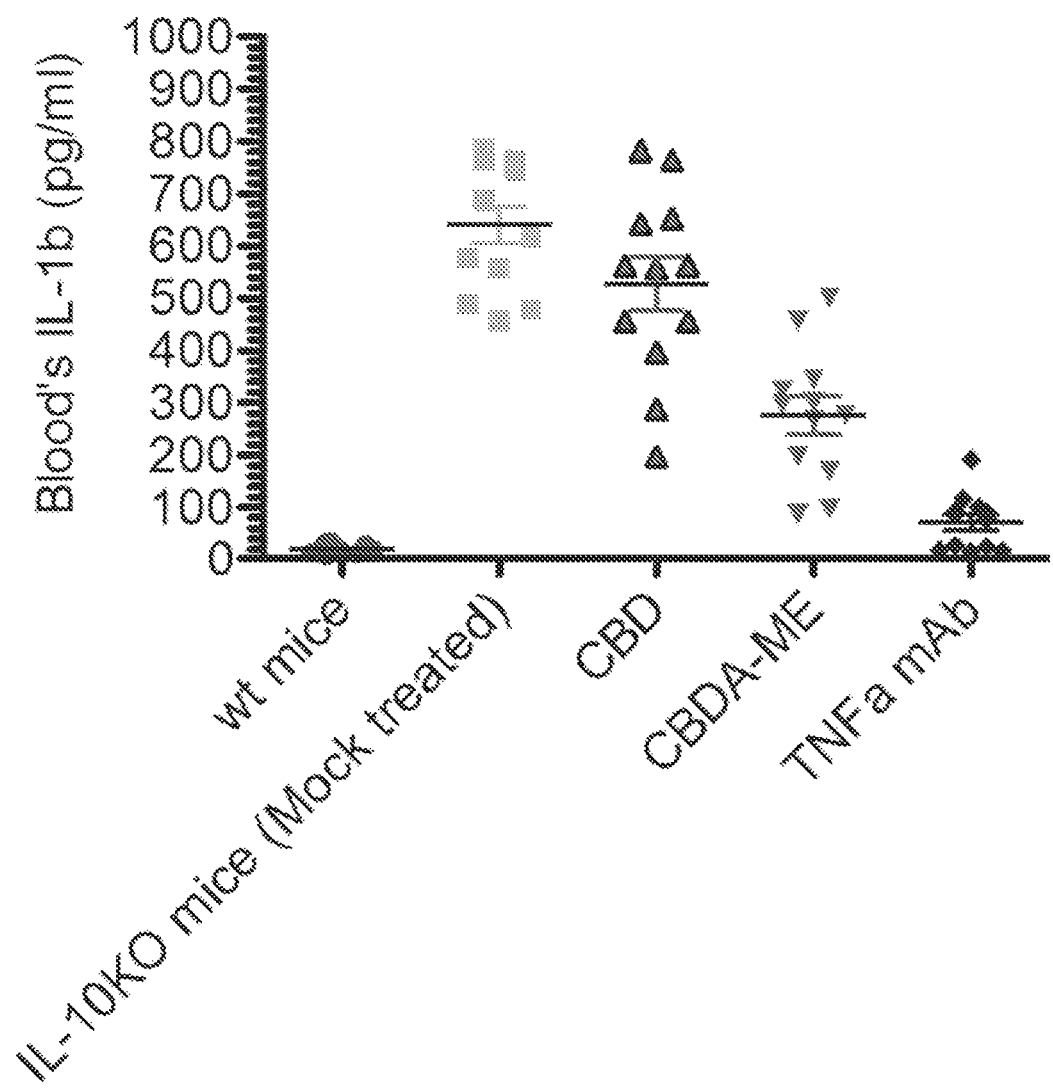
FIG. 15 shows the IL-1b levels in the blood of mouse models of chronic colitis mice. IL-1b was measured in wild type mice, as control, and IL-10KO mice treated with CBD, CBDA-Me, or TNFα mAb.
Figure 16:
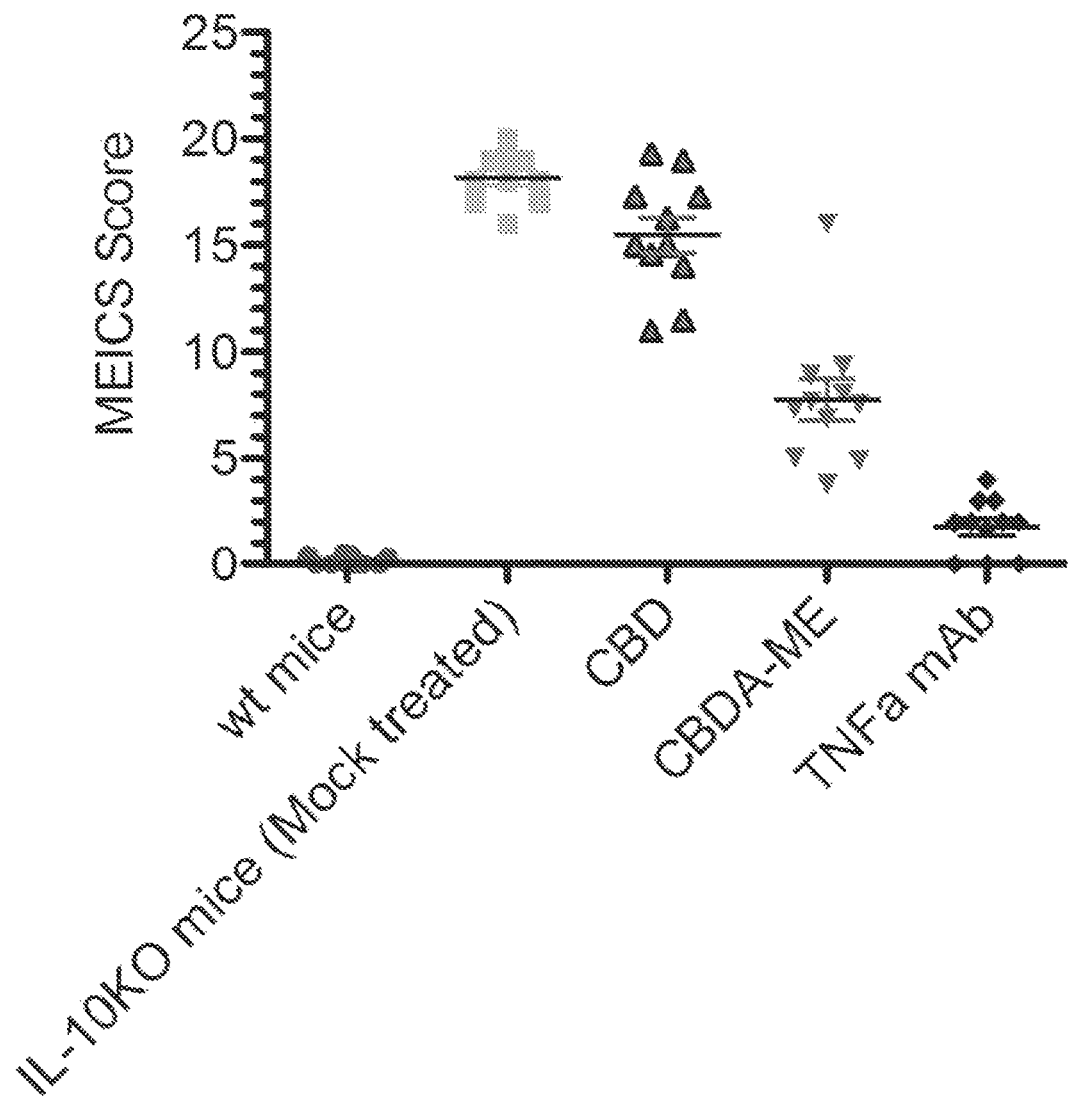
FIG. 16 shows the mouse endoscopic index of colitis severity (MERICS) scoring in mouse models of chronic colitis. MEICS was measured in wild type mice, IL-10KO mice, and IL-10KO mice treated with CBD, CBDA-Me, or TNFα mAb.

Next, the mice were sacrificed and the length of their colons were measured. As shown in FIG. 9, colon length of mice treated with 40 mg/kg CBDA-Me was greater than mice treated with CBD and control (untreated control mice), and similar to prednisone treated mice.

Cytokine levels of IL-6 and TNFα were measured using ELISA kits (R&D Systems, USA). Colon TNFα (FIG. 10), blood IL-6 (FIG. 11), and mouse endoscopic index of colitis severity (METICS) scoring levels (FIG. 12) were lower in mice treated with CBDA-Me compared to CBD. Representative photos of colonoscopy can be seen in FIG. 13A-13E.

Significantly, CBDA-Me exhibited and improved therapeutic effect in acute colitis mouse models. CBDA-Me treatment was superior to CBD.

Example 12—CBDA-Me Efficacy in a Chronic Colitis Model

The therapeutic effect of CBDA-Me on IBD was examined in chronic colitis mouse models.
An Anti-TNF Treatment Model Mice with targeted discruption of the IL-10 gene (IL-10 KO) and littermate wild-type controls (IL-10 WT) were used (see for example Scheinin et al., Clin. Exp. Immunol., 2003, 133:38-43). After 4 weeks of age mice were fed twice a day for 13 weeks with one of the following treatments: CBD, CBDA-Me, an anti-TNF antibody (control), none (untreated control mice). The CBDA-Me efficacy is compared to CBD and controls.

Cytokine levels of IL-1B and TNFα were measured using ELISA kits (R&D Systems, USA). Colon TNFα (FIG. 14), blood IL-1b (FIG. 15), and mouse endoscopic index of colitis severity (MEICS) scoring levels (FIG. 16) were lower in mice treated with CBDA-Me compared to CBD.

Significantly, CBDA-Me exhibited an improved therapeutic effect in chronic colitis mouse models and was found to be superior to CBD.

Example 13—Efficacy Comparison of CBDA-Me and a CBD Derivative Molecule in the Acute Colitis Model The therapeutic effects of CBDA-Me (EPM-301) and a derivative compound (EPM-302) on IBD were examined in an acute colitis mouse model.

Colitis was induced in 10 weeks old female C57BL/6 mice using dextran sodium sulphate (DSS). Mice were fed for 8 days with 2% (wt/vol) DSS in their drinking water. Mice were administered (3 animals in each group) by gavage one of the following treatments by gavage: CBD (40 mg/kg), CBDA-Me (EPM-301, 40 mg/kg), EPM-302 (40 mg/kg), DSS alone (untreated control), prednisone (80 mg/kg, control), none (healthy mice). EPM-302 served as an additional control.

Figure 17:
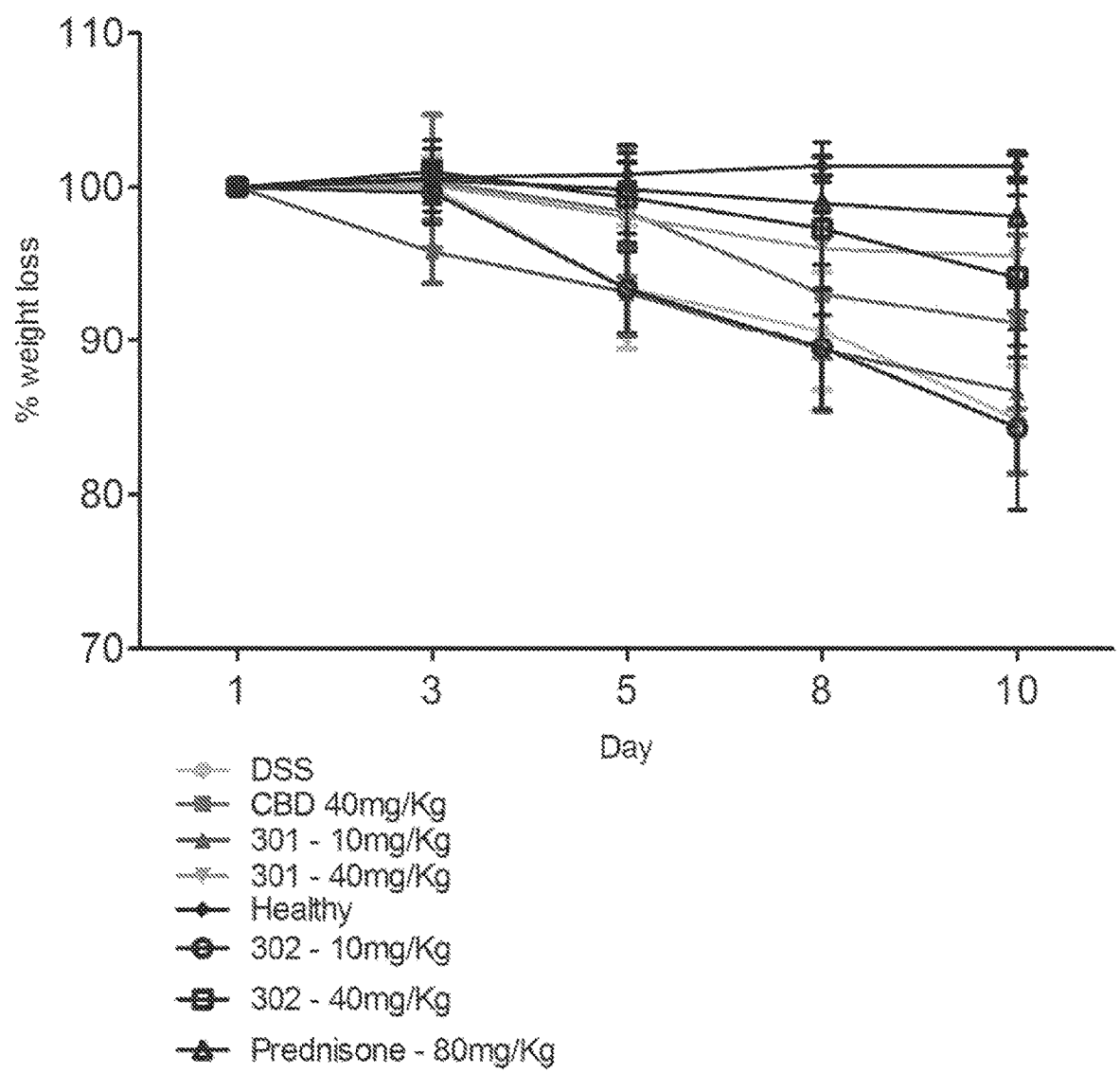
FIG. 17 shows the effect of CBDA-Me on weight loss of mouse models of colitis. Colitis was induced in 10 weeks old female C57BL/6 mice using dextran sodium sulphate (DSS). Mice were treated for 10 days with DSS+CBDA-Me (EPM-301), DSS+EPM-302, DSS+CBD, DSS, DSS+Prednisone, or no DSS (healthy; negative control). Mice weight was measured in days 1, 3, 5, 8, and 10.

Weight loss was measured on days 1, 3, 5, 8, and 10. As shown in FIG. 17, CBDA-Me (EPM-301) treatment resulted in a reduced weight loss compared to CBD and EPM-302 when treated with 40 mg/kg. 10 mg/kg of either CBDA-Me (EPM-301) or EPM-302 were not enough to induce a therapeutic effect.

Figure 18:
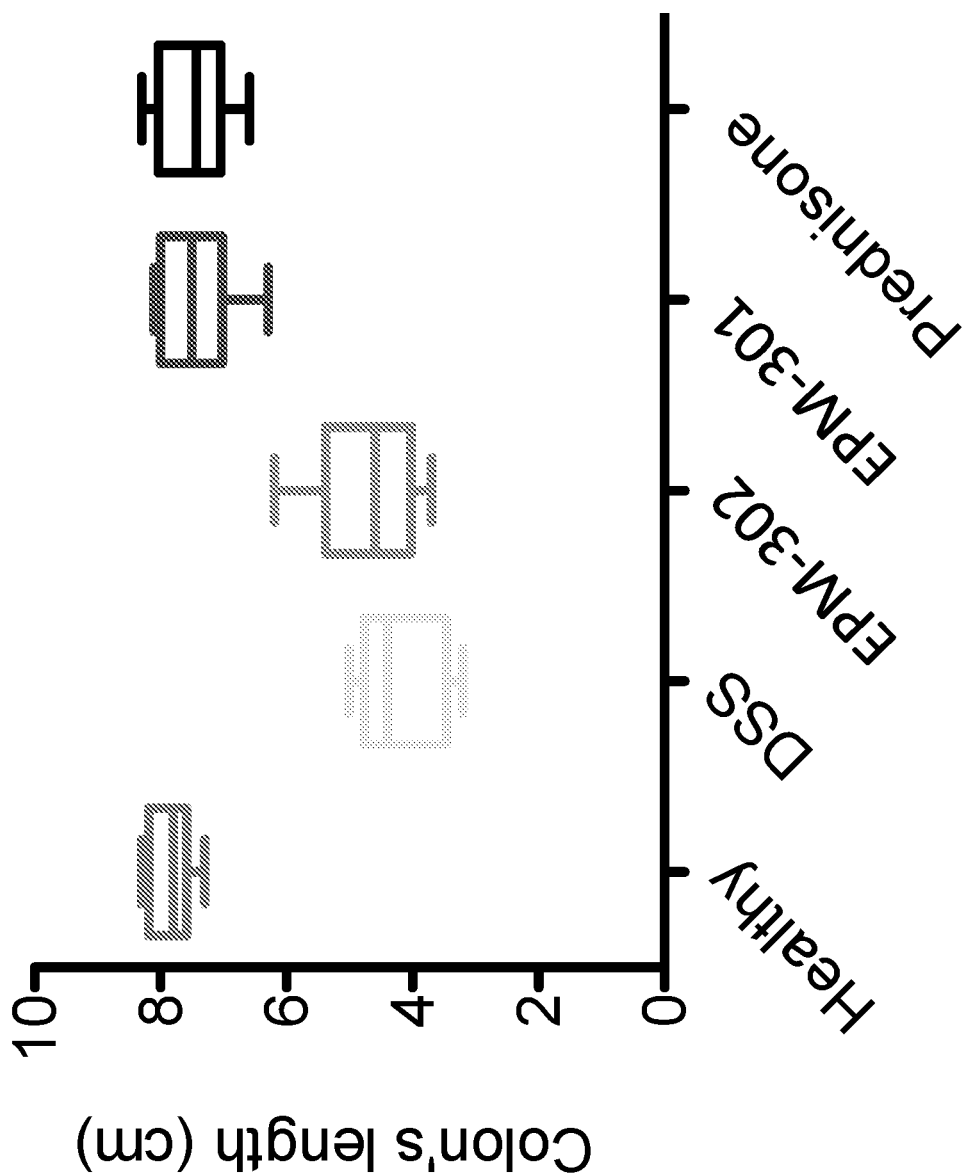
FIG. 18 shows the effects of CBDA-Me (EPM-301) and EPM-302 on colon's length of mouse models of DSS induced colitis.
Figure 19:
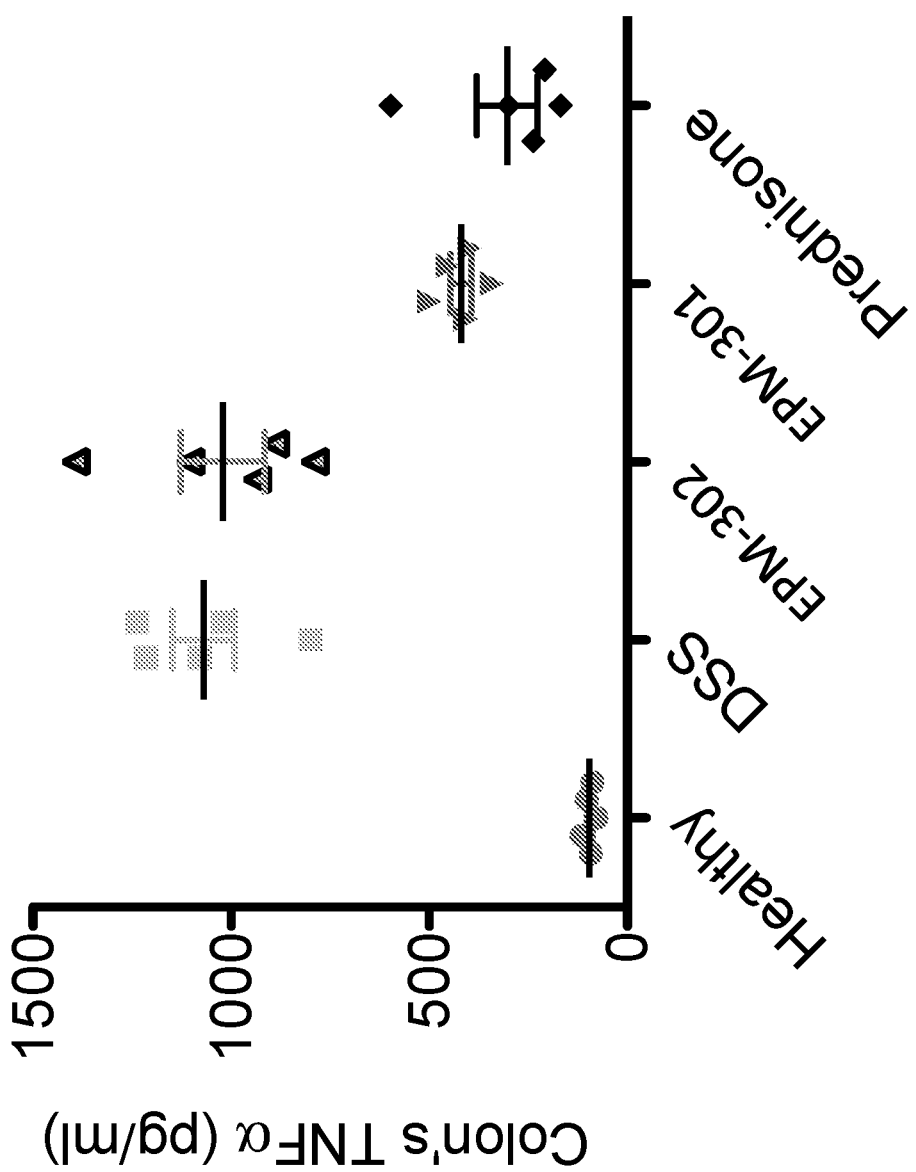
FIG. 19 shows the effects of CBDA-Me (EPM-301) and EPM-302 on TNFα expression in colons of mouse models of DSS induced colitis.
Figure 20:
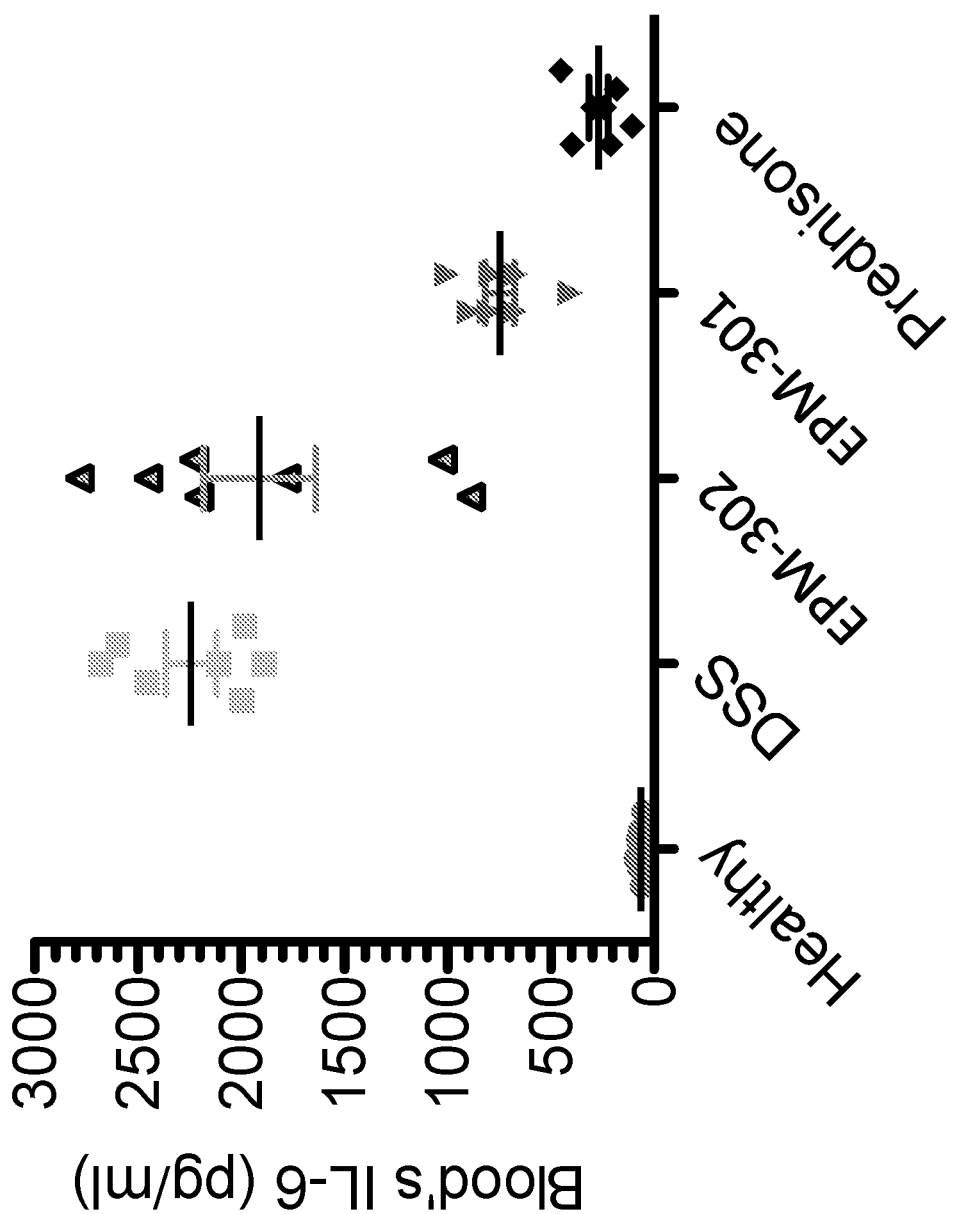
FIG. 20 shows the effects of CBDA-Me (EPM-301) and EPM-302 on IL-6 levels in the blood mouse models of DSS induced colitis.

Next, the mice were sacrificed and the length of their colons were measured. As shown in FIG. 18, colon length of mice treated with 40 mg/kg CBDA-Me (EPM-301) was greater/longer than mice treated with EPM-302 and untreated mice, and similar to prednisone treated mice.

Figure 21:
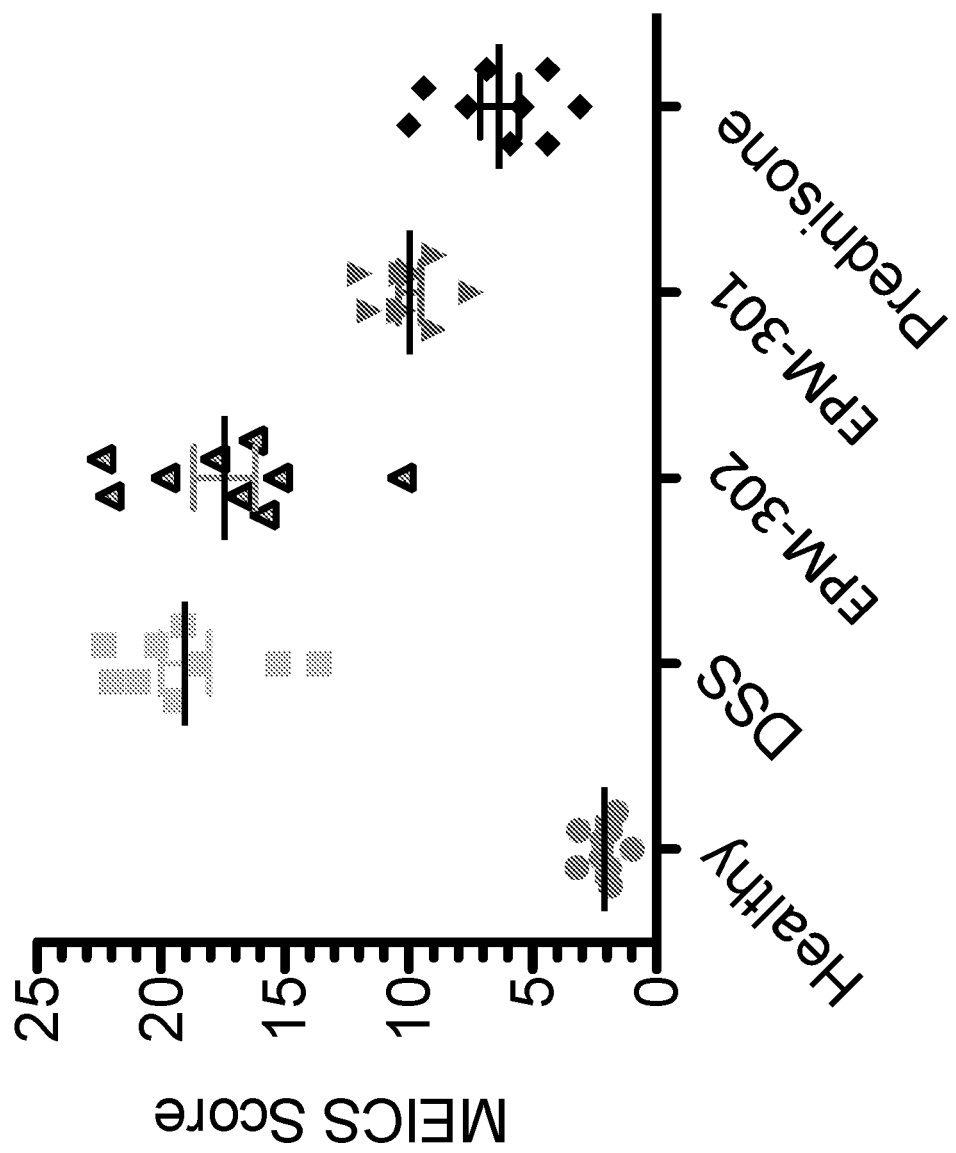
FIG. 21 shows the MEICS scores of experiments conducted with EPM-301, EPM-302, prednisone and controls in the DSS induced colitis model.
Figure 22A:
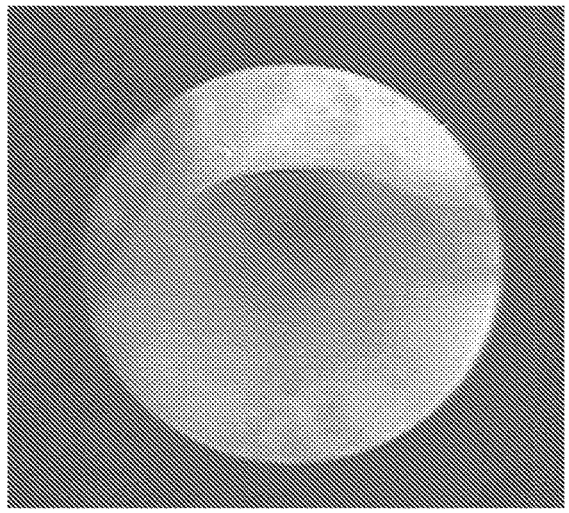
FIG. 22A-22D show the representative colonoscopy photos of mouse models of colitis after treatment with CBD (FIG. 22A), prednisone (FIG. 22B), CBDA-Me (FIG. 22C), or control (FIG. 22D).
Figure 22B:
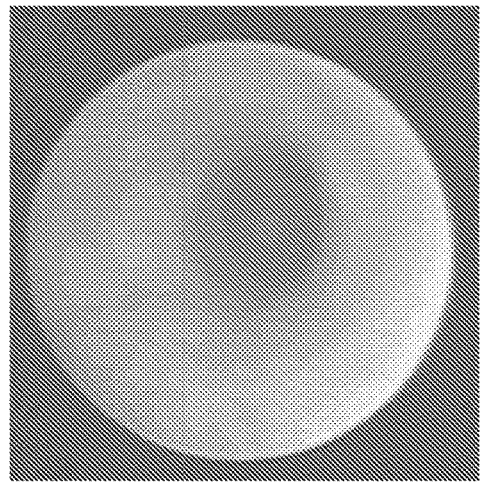
Figure 22C:
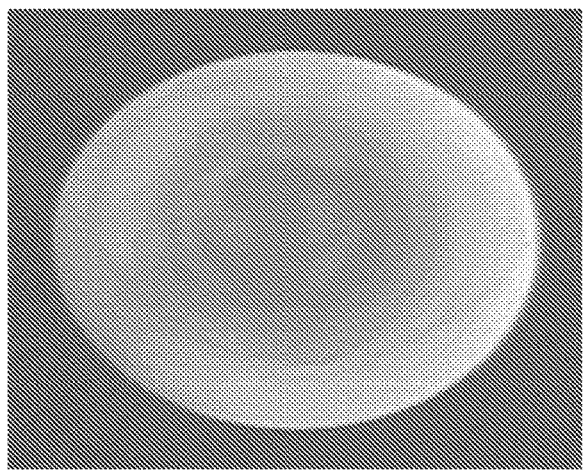
Figure 22D:
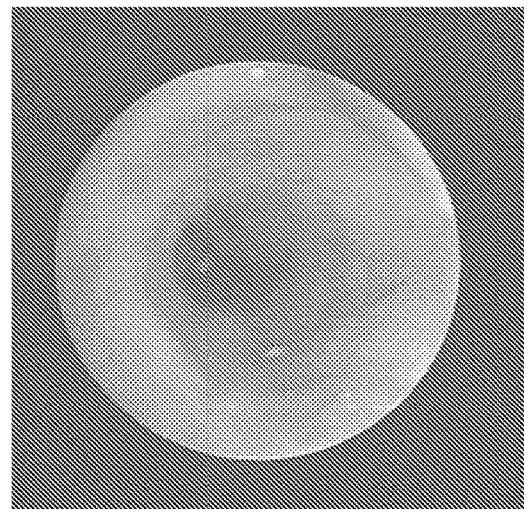
Figure 23:
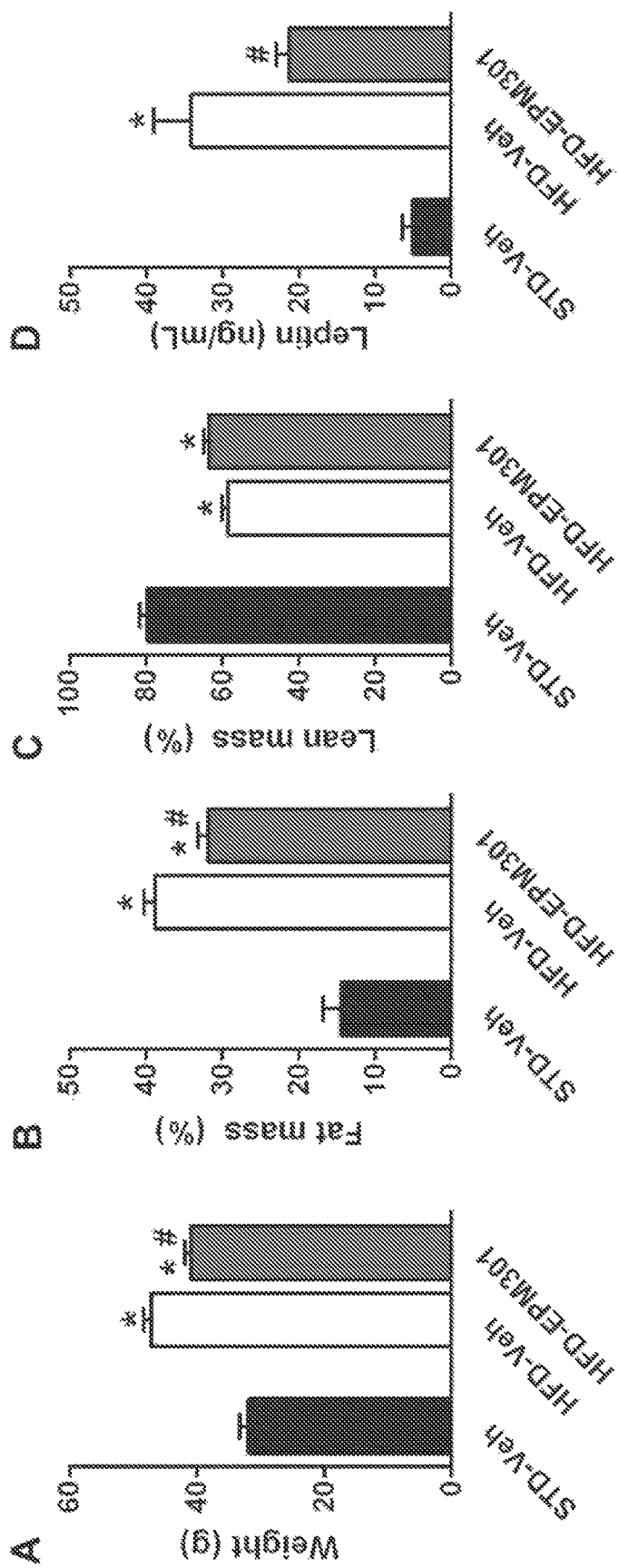
FIG. 23A-23D show the improving effect of CBDA-Me (EPM-301) on weight (FIG. 23A), fat mass (FIG. 23B), body lean mass (FIG. 23C), and leptin levels (FIG. 23D) of mice fed with high-fat diet (HFD)
Figure 24:
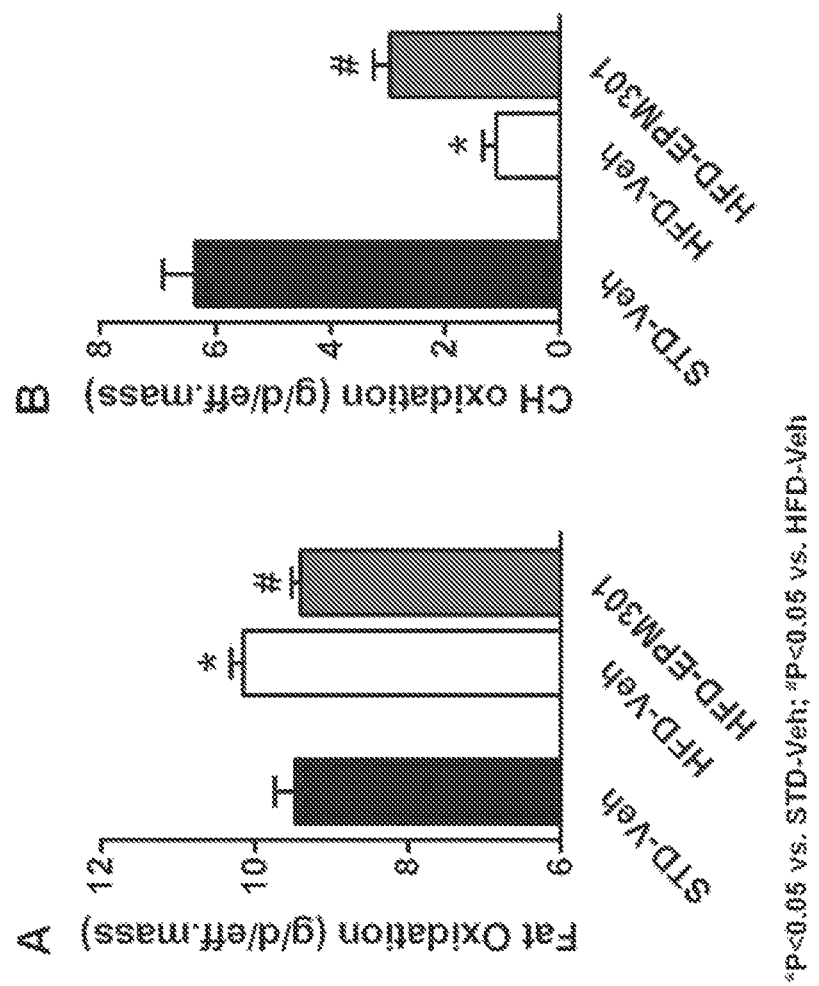
FIG. 24A-24B show the effect of CBDA-Me (EPM-301) on fat oxidation (FIG. 24A) and carbohydrate (CH) oxidation (FIG. 24B) of mice fed with a high-fat diet (HFD)
Figure 25:
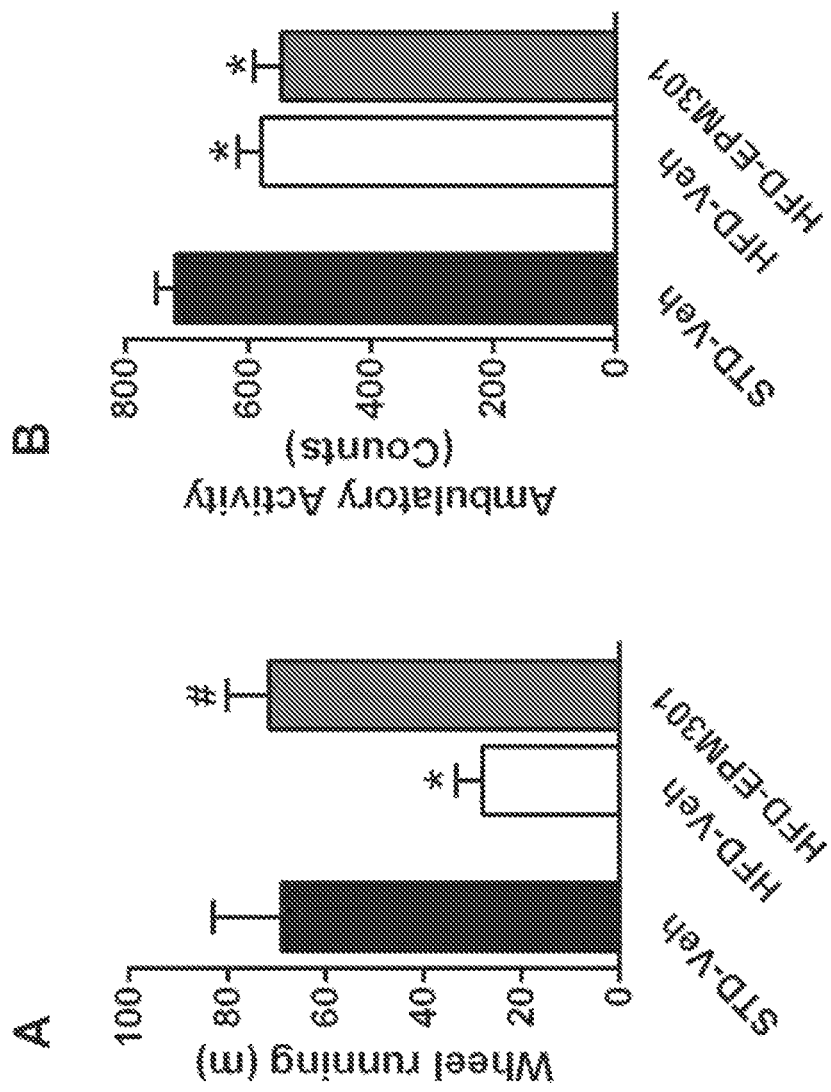
FIG. 25A-25B show the effect of CBDA-Me (EPM-301) on wheel running activity (FIG. 25A) and ambulatory activity (FIG. 25B) of mice fed with a high-fat diet (HFD).
Figure 26:
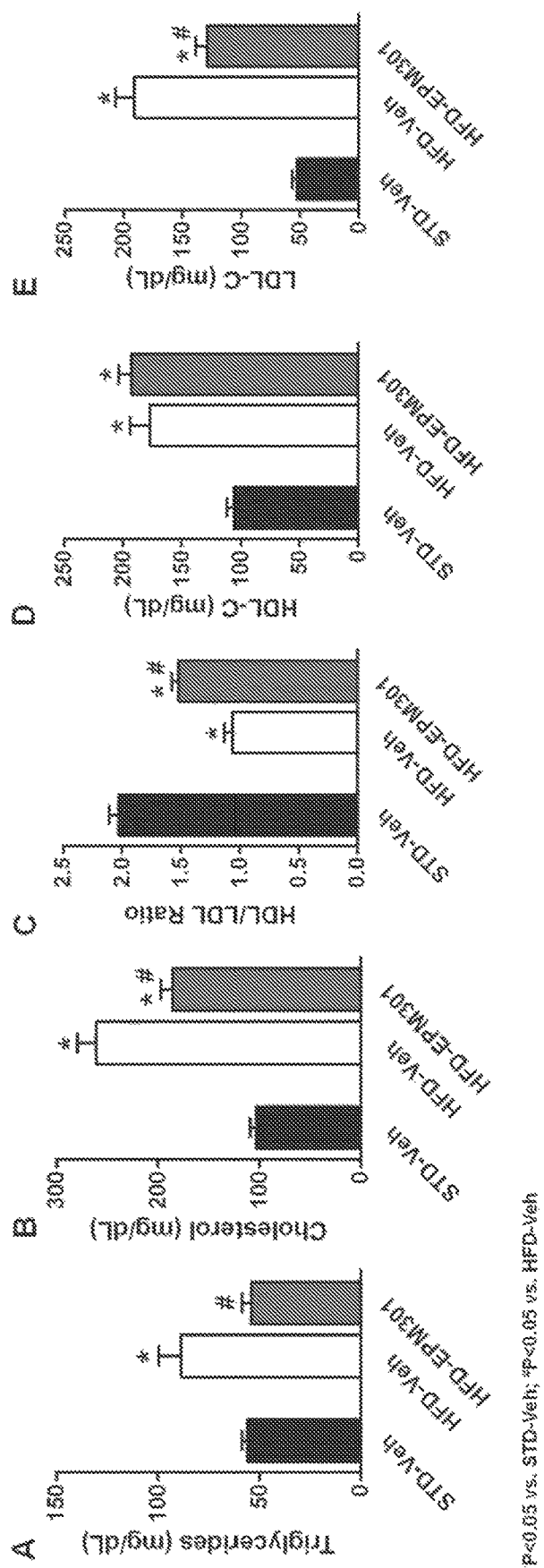
FIG. 26A-26E show the improving effect of CBDA-Me (EPM-301) on triglycerides (FIG. 26A), cholesterol (FIG. 26B), HDL/LDL ratio (FIG. 26C), HDL-C (FIG. 26D), and LDL-C (FIG. 26E) levels of mice fed with a high-fat diet (HFD).
Figure 27:
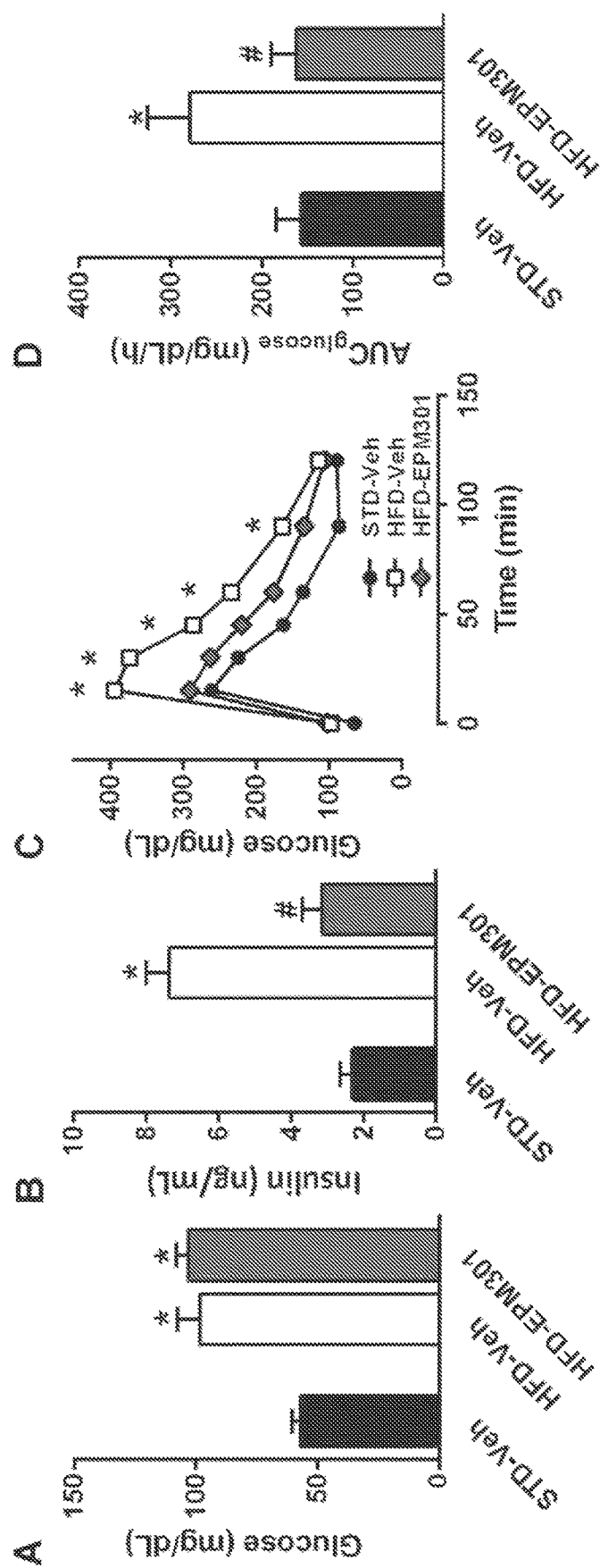
FIG. 27A-27D show the reduction in glucose and insulin tolerance in diet-induced obese DIO mice treated with CBDA-Me (EPM-301). Glucose (FIG. 27A) and insulin (FIG. 27B) levels, glucose level over time (FIG. 27C), and an area under the curve (AUC) of glucose level (FIG. 27C) of mice fed with a high-fat diet (HFD) are presented.
Figure 28:
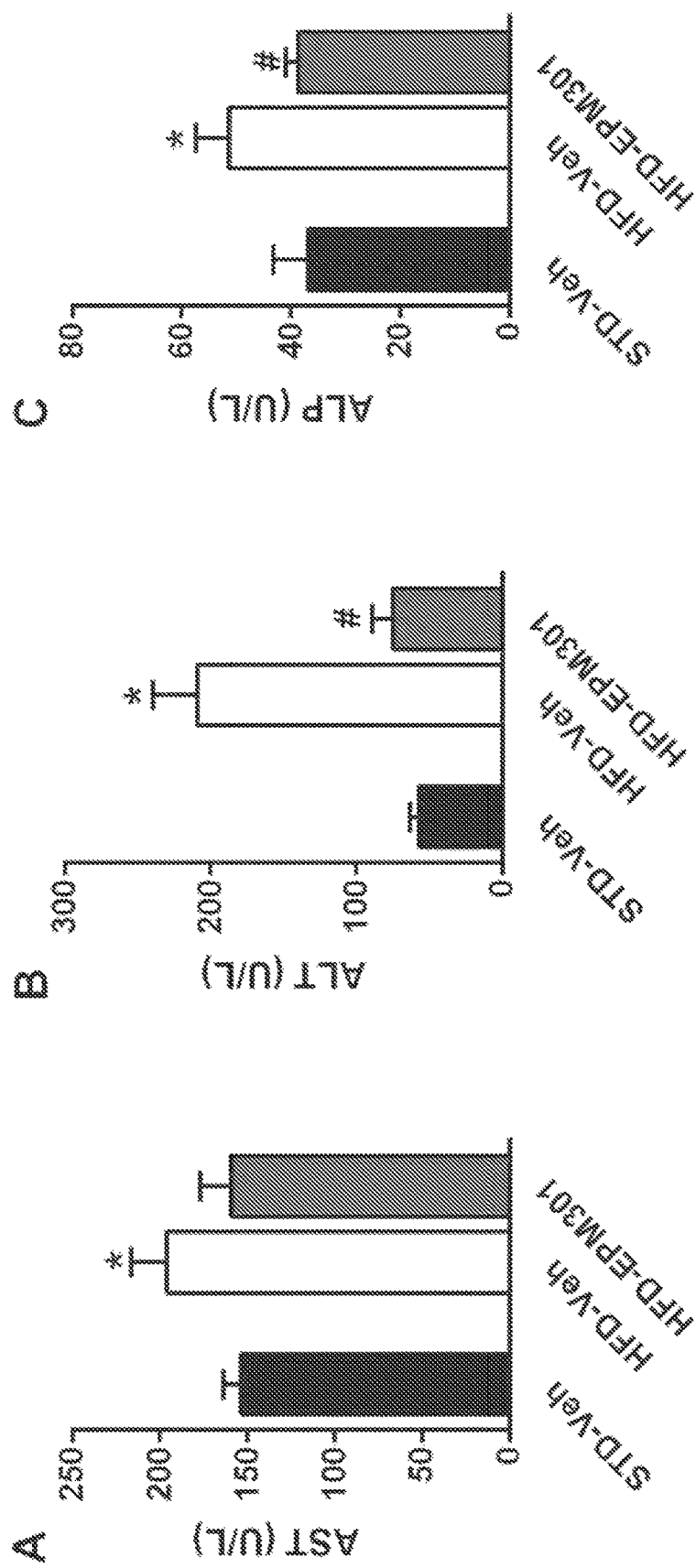
FIG. 28A-28C show the reduction in the serum levels of AST (FIG. 28A), ALT (FIG. 28B), and ALP (FIG. 28C) in diet-induced obese (DIO) mice treated with CBDA-Me (EPM-301).
Figure 29:
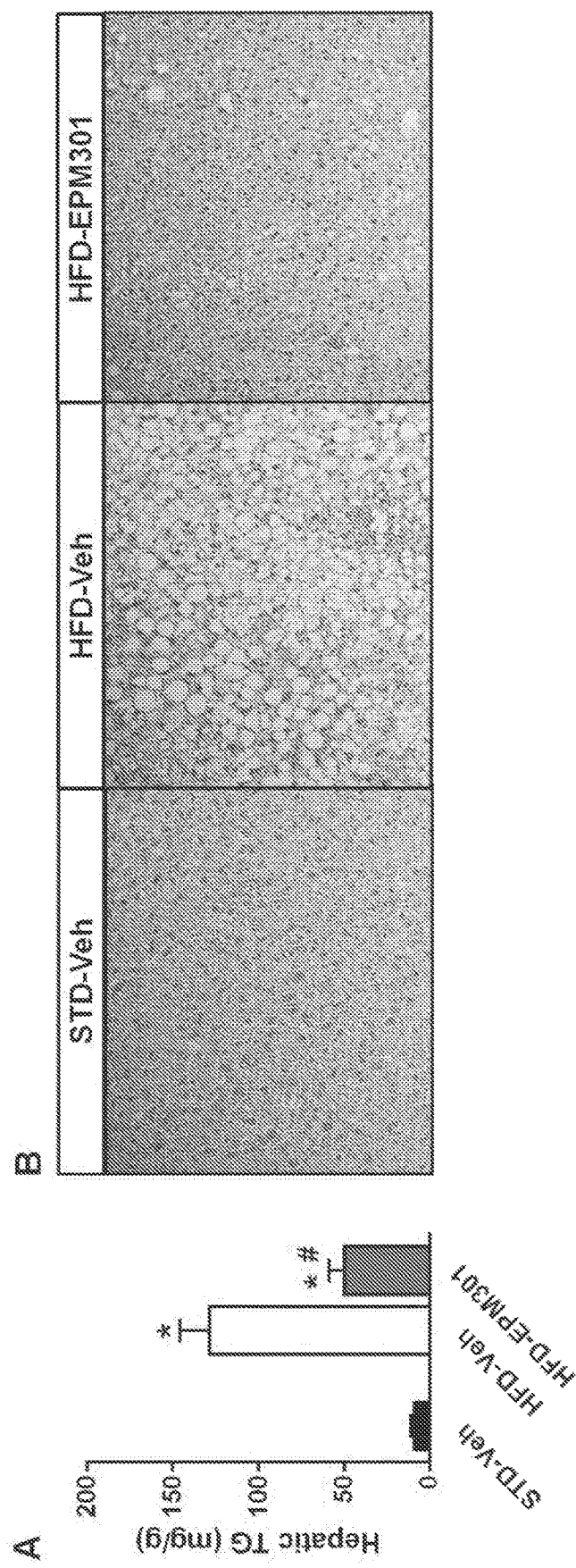
FIG. 29A-29B show the reduction of hepatic triglyceride levels (FIG. 29A) and fat vacuole accumulation (FIG. 29B) in DIO mice treated with CBDA-Me (EPM-301).
Figure 30:
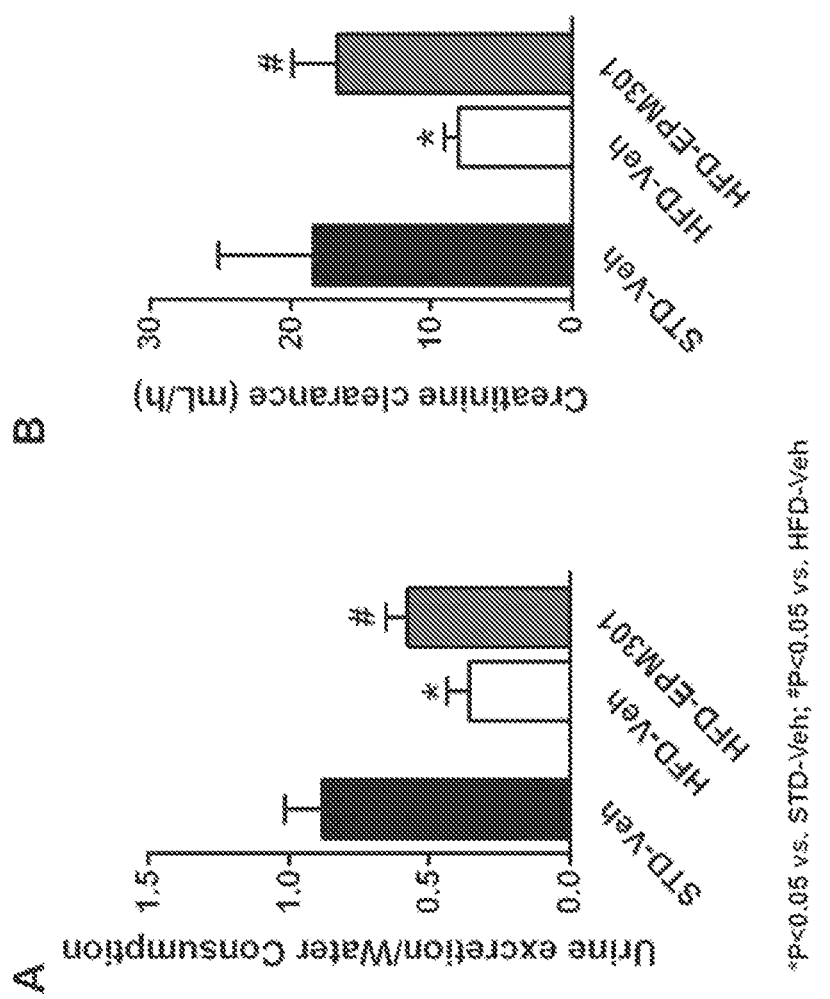
FIG. 30A-30B show the effect of CBDA-Me (EPM-301) treatment on urine excretion (FIG. 30A) and creatinine clearance (FIG. 30B) in DIO mice.

Cytokine levels of IL-6 and TNFα were measured using ELISA kits (R&D Systems, USA). Colon TNFα (FIG. 19), blood IL-6 (FIG. 20), levels were lower in mice treated with CBDA-Me (EPM-301) as compared to EPM-302. Similarly, the MEICS score of EPM-301 treated subjects were also lower than EPM-302 treated subjects (FIG. 21). Representative photos of colonoscopy can be seen in FIG. 22A-22D.

Significantly, CBDA-Me exhibited an improved therapeutic effect in acute colitis mouse models. CBDA-Me (EPM-301) treatment was superior to EPM-302 treatment in this model.

Example 14—In Vitro Model for Testing Efficacy of Treatment of Endometriosis

Cultured cells from Human Endometrial Stromal Cell Line (SHT290) were used. CBDA-Me was added to the medium and the attachment of cells and their proliferation rate were measured. CBDA-Me was shown to decrease the attachment of cells and their proliferation rate in a dose dependent fashion.

Example 15—In Vivo Model for Testing Efficacy of Treatment of Endometriosis

Endometriosis was induced by implantation of rat uterine comu on the mesenterium. The tissue was allowed to proliferate in vivo for 21 days. After 21 days, rats in the control group were injected intra-peritoneally with saline while rats in the experimental group were injected with CBDA-Me. Pain response to oxytocin was measured on day 24. The pain response decreased by 50% in the group treated with CBDA-Me as compared to the control.

Example 16—CBDA-Me Therapeutic Activity Compared to CBD in Hypercholesterolemia

The therapeutic effect of CBDA-Me on cholesterol levels is examined in a mouse model of human familial hypercholesterolemia. Mice are treated with CBDA-Me or CBD followed by measurement of plasma level of cholesterol and triglycerides. The mice are then anesthetized and killed for histological analysis of atherosclerotic lesions and plaques as known in the art.

Example 17—CBDA-Me (EPM-301) Therapeutic Activity in Metabolic and Obesity-Related Disease This example illustrates the therapeutic efficacy of CBDA-Me (EPM-301) in preventing the development of metabolic syndrome in diet-induced obese mice.
Mice and Experimental Design The experimental protocol used was approved by the Institutional Animal Care and Use Committee of the Hebrew University, which is an AAALAC International accredited institute. Male 6-week-old C57Bl/6 mice were obtained from Harlan Laboratories. Mice were maintained under a 12-h light/dark cycle and fed ad libitum. To generate diet-induced obesity, the mice were fed either a high-fat diet (HFD) (60% of calories from fat, 20% from protein, and 20% from carbohydrates; Research Diet, D12492) or a standard laboratory diet (STD, 14% fat, 24% protein, 62% carbohydrates; NIH-31 rodent diet) for 14 weeks.

HFD-fed obese mice received vehicle (1% Tween80, 4% DMSO, 95% Saline) or CBDA-ME daily for 28 days by intraperitoneal (ip) injections of 40 mg/kg. Age-matched control mice on STD received vehicle daily. Body weight and food intake were monitored daily. Total body fat and lean masses were determined by EchoMRI-100H™ (Echo Medical Systems LLC, Houston, Tex., USA). 24 h urine was collected one week before euthanasia using mouse metabolic cages (CCS2000 Chiller System, Hatteras Instruments, NC, USA). At weeks 20, mice were euthanized by a cervical dislocation under deep anesthesia, the kidneys, liver, fat pads, and muscles were removed and weighed, and samples were either snap-frozen or fixed in buffered 4% formalin. Trunk blood was collected for determining the biochemical parameters.

Multi-Parameter Metabolic Assessment

The experimental protocol used Metabolic profile of the mice was assessed by using the Promethion High-Definition Behavioral Phenotyping System (Sable Instruments, Inc., Las Vegas, Nev., USA). Data acquisition and instrument control were performed using MetaScreen software version 2.2.18.0, and the obtained raw data were processed using ExpeData version 1.8.4 using an analysis script detailing all aspects of data transformation. Mice with free access to food and water were subjected to a standard 12 h light/12 h dark cycle, which consisted of a 48 h acclimation period followed by 24 h of sampling. Respiratory gases were measured by using the GA-3 gas analyzer (Sable Systems, Inc., Las Vegas, Nev., USA) using a pull-mode, negative-pressure system. Air flow was measured and controlled by FR-8 (Sable Systems, Inc., Las Vegas, Nev., USA), with a set flow rate of 2000 mL/min. Water vapor was continuously measured and its dilution effect on $O_2$ and $CO_2$ was mathematically compensated. Effective mass was calculated by [body mass]$^{0.75}$. Fat oxidation (FO) and carbohydrate oxidation (CHO) were calculated as FO=1.69×$VO_2$–1.69×$VCO_2$ and CHO=4.57×$VCO_2$–3.23×$VO_2$ and expressed as $g/d/kg^{eff.Mass}$.

Locomotor Activity

Locomotor activity was quantified by the number of disruptions of infrared XYZ beam arrays with a beam spacing of 0.25 cm in the Promethion High-Definition Behavioral Phenotyping System (Sable Instruments, Inc., Las Vegas, Nev., USA).

Glucose Tolerance (ipG77) Test

Mice that fasted overnight were injected with glucose (1.5 g/kg, ip), followed by a tail blood collection at 0, 15, 30, 45, 60, 90, and 120 minutes. Blood glucose levels were determined using the Elite glucometer (Bayer, Pittsburgh, Pa.).

Blood and Urine Biochemistry

Serum and urine levels of creatinine as well as serum levels of cholesterol, triglycerides (TG), high-density lipoprotein (HDL), low-density lipoprotein (LDL), alanine aminotransferase (ALT), aspartate aminotransferase (AST), and alkaline phosphatase (ALP) were determined using the Cobas C-111 chemistry analyzer (Roche, Switzerland) were determined by using the Cobas C-111 chemistry analyzer (Roche, Switzerland). Creatinine clearance was calculated using urine and serum creatinine levels (CCr mL/h=Urine creatinine mg/dL×Urine volume/Serum creatinine mg/dL×24 hrs). Fasting blood glucose was measured using the Elite glucometer (Bayer, Pittsburgh, Pa.).

Hepatic Triglyceride (TG) Content

Liver tissues were extracted as described previously (Tam, J., et al., Cell Metab, 2012. 16(2): p. 167-79) and its triglyceride content was determined using the EnzyChrom™ Triglyceride Assay Kit (BioAssay Systems).

Histopathological Analyses

5 μm paraffin-embedded liver sections from 5 animals per group were stained with hematoxylin-eosin staining. Liver images were captured with a Zeiss AxioCam ICc5 color camera mounted on a Zeiss Axio Scope.A1 light microscope and taken from 10 random 40× fields of each animal.

Cellular Lipid Accumulation Test

To test whether CBDA-ME has the ability to reduce lipid accumulation in renal proximal tubule cells, we have utilized an in vitro model of fat accumulation in LLCPK1 cells. Briefly, LLCPK1 cells were maintained at 37° C. in 5% $CO_2$ in DMEM medium supplemented with 10% FCS, 2 mM 1-glutamine, 1 mM sodium pyruvate, 100 U/mL penicillin and 100 mg/mL streptomycin. Free fatty acids (2:1, molar ratio, oleic and palmitic acids) were mixed with bovine serum albumin (BSA). Cells were incubated with fatty acid-BSA complex in FCS-free culture medium at 0.3 mM final concentration of fatty acid and 1% of BSA. Control cell cultures were incubated with medium containing the vehicle. Compounds were tested in a range of concentrations (as detailed in the results section) in the presence/absence of fatty acids. After 24 hr of incubation with the compounds, the cells were washed, incubated with 1 μg/mL mixture of Nile-Red/Hoechst solution for 15 mins at 37° C. protected from light. Fluorescence was measured by the Cytation-3 plate reader at ex:488 nm/em:550 for Nile-Red and Hoechst, respectively. Results were normalized to total protein levels of each well, and presented as a change in the accumulation of lipids in comparison with Vehicle-treated group.

Results

The metabolic profile of EPM-301 was examined in mice with diet-induced obesity (DIO). Male C57BL/6 mice fed a high-fat diet (HFD) for 14 weeks became obese and were then started on daily ip injections of vehicle, or EPM-301 (40 mg/kg/d) for an additional 28 days. Age- and sex-matched mice on STD served as controls. The overweight and increased adiposity of mice on HFD were significantly reduced by EPM-301 (FIG. 23A-23B), without affecting lean body mass (FIG. 23C). These effects were also associated with the reduction in leptin levels of the tested subjects (FIG. 23D).

Significant changes in the metabolic profile of the DIO mice treated with EPM-301 were demonstrated using an indirect calorimetry assessment. As shown in FIG. 24A-24B, EPM-301 was able to downregulate the utilization of fat and upregulate carbohydrate oxidation similar to lean mice on STD.

The metabolic improvements of DIO mice treated with EPM-301 were associated with the increased ability of the obese mice to run on a wheel similar to STD-fed animals (FIG. 25A, similar to STD-fed animals), without changing their total ambulatory activity (FIG. 25B).

The reduction in body weight in DIO mice treated with EPM-301 resulted in improvement in lipid profile, in which the HFD-induced hypertriglyceridemia (FIG. 26A) and hypercholesterinemia (FIG. 26B) were significantly reduced. Increased ratio between HDL to LDL was also noted in the treated mice (FIG. 26C), as a result of reduced LDL-cholesterol (FIG. 26D) without changing HDL-cholesterol (FIG. 26E).

Whereas no change in fasting glucose levels was found (FIG. 27A), a significant reduction in glucose intolerance in DIO mice treated with EPM-301 was documented (FIG. 27B-27D).

EPM-301 significantly reduced the obesity related hepatocellular injury, as documented by the reduction in the serum levels of ALP (FIG. 28A), ALT (FIG. 28B), and AST (FIG. 28C). Similarly, the HFD-induced hepatic steatosis, as reflected by the elevated triglyceride levels (FIG. 29A) as well as the increased fat vacuoles in the liver, was completely attenuated by EPM-301 (FIG. 29B).

In addition, the HFD-induced kidney hypofiltration as well as the reduction in urine excretion-to-water consumption ratio were completely normalized by EPM-301 (FIG. 30A-30B), suggesting increased ability of the compound to ameliorate obesity-induced renal dysfunction.

Figure 31:
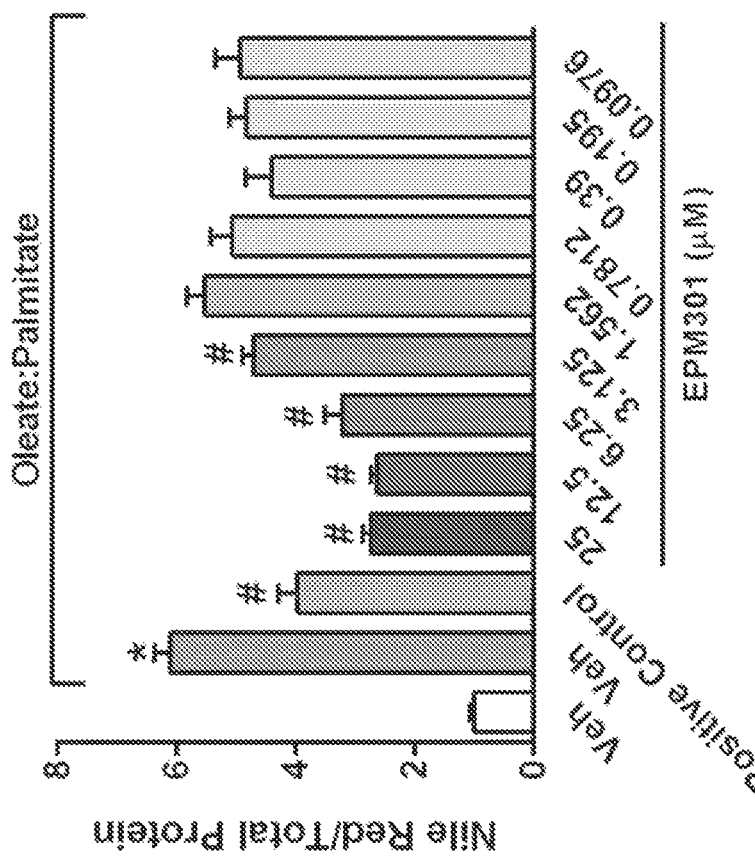
FIG. 31 shows that CBDA-Me (EPM-301) reduces lipotoxicity in a cellular-based assay in kidney cells.

In parallel improvement of kidney function by EPM-301, the ability of EPM-301 to reduce lipotoxicity was then tested in a cellular-based assay in kidney cells. EPM-301 (3.125-25 μM) was able to prevent fat accumulation in cells exposed to a mixture of oleate and palmitate (FIG. 31).

In conclusion, EPM-301 demonstrates an impressive ability to prevent or mitigate various metabolic conditions by (i) ameliorating weight gain; (ii) preventing body and liver fat storage; (iii) preserving normal glucose homeostasis; and (iv) preserving kidney and liver function.

Example 18—the Effect of Intra-Peritoneal (i.p.) Injections of CBDA-Me (EPM-301) in a Rat Model of Diet Induced Obesity This example illustrates the testing and comparison of CBDA-Me (EPM-301) therapy on weight gain in rats with an adipogenic diet.

Study Background

Adiposity is a modern world pandemic due mainly to changes in food composition and nutritional values as well as availability. There is an interest in developing a medication that can reduce weight gain or even causing weight loss. While previous studies have suggested that marijuana use is associated with weight gain in humans (Greenberg et al. *Psychopharmacology* (*Berl*). August 1976; 49(1), 79-84) there are some indications that activation of the endocannabinoid system leads to growth retardation and reduces weight (Fujimoto et al. *Pharmacology* 1982; 24(5), 303-313). The current study attempted to assess the effect of EPM301 on weight gain in rats.

Study Design

The study was designed as a N-of-1 study, where each animal served as its own control. The advantage of this model is the elimination of the need for a control group and reduction of intra-animal variation. The study was performed in two phases: a short-term study with one week exposure to EPM-301 and a long-term study with 8 weeks exposure to EPM-301 (injected daily). In the long-term study, a control group was used including animals fed the adipogenic diet.

Test and Control Articles

EPM-301 was dissolved in 1:1:18 EtOH:cremophor:seline solution to final concentration of 3.5 mg/ml.

Test and Control Articles Administration

In the short-term experiment, all rats were injected i.p. 150 uL in the first day, and after a 3-day break were then injected i.p. every day for 4 days. In the long-term experiment i.p. injections of 150 uL were carried out daily for 8 weeks. Weight was measured at weeks 0, 1, 3, and 9 after injections.

Description of Test System

The rats were weighed on a digital weight weekly in the short-term study for 3 weeks. The rats were weighed on weeks 0, 1, 3, and 9 in the long-term study.

Description of Methods

Rats were allowed to acclimatize for 1 week, and then their weights were assessed using a digital weighing machine. Animals are fed an adipogenic diet for two weeks before starting injections. The diet was Teklad TD95217 as shown in FIG. 32.

Statistical Methods

The weights of the animals were compared at each time point and the change over time calculated. ANOVA was used to determine whether there was a significant change. Post-hoc analyses included the Scheffe all-contrast analysis.

Storage Locations

The animals were treated in a GCP—approved facility. The EPM301 was stored as 70 mg/ml stock dissolve in EtOH in a temperature monitored refrigerator at 4 degrees Celsius.

Results

Figure 33:
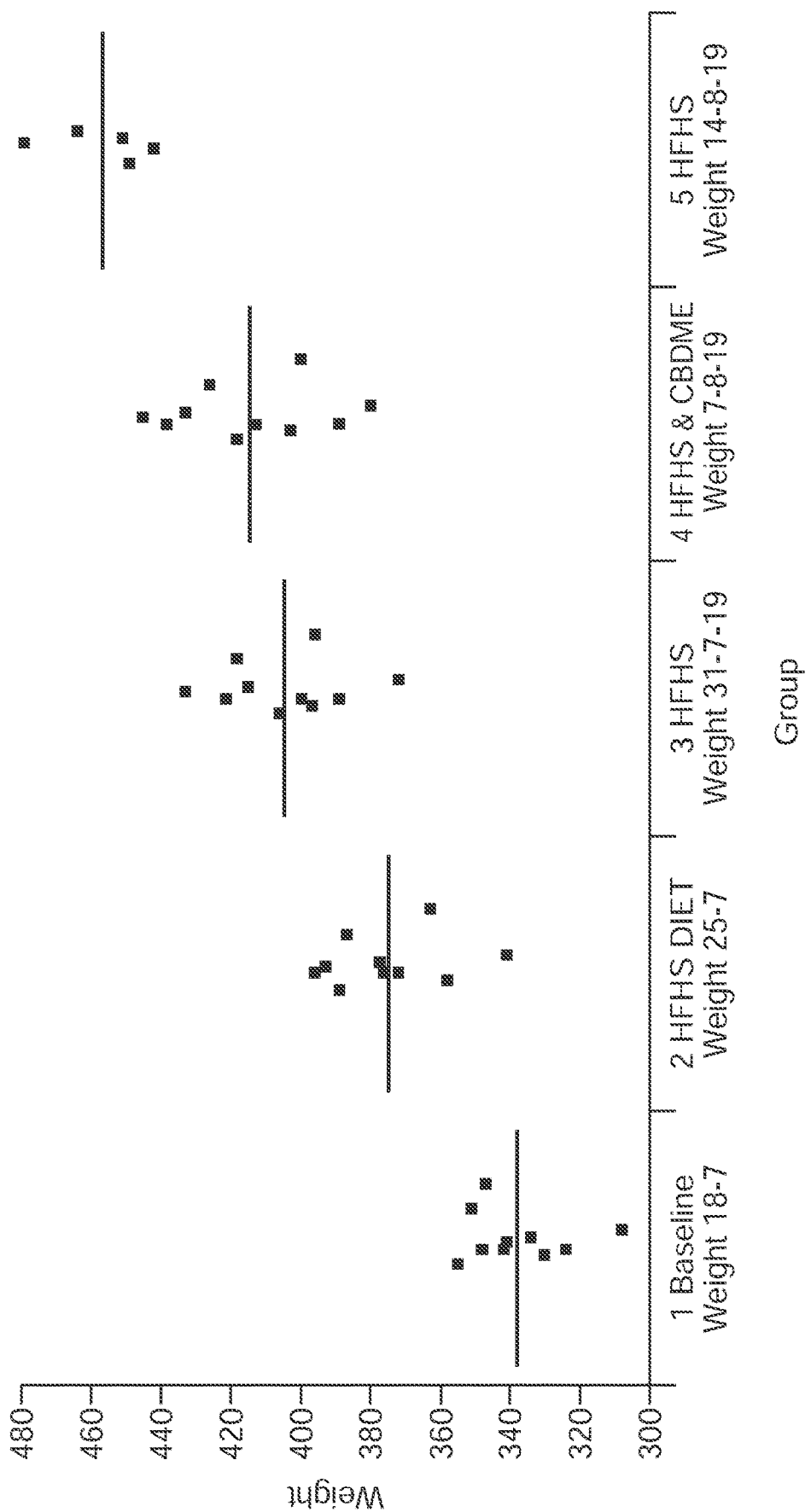
FIG. 33 shows the short-term effect of CBDA-Me (EPM-301) on weight gain of rat subjects being fed with the TD.95217 diet.
Figure 34:
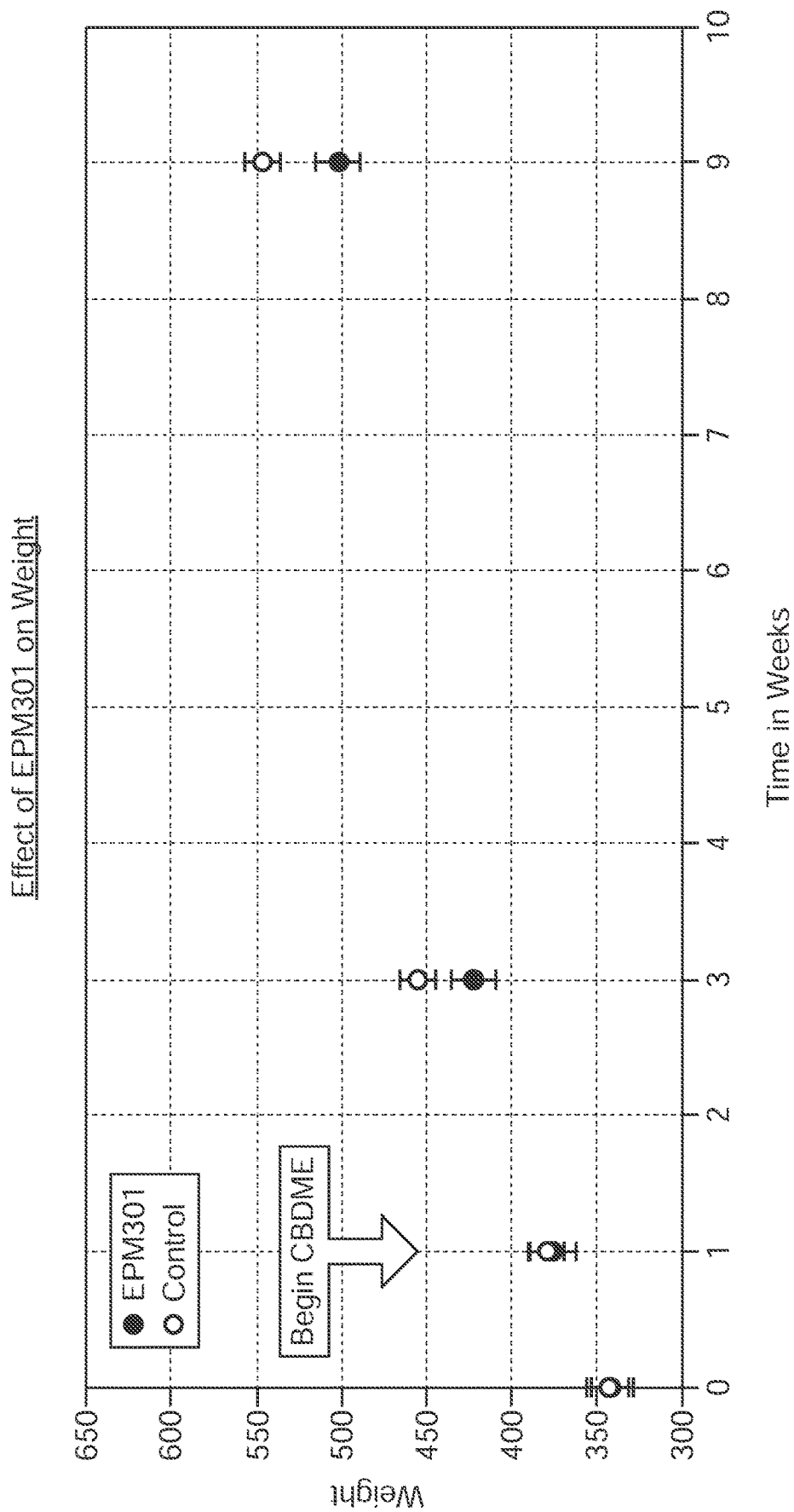
FIG. 34 shows the long-term effect of CBDA-Me (EPM-301) on weight gain of rat subjects being fed with the TD.95217 diet.

In the short-term study, the tested rat subjects gained weight rapidly under the Teklad TD95217 diet. Administration of EPM-301 injections led to halting of weight gain, and stoppage of the EPM-301 injections restored weight gain, as shown in FIG. 33 and FIG. 34.

Figure 35:
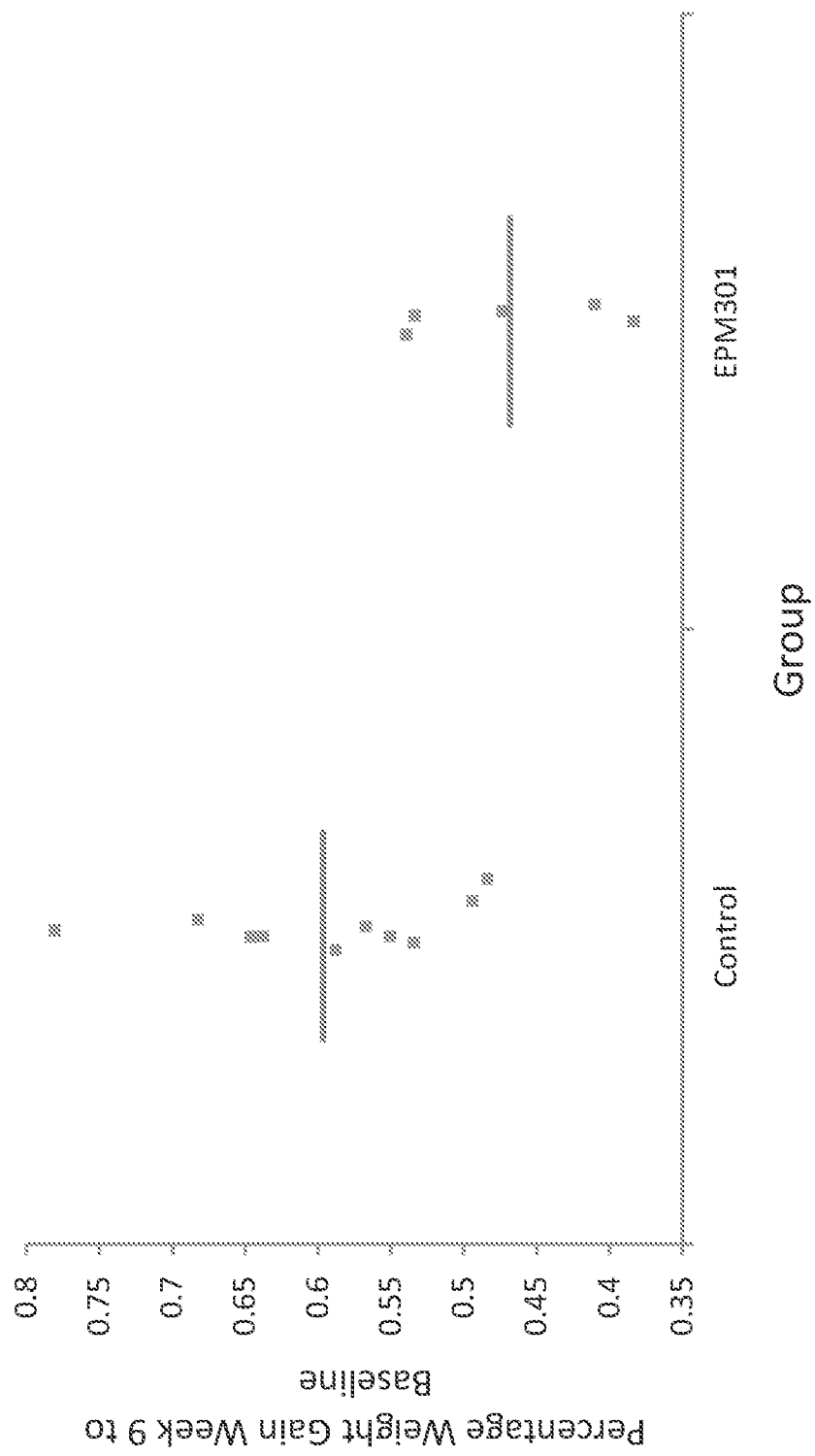
FIG. 35 shows the percentage weight gain from baseline to end of the long-term study of CBDA-Me (EPM-301) treated group versus the control group.

When the percentage weight gain from baseline to end of the long-term study (week 9 of fattening diet and 8 weeks of EPM-301 therapy), the different between the control group and the EPM-301 treated group was found to be significant, as shown in FIG. 35.

Conclusion

EPM-301 was shown to prevent weight gain in rats fed with an adipogenic diet in both short-term and long-term studies.

Example 19—Effects of CBDA-Me (EPM-301) and a CBDA-Me Derivative (EPM-302) in Regulating Glucose Uptake This example illustrates the therapeutic potential of two cannabinoid acid ester compounds (EPM-301 and EPM-302) in regulating glucose uptake in HEK293 cells.

Study Design, Protocols, and Materials

In vitro assays for measuring glucose uptake were designed to assess whether EPM-301 and EPM-302 compounds are capable of inhibiting or increasing glucose uptake via glucose transporters (GLUTs).

Transfected HEK293t cells, which express the glucose transporter 2 (GLUT2), were cultured in a 96 well plate and maintained at 37° C. in 5% $_{CO2}$ in DMEM medium supplemented with 10% FCS, 2 mM l-glutamine, 1 mM sodium pyruvate, 100 U/mL penicillin, and 100 mg/mL streptomycin for 24 h. The medium was then washed with a choline chloride $Na^+$-free buffer (CCB), in which only GLUTs (and not the sodium/glucose transporters [SGLTs]) were active. The wells were then added with CCB/CCB+2-NBDG (a fluorescent derivative of glucose). Compounds were tested in a range of concentrations for their ability to inhibit/increase 2-NBDG uptake into the cells. After 1.5 h incubation, cells were washed with CCB and incubated with 1 μg/μL of Hoechst for 15 mins at 37° C. and protected from light. Fluorescence was measured by the Cytation-3 plate reader at ex:485 nm/em:528 nm and ex:350 nm/em:461 nm for 2-NBDG Hoechst, respectively. Results of the 2-NBDG levels were normalized to Hoechst levels of each well, and presented as a change in the uptake of 2-NBDG in comparison with Vehicle-treated group.

Vehicle solution (choline chloride buffer), EPM-301 (50-0.1 μM), and EPM-302 (50-0.1 μM) were used for the experiments.

Values are expressed as mean±SEM. Unpaired two-tailed student's t-test was used to determine the differences between the groups. Significance was set at p<0.05. *versus vehicle; #versus control.

Test compounds were stored in −20° C. until used for the experiments.

Results

Figure 36:
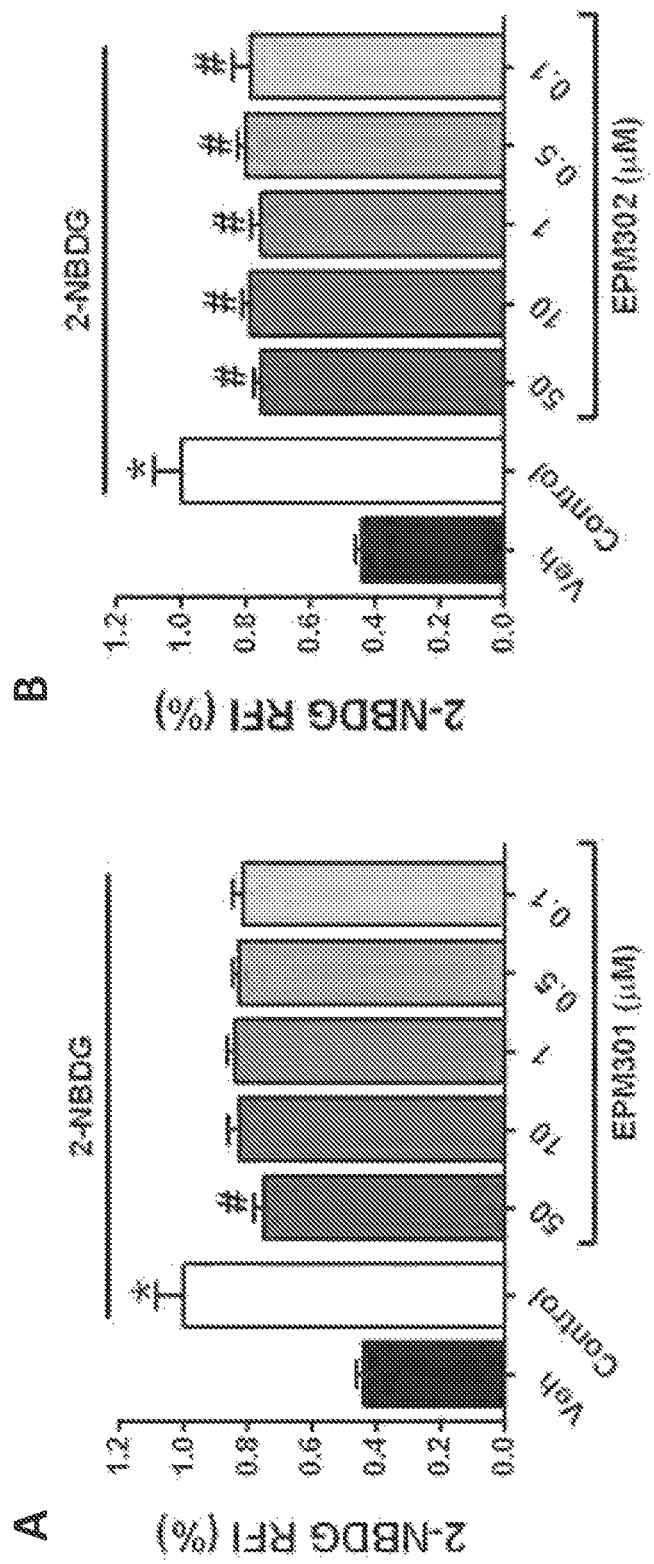
FIG. 36 shows the effects of CBDA-Me (EPM-301) (FIG. 36A) and EPM-302 (FIG. 36B) on regulating glucose uptake into HEK293 cells at various concentrations as compared to control groups.

Experimental results showed that EPM-301 and EPM-302 were able to significantly reduce glucose uptake in HEK293 cells, as shown in FIG. 36A and FIG. 36B. Furthermore, whereas the effect of EPM-301 on glucose transport was observed only with high concentration (50 µM) of the dose, the effect of EPM-302 on glucose transport was observed in all concentrations tested.
Conclusion It was demonstrated that both EPM-301 and EPM-302 are capable of reducing glucose transport in kidney cells.

Example 20—Effects of CBDA-Me (EPM-301) and a CBDA-Me Derivative (EPM-302) in Ameliorating Fat Accumulation in Hepatocytes This example illustrates the therapeutic potential of two cannabinoid acid ester compounds (EPM-301 and EPM-302) in ameliorating fat accumulation in hepatocytes.
Study Design, Protocols, and Materials An in vitro model of fat accumulation in hepatocytes was used to test whether compounds EPM-301 and EPM-302 have the ability to reduce lipid accumulation in hepatocytes Human hepatoma HepG2 cells were maintained at 37° C. in 5% $CO_2$ in DMEM medium supplemented with 10% FCS, 2 mM 1-glutamine, 1 mM sodium pyruvate, 100 U/mL penicillin and 100 mg/mL streptomycin. Free fatty acids (2:1, molar ratio, oleic and palmitic acids) were mixed with bovine serum albumin (BSA). Cells were incubated with fatty acid-BSA complex in FCS-free culture medium at 0.3 mM final concentration of fatty acid and 1% of BSA. Control cell cultures were incubated with medium containing the vehicle. Compounds were tested in a range of concentrations in the presence of fatty acids. After 24 hr of incubation with the compounds, the cells were washed, incubated with 1 µg/mL mixture of Nile-Red/Hoechst solution for 15 mins at 37° C. protected from light. Fluorescence was measured by the Cytation-3 plate reader at ex:488 nm/em:550 nm and ex:350 nm/em:461 nm for Nile-Red and Hoechst, respectively. Results were normalized to total protein levels of each well, and presented as a change in the accumulation of lipids in comparison with Vehicle-treated group.

Vehicle (2:1 UPDDW: 11% BSA (free fatty acid) in DDW), EPM-301 (10-0.001 µM), and EPM302 (10-0.001 µM) were used. EPM-301 at 50 µM was used as positive control.

Values are expressed as mean±SEM. Results in multiple groups were compared by ANOVA followed by a Tukey's multiple comparison test. Significance was set at $P<0.05$. *versus vehicle in the absence of O:P; #versus vehicle in the presence of O:P.

Test compounds were stored at −20° C. until used for the experiments.
Results

Figure 37:
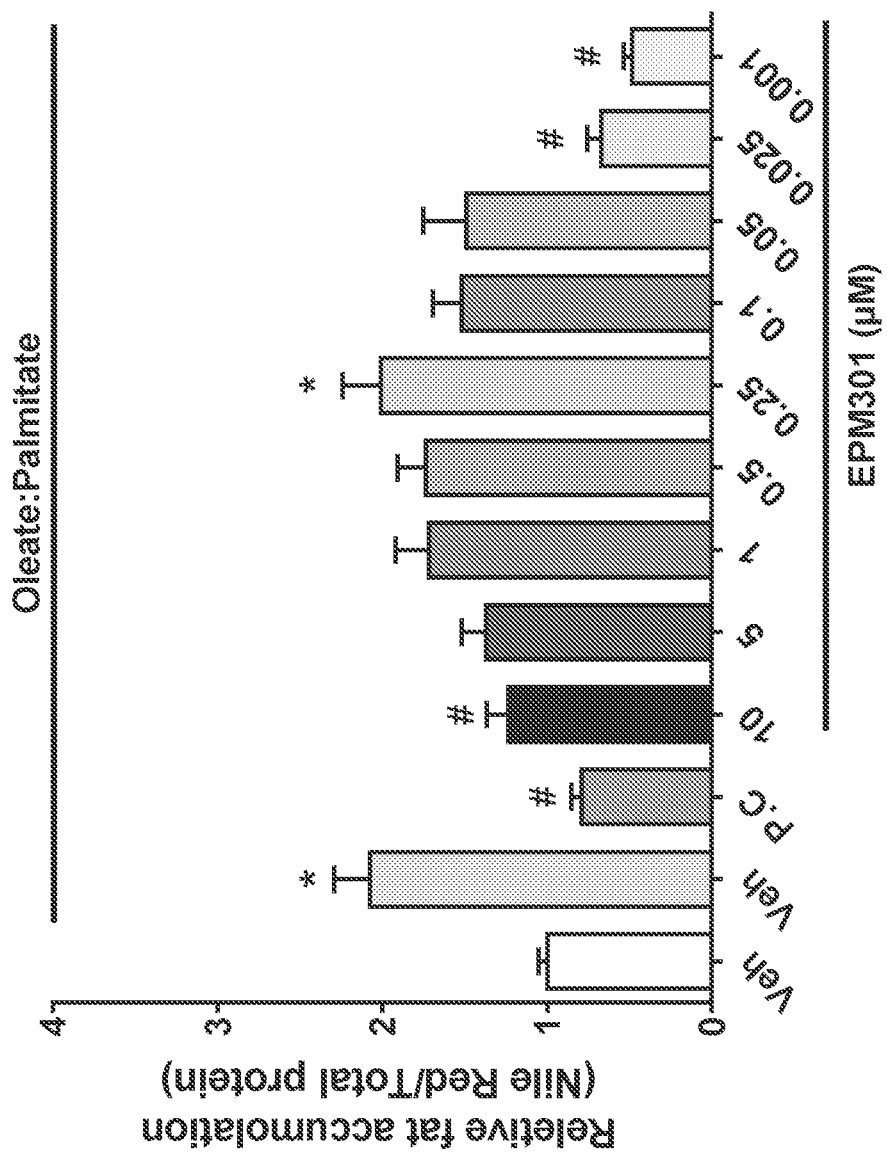
FIG. 37 shows the effect of CBDA-Me (EPM-301) on reducing the amount of fat accumulation in hepatocytes at various concentrations as compared to control groups.

It was shown that EPM-301 was able to significantly reduce the amount of fat accumulation in hepatocytes at high (50 and 10 µM) and low (0.025 and 0.001 µM) concentrations. A bell-shaped effect was demonstrated with EPM-301 (FIG. 37). Each concentration was repeated between 8-32 times.

Figure 38:
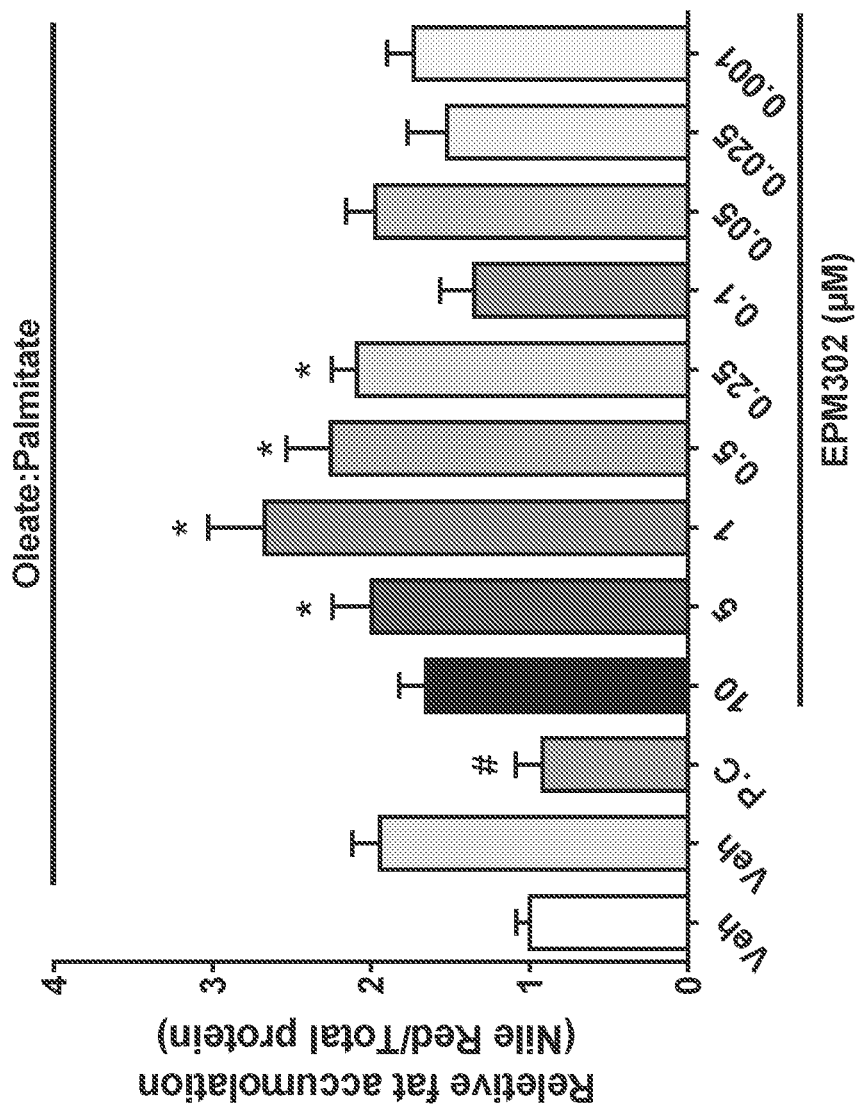
FIG. 38 shows the effect of EPM-302 on reducing the amount of fat accumulation in hepatocytes at various concentrations as compared to control groups.

It was shown that EPM-301 was ineffective in reducing the amount of fat accumulation in hepatocytes, as shown in FIG. 38. Each concentration was repeated between 8-16 times.
Conclusion It was demonstrated in this experiment that EPM-301 is effective in reducing fat accumulation in hepatocytes.

EQUIVALENTS AND INCORPORATION BY REFERENCE

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are herein incorporated by reference in their entirety, for all purposes.

The invention claimed is:

1. A pharmaceutical composition comprising a cannabinoid acid ester compound of formula (Ib):

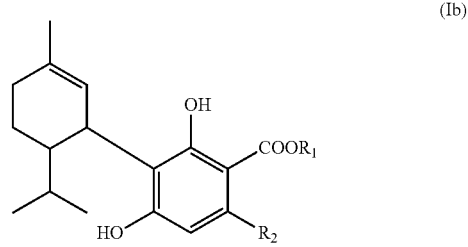

wherein $R_1$ and $R_2$ are independently selected from $C_1$-$C_{10}$ alkyl, substituted $C_1$-$C_{10}$ alkyl, $C_2$-$C_{10}$ alkenyl, substituted $C_2$-$C_{10}$ alkenyl, $C_2$-$C_{10}$ alkynyl, and substituted $C_2$-$C_{10}$ alkynyl, or a pharmaceutically acceptable salt thereof, and a pharmaceutically acceptable excipient.

2. The pharmaceutical composition of claim 1, wherein $R_1$ is $C_1$-$C_6$ alkyl or substituted $C_1$-$C_6$ alkyl.

3. The pharmaceutical composition of claim 1, wherein $R_1$ is methyl.

4. The pharmaceutical composition of claim 1, wherein $R_2$ is $C_1$-$C_{10}$ alkyl, or substituted $C_1$-$C_{10}$ alkyl.

5. The pharmaceutical composition of claim 1, wherein $R_2$ is $C_{2-6}$ alkyl.

6. The pharmaceutical composition of claim 1, wherein $R_2$ is pentyl.

7. The pharmaceutical composition of claim 1, wherein the compound is of formula (V):

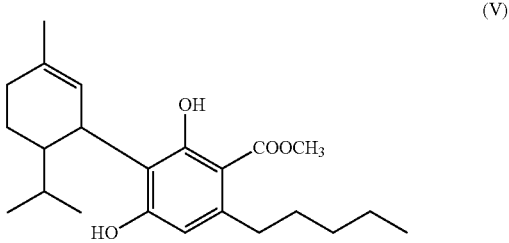 [SMILES: CCCCCc1cc(O)c(C2C=C(C)CCC2C(C)C)c(O)c1C(=O)OC]

or a pharmaceutically acceptable salt thereof.

8. The pharmaceutical composition of claim 1, wherein the compound is of formula (Va):

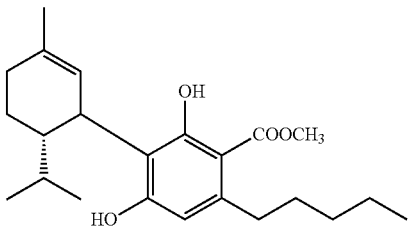

(Va)

or a pharmaceutically acceptable salt thereof.

9. The pharmaceutical composition of claim 1, further comprising one or more additional cannabinoid compounds comprised in one or more *cannabis* plant extracts.

10. The pharmaceutical composition of claim 9, wherein the *cannabis* plant extracts are produced from a plant strain selected from *Cannabis sativa, Cannabis indica, Cannabis ruderalis*, a hybrid strain, a strain with a high concentration of cannabidiol (CBD), a strain with a high concentration of tetrahydrocannabinol (THC), and a combination thereof.

11. The pharmaceutical composition of claim 9, wherein the one or more additional cannabinoid compounds are selected from cannabidiol (CBD), cannabigerol (CBG), Δ8-tetrahydrocannabinol (Δ8-THC), Δ9-tetrahydrocannabinol (Δ9-THC), cannabinol (CBN), Δ9(11)-tetrahydrocannabinol (exo-THC), cannabichromene (CBC), tetrahydrocannabinol-C3 (THC-C3), tetrahydrocannabinol-C4 (THC-C4), tetrahydrocannabinol-C7 (THC-C7), esters thereof, stereoisomers thereof, deuterated analogs thereof, fluorinated analogs thereof, and combination thereof.

12. The pharmaceutical composition of claim 9, wherein the pharmaceutical composition comprises 1-25% cannabidiol (CBD).

13. The pharmaceutical composition of claim 9, wherein the pharmaceutical composition comprises 1-25% tetrahydrocannabinol (THC).

14. The pharmaceutical composition of claim 1, wherein the composition is formulated for administration orally, topically, systemically, intravenously, subcutaneously, nasally, rectally, intramuscularly, intraperitoneally, transdermally, intra-arterially, intranasally, vaginally, by vaporization, or by inhalation.

15. The pharmaceutical composition of claim 1, wherein the composition is formulated as a tablet or capsule.

16. The pharmaceutical composition of claim 1, comprising a combination of cannabinoids, a pharmaceutical carrier, a co-solvent, a penetration enhancer, and an emulsifier.

17. The pharmaceutical composition of claim 16, comprising about 5% to 80% of the pharmaceutical carrier, about 50% of the co-solvent, about 1% to 5% of the penetration enhancer, about 0.1% to 20% of the emulsifier, and about 0.001% to 10% of the combination of cannabinoids.

18. A method of treating a disease or disorder, comprising administering a therapeutically effective amount the pharmaceutical composition of claim 1 to a subject in need thereof, wherein treating the disease or disorder is selected from the group consisting of:
  (i) treating a joint disease or dysfunction;
  (ii) treating a skin disease or disorder;
  (iii) treating a gastrointestinal disease or disorder;
  (iv) attenuating, alleviating, or treating a uterine-related disorder;
  (v) reducing or maintaining cholesterol levels or lowering LDL/HDL ratio; and
  (vi) treating Non-Alcoholic Fatty Liver Disease (NAFLD), chronic kidney disease (CDK).

19. A compound represented by formula (V):

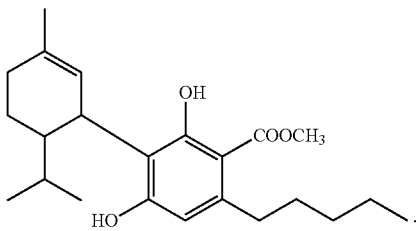

(V)

20. The compound of claim 19, wherein the compound is of formula (Va):

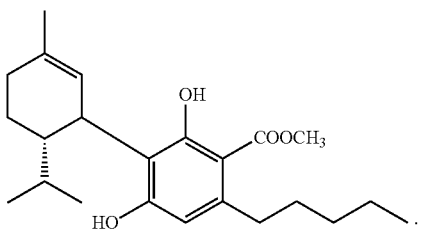

(Va)

* * * * *